(12) United States Patent
Zhang et al.

(10) Patent No.: US 11,319,325 B1
(45) Date of Patent: May 3, 2022

(54) MACROCYCLIC SPIROPYRROLIDINE DERIVED ANTIVIRAL AGENTS

(71) Applicant: Enanta Pharmaceuticals, Inc., Watertown, MA (US)

(72) Inventors: Jiajun Zhang, Cambridge, MA (US); Xiaowen Peng, Sudbury, MA (US); Joseph D. Panarese, Newton, MA (US); Guoqiang Wang, Belmont, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 17/479,669

(22) Filed: Sep. 20, 2021

Related U.S. Application Data

(60) Provisional application No. 63/187,138, filed on May 11, 2021.

(51) Int. Cl.
*C07D 487/20* (2006.01)

(52) U.S. Cl.
CPC ................ *C07D 487/20* (2013.01)

(58) Field of Classification Search
CPC .......... C07D 487/20; A61K 31/4155
USPC .......................................... 540/472; 514/406
See application file for complete search history.

(56) References Cited

U.S. PATENT DOCUMENTS

| | | |
|---|---|---|
| 9,290,757 B2 | 3/2016 | Madison |
| 9,328,147 B2 | 3/2016 | Wu et al. |
| 9,309,284 B2 | 4/2016 | Chang et al. |
| 9,347,044 B2 | 5/2016 | Brown et al. |
| 9,428,739 B2 | 8/2016 | Coit et al. |
| 9,447,382 B2 | 9/2016 | Mack |
| 9,474,759 B2 | 10/2016 | Chang et al. |
| 9,512,443 B2 | 12/2016 | Richmond et al. |
| 9,587,235 B2 | 3/2017 | Buechler et al. |
| 9,591,858 B2 | 3/2017 | Valles et al. |
| 9,688,978 B2 | 6/2017 | Buechler et al. |
| 9,772,328 B2 | 9/2017 | Stein et al. |
| 9,791,436 B2 | 10/2017 | Alexandrov et al. |
| 9,828,342 B2 | 11/2017 | Horne et al. |
| 9,975,885 B2 | 5/2018 | St. John et al. |
| 10,017,463 B2 | 7/2018 | Hedstrom et al. |
| 10,023,879 B2 | 7/2018 | Flynn et al. |
| 10,093,915 B2 | 10/2018 | Wu et al. |
| 10,130,701 B2 | 11/2018 | Bickerton et al. |
| 10,196,444 B2 | 2/2019 | Jarjour et al. |
| 10,221,396 B2 | 3/2019 | Brown et al. |
| 10,260,048 B2 | 4/2019 | Mack |
| 10,383,929 B2 | 8/2019 | Morgan et al. |
| 10,428,142 B2 | 10/2019 | Jarjour et al. |
| 10,457,731 B2 | 10/2019 | Jarjour et al. |
| 10,472,618 B2 | 11/2019 | Wu et al. |
| 10,479,975 B2 | 11/2019 | Friedman |
| 10,590,084 B2 | 3/2020 | Buckman et al. |
| 10,624,960 B2 | 4/2020 | Morgan et al. |
| 10,639,358 B2 | 5/2020 | Morgan et al. |
| 10,639,359 B2 | 5/2020 | Morgan et al. |
| 10,646,558 B2 | 5/2020 | Morgan et al. |
| 10,711,260 B2 | 7/2020 | Wu et al. |
| 10,774,343 B2 | 9/2020 | Morgan et al. |
| 10,784,994 B2 | 9/2020 | Yi et al. |
| 10,793,843 B2 | 10/2020 | Jarjour et al. |
| 10,927,367 B2 | 2/2021 | Jarjour et al. |
| 10,934,261 B2 | 3/2021 | Buckman et al. |
| 10,934,575 B2 | 3/2021 | Grosveld et al. |
| 10,954,529 B2 | 3/2021 | Flynn et al. |
| 10,959,969 B1 | 3/2021 | Johnson |
| 10,986,848 B2 | 4/2021 | Holz-Schietinger et al. |
| 11,013,779 B2 | 5/2021 | Chang et al. |
| 11,020,466 B2 | 6/2021 | Morgan et al. |
| 11,021,513 B2 | 6/2021 | Schinazi et al. |

(Continued)

FOREIGN PATENT DOCUMENTS

| | | |
|---|---|---|
| WO | 2004101742 A3 | 11/2004 |
| WO | 2005113580 | 12/2005 |

(Continued)

OTHER PUBLICATIONS

PubChem, SID 367622864, May 25, 2018.

(Continued)

*Primary Examiner* — Jeffrey H Murray
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, thereof:

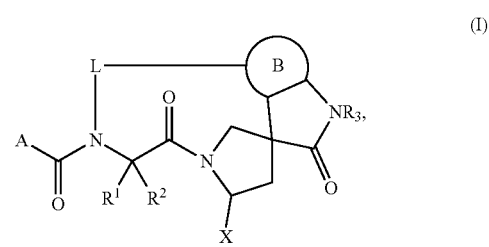

(I)

which inhibit coronavirus replication activity. The invention further relates to pharmaceutical compositions comprising a compound of Formula (I) or a pharmaceutically acceptable salt thereof, and methods of treating or preventing a coronavirus infection in a subject in need thereof, comprising administering to the subject a therapeutically effective amount of a compound of Formula (I) or a pharmaceutically acceptable salt thereof.

24 Claims, No Drawings

(56) References Cited

U.S. PATENT DOCUMENTS

| | | |
|---|---|---|
| 11,033,600 B2 | 6/2021 | Chang et al. |
| 11,045,546 B1 | 6/2021 | Kelly et al. |
| 11,058,763 B2 | 7/2021 | Zhang et al. |
| 11,058,779 B2 | 7/2021 | Lu et al. |
| 11,072,787 B2 | 7/2021 | Wu et al. |
| 11,124,497 B1 | 9/2021 | Arnold et al. |
| 11,174,231 B1 | 11/2021 | Arnold et al. |
| 11,207,370 B2 | 12/2021 | Schinazi et al. |
| 2005/0143320 A1 | 6/2005 | Yang et al. |
| 2006/0014821 A1 | 1/2006 | He et al. |
| 2009/0137818 A1 | 5/2009 | Hilgenfeld et al. |
| 2014/0243341 A1 | 8/2014 | Chang et al. |
| 2021/0355111 A1 | 11/2021 | Arnold et al. |

FOREIGN PATENT DOCUMENTS

| | | |
|---|---|---|
| WO | 2006061714 | 8/2006 |
| WO | 2012099454 A1 | 7/2012 |
| WO | 2013049382 A3 | 5/2013 |
| WO | 2013166319 A1 | 11/2013 |
| WO | 2018042343 A2 | 3/2018 |
| WO | 2021205296 A1 | 10/2021 |
| WO | 2021206876 A1 | 10/2021 |
| WO | 2021206877 A1 | 10/2021 |
| WO | 2021207409 A2 | 10/2021 |
| WO | 2021226546 A1 | 11/2021 |
| WO | 2021250648 A1 | 12/2021 |
| WO | 2021252491 A1 | 12/2021 |
| WO | 2022020711 A1 | 1/2022 |

OTHER PUBLICATIONS

Zhou, L. et al., "An Overview of Spirooxindole as a Promising Scaffold for Novel Drug Discovery", Expert Opinion on Drug Discovery, vol. 15, Iss. 5, Feb. 2020, 603-625.

Lee., C. et al., "Structural Basis of Inhibition Specificities of 3C and 3C-like Proteases by Zinc-coordinating and Peptidomimetic Compounds", J. Biological Chem., vol. 284, No. 12, Mar. 20, 2009, 7646-7655.

Yang, S. et al., "Synthesis, Crystal Structure, Structure-Activity Relationships, and Antiviral Activity of a Potent SARS Coronavirus 3CL Protease Inhibitor", J. Med. Chem., vol. 49, Jul. 14, 2006, 4971-4980.

Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.

Halford, B., "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/9940141367US1File/i13, (a version appeared in 99(13)), Apr. 7, 2021, 2 pgs.

Halford, B., "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.

Xu, J. et al., "Green Oxidation of Indoles Using Halide Catalysis", Nature Communications, 10:4754, https://doi.org/10.1038/s41467-019-12768-4, Oct. 18, 2019, 1-11.

Konno, S., et al. "3CL Protease Inhibitors with an Electrophilic Arylketone Moiety as Anti-SARS-CoV-2 Agents," J. Medicinal Chemistry, https://doi.org/10.102t/acs.jmedchem.1c006S5, pp. 1-14, (2021).

U.S. Appl. No. 17/506,981, filed Oct. 21, 2021.
U.S. Appl. No. 17/379,409, filed Jul. 19, 2021.
U.S. Appl. No. 17/479,244, filed Sep. 20, 2021.
U.S. Appl. No. 17/479,248, filed Sep. 20, 2021.
U.S. Appl. No. 17/479,455, filed Sep. 20, 2021.
U.S. Appl. No. 17/479,530, filed Sep. 20, 2021.

MACROCYCLIC SPIROPYRROLIDINE DERIVED ANTIVIRAL AGENTS

RELATED APPLICATION

This application claims the benefit of U.S. Provisional Application No. 63/187,138, filed May 11, 2021. The entire teachings of the above application are incorporated herein by reference.

TECHNICAL FIELD

The invention relates to compounds and methods of inhibiting coronavirus replication activity by contacting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are enveloped, positive-sense, single-stranded RNA viruses. The genomic RNA of CoVs has a 5'-cap structure and 3'-poly-A tail, and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO2018/042343, WO2018/023054, WO2005/113580, and WO2006/061714).

More effective therapies for coronavirus infections are needed due to this high unmet clinical need. This invention describes the methods to prepare and methods for use of compounds that are believed to inhibit the coronavirus lifecycle. Compounds of this type might be used to treat coronavirus infections and decrease occurrence of disease complications such as organ failure or death.

There is a need in the art for novel therapeutic agents that treat, ameliorate or prevent coronavirus infection. Administration of these therapeutic agents to a coronavirus infected patient, either as monotherapy or in combination with other coronavirus treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

The present invention provides compounds represented by Formula (I), and pharmaceutically acceptable salts, esters and prodrugs thereof, wherein:

$R_1$ is selected from the group consisting of hydrogen, halogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

$R_2$ is selected from the group consisting of hydrogen, halogen, optionally substituted —$C_1$-$C_6$ alkyl, and optionally substituted —$C_3$-$C_6$ cycloalkyl; preferably, $R_2$ is hydrogen.

$R_3$ is hydrogen, optionally substituted —$C_1$-$C_4$ alkyl, optionally substituted $C_2$-$C_4$-alkenyl, or optionally substituted —$C_3$-$C_6$ cycloalkyl; preferably, $R_3$ is hydrogen.

Alternatively, $R_1$ and $R_2$ are taken together with the carbon atom to which they are attached to form an optionally substituted 3- to 6-membered cycloalkyl ring or heterocyclic ring;

A is selected from the group consisting of —$R_{11}$, —$OR_{12}$, —$NR_{13}R_{14}$, —$C(O)NR_{13}R_{14}$, —$C(R_{18}R_{19})NR_{15}C(O)R_{11}$, —$C(R_{18}R_{19})NR_{15}C(O)OR_{12}$, —$C(R_{18}R_{19})NR_{15}C(O)NR_{13}R_{14}$, and —$C(R_{18}R_{19})NR_{15}C(O)C(O)NR_{13}R_{14}$;

$R_{11}$ and $R_{12}$ are each independently selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, or optionally substituted heteroarylalkyl;

$R_{13}$ and $R_{14}$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; alternatively $R_{13}$ and $R_{14}$ are taken together with the nitrogen atom to which they are attached to form an optionally substituted 3- to 8-membered heterocyclic ring;

$R_{15}$ is hydrogen or optionally substituted —$C_1$-$C_8$ alkyl;

$R_{18}$ is selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

$R_{19}$ is selected from the group consisting of hydrogen, halogen, optionally substituted —$C_1$-$C_6$ alkyl, and optionally substituted —$C_3$-$C_6$ cycloalkyl;

alternatively $R_{15}$ and $R_{19}$ are taken together with the atoms to which they are attached to form an optionally substituted 5- or 6-membered heterocyclic;

alternatively $R_{18}$ and $R_{19}$ are take together with the carbon atom to which they are attached to form an optionally substituted 5- or 6-membered carbocyclic or heterocyclic;

B is an optionally substituted aryl or optionally substituted heteroaryl;

X is selected from the group consisting of: —CN, —C(O)$R_{15}$, —CH(OH)SO$_3$R$_{16}$, —C(O)NR$_{13}$R$_{14}$, —C(O)C(O)NR$_{13}$R$_{14}$, —C≡CR$_{13}$; —CH=CH—C(O)OR$_{12}$, —CH=CH—C(O)NR$_{13}$R$_{14}$, —CH=CH—S(O)$_2$NR$_{13}$R$_{14}$, and —B(OR$_{13}$)$_2$;

$R_{16}$ is hydrogen or Na$^+$;

L is —$R_a$-Q-$R_b$—, wherein when $R_a$ is not absent, $R_a$ is connected to B and when $R_a$ is absent, Q is connected to B;

$R_a$ is selected from the group consisting of absent, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_a$ is absent;

$R_b$ is selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

Q is selected from the group consisting of —CR$_{21}$=CR$_{22}$—, —CR$_{21}$R$_{23}$—CR$_{22}$R$_{24}$—, —CR$_{21}$R$_{23}$C(O)—, —CR$_{21}$R$_{23}$—O—, —CR$_{21}$R$_{23}$—S—, —CR$_{21}$R$_{23}$N(R$_{17}$)—, —NR$_{13}$C(O)—, —NR$_{13}$C(O)O—, —NR$_{13}$C(O)NR$_{14}$—, —C(O)O—, —C(O)S—, —OC(O)O—, —C(O)—, O—, —S—, —S(O)—, —S(O)$_2$—, —S(O)(NH)—, —N(R$_{17}$)—, optionally substituted aryl, optionally substituted heteroaryl, optionally substituted —$C_3$-$C_8$ cycloalkyl, and optionally substituted 3- to 8-membered heterocycloalkyl;

$R_{17}$ is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, optionally substituted heteroarylalkyl, —C(O)R$_{11}$, —C(O)OR$_{12}$, —C(O)NR$_{13}$R$_{14}$, —C(O)C(O)NR$_{13}$R$_{14}$, —S(O)$_2$R$_{11}$, and —S(O)$_2$NR$_{13}$R$_{14}$;

$R_{21}$ and $R_{22}$ at each occurrence are each independently selected from the group consisting of hydrogen, halogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_{21}$ and $R_{22}$ are both hydrogen; and $R_{23}$ and $R_{24}$ at each occurrence are each independently selected from the group consisting of: hydrogen, halogen, —OH, —OR$_{12}$, —OC(O)R$_{11}$, —OC(O)OR$_{12}$, —OC(O)NR$_{13}$R$_{14}$, —NR$_{13}$R$_{17}$, —N$_3$, —CN, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_{23}$ and $R_{24}$ are both hydrogen;

alternatively, $R_{21}$ and $R_{23}$ are taken together with the carbon atom to which they are attached to form an optionally substituted —$C_3$-$C_6$ cycloalkyl or a 3- to 6-membered heterocyclic; alternatively, $R_{22}$ and $R_{24}$ are taken together with the carbon atom to which they are attached to form an optionally substituted —$C_3$-$C_6$ cycloalkyl or a 3- to 6-membered heterocyclic.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), $R_1$ is optionally substituted —$C_1$-$C_4$ alkyl, optionally substituted —$C_3$-$C_6$ cycloalkyl, optionally substituted aryl, optionally substituted arylalkyl, or optionally substituted heteroarylalkyl.

In certain embodiments of the compounds of Formula (I), $R_1$ is selected from the following groups:

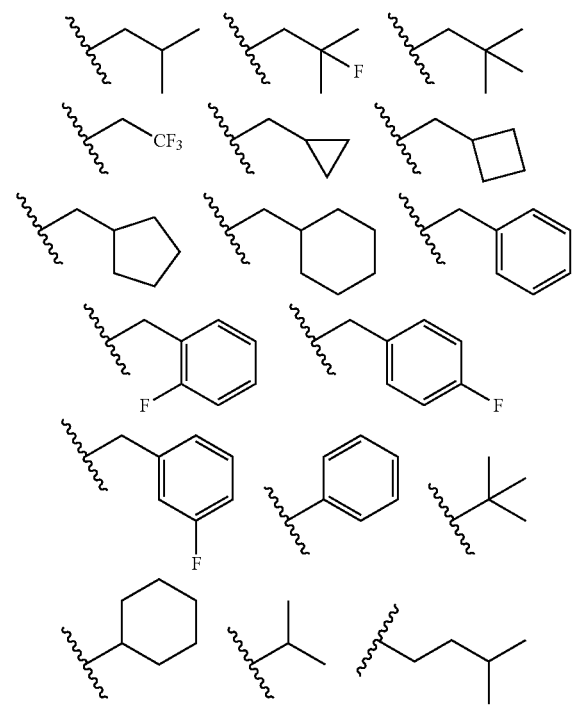

-continued

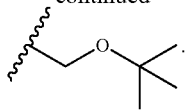

In certain embodiments of the compounds of Formula (I), $R_1$ is selected from the following groups:

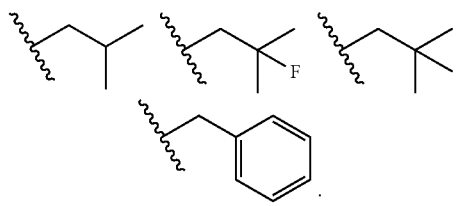

In certain embodiments of the compounds of Formula (I), $R_2$ is hydrogen or F.

In certain embodiments of the compounds of Formula (I), $R_3$ is hydrogen.

In certain embodiments of the compounds of Formula (I), X is —CN.

In certain embodiments of the compounds of Formula (I), X is —C(O)H.

In certain embodiments of the compounds of Formula (I), X is —C≡CR$_{13}$, wherein R$_{13}$ are previously defined.

In certain embodiments of the compounds of Formula (I), X is —C(O)CH$_2$OH, —C(O)CH$_2$Cl or —C(O)CH$_2$F.

In certain embodiments of the compounds of Formula (I), X is —C(O)C(O)NR$_{13}$R$_{14}$, wherein R$_{13}$ and R$_{14}$ are previously defined.

In certain embodiments of the compounds of Formula (I), X is selected from the following:

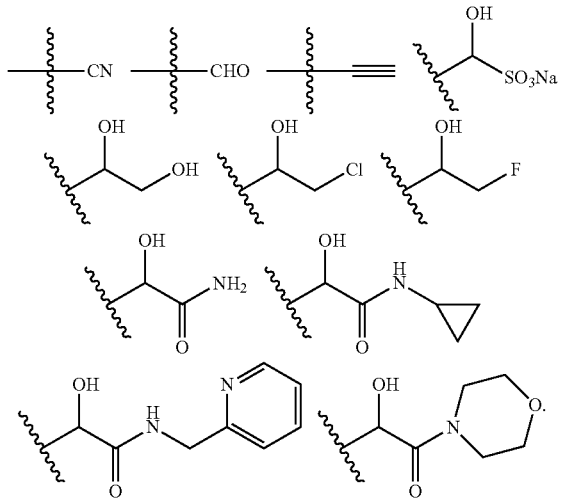

In certain embodiments of the compounds of Formula (I), A is optionally substituted —C$_1$-C$_8$ alkyl, optionally substituted aryl or optionally substituted heteroaryl.

In certain embodiments of the compounds of Formula (I), A is derived from one of the following by removal of a hydrogen atom and is optionally substituted:

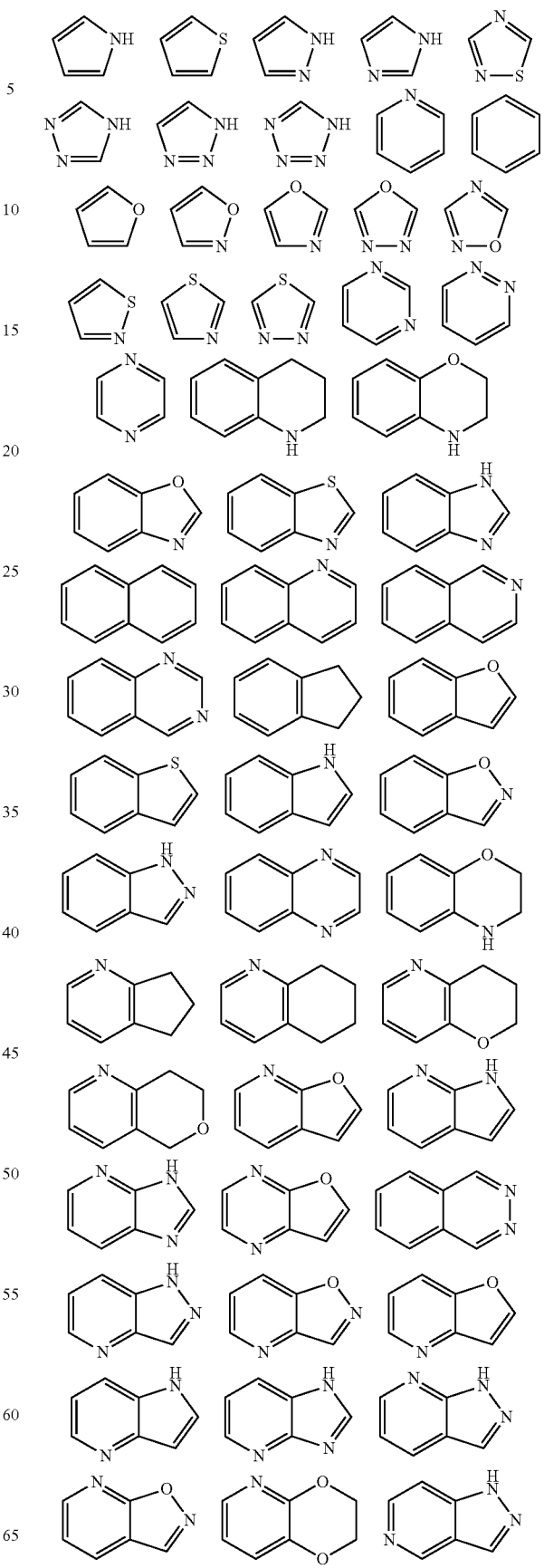

-continued
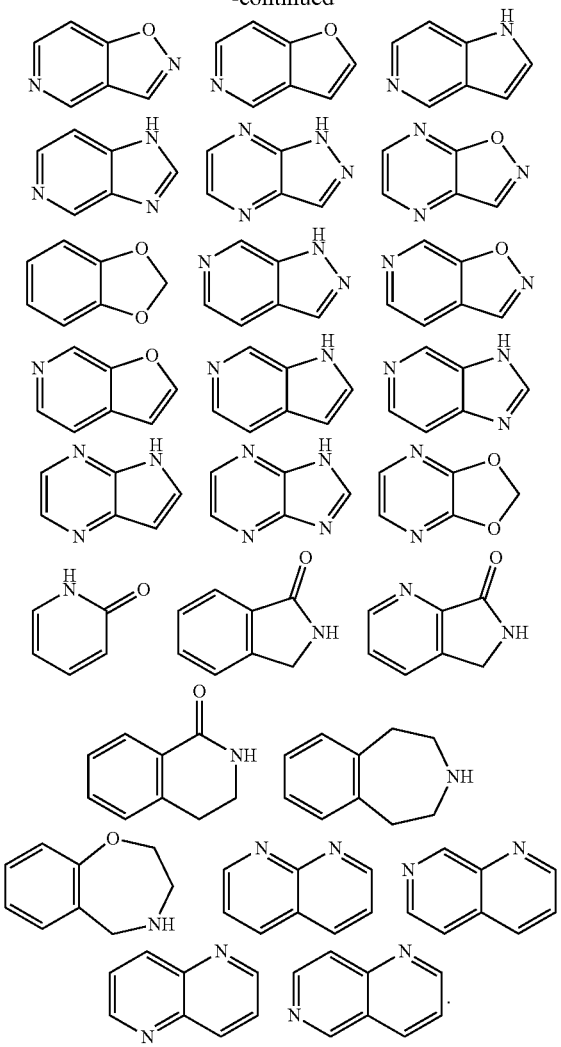
In certain embodiments of the compounds of Formula (I), A is selected from the following groups, and A is optionally substituted:
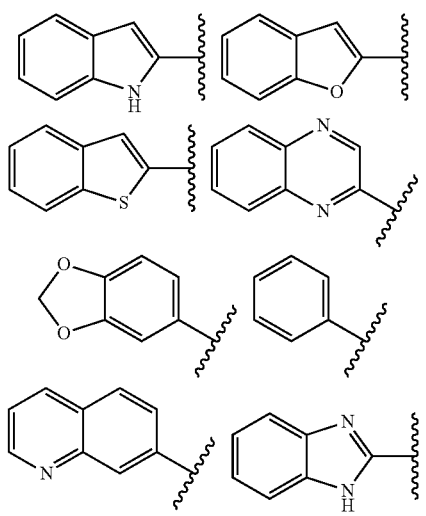
-continued
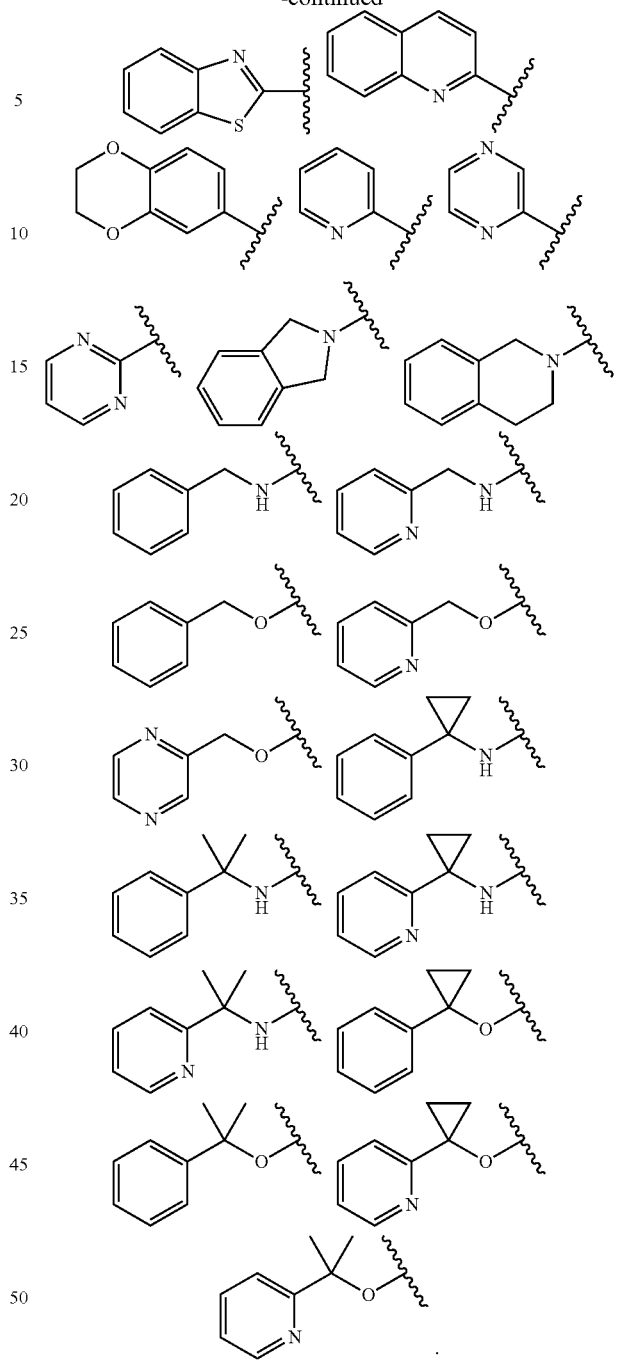
In certain embodiments of the compounds of Formula (I), A is selected from the following groups, and A is optionally substituted:
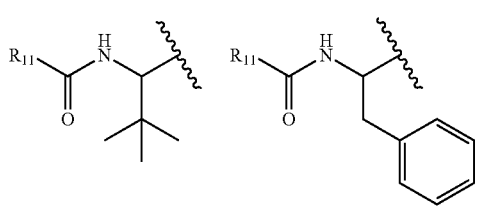

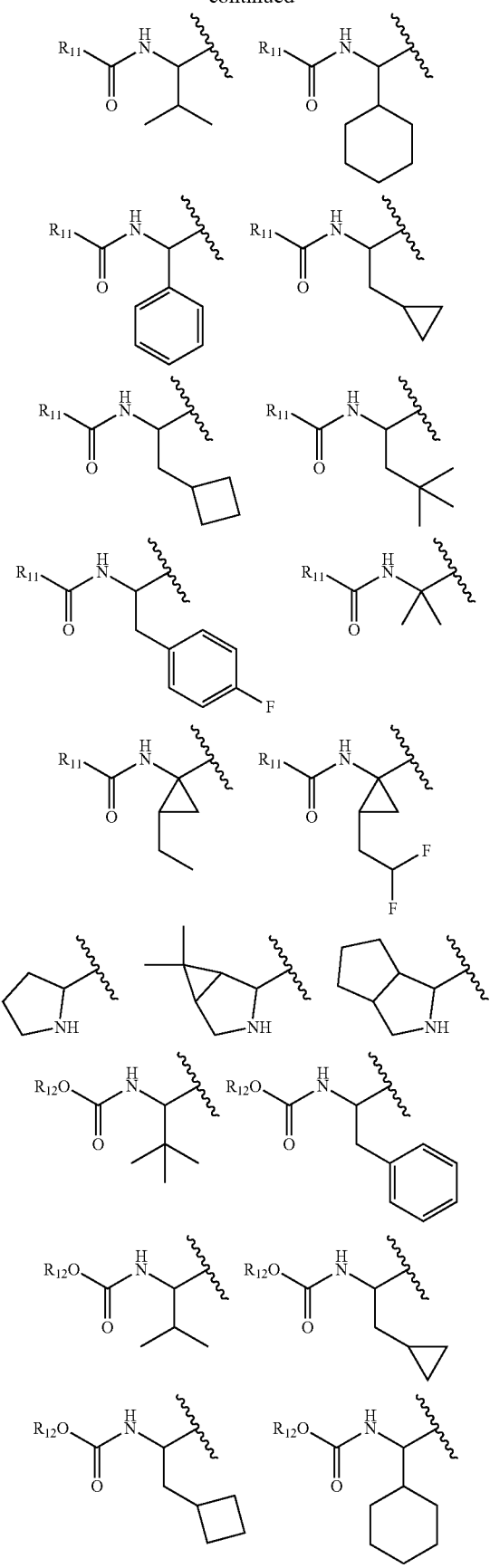
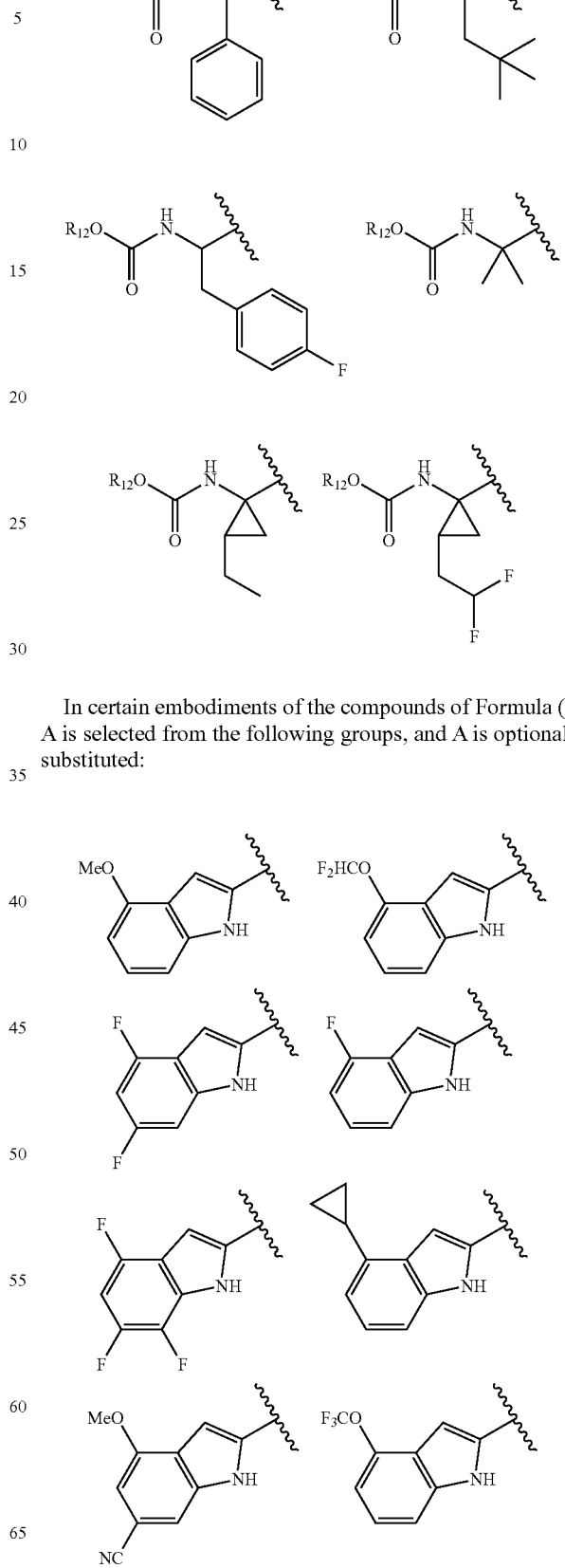
In certain embodiments of the compounds of Formula (I), A is selected from the following groups, and A is optionally substituted:

-continued
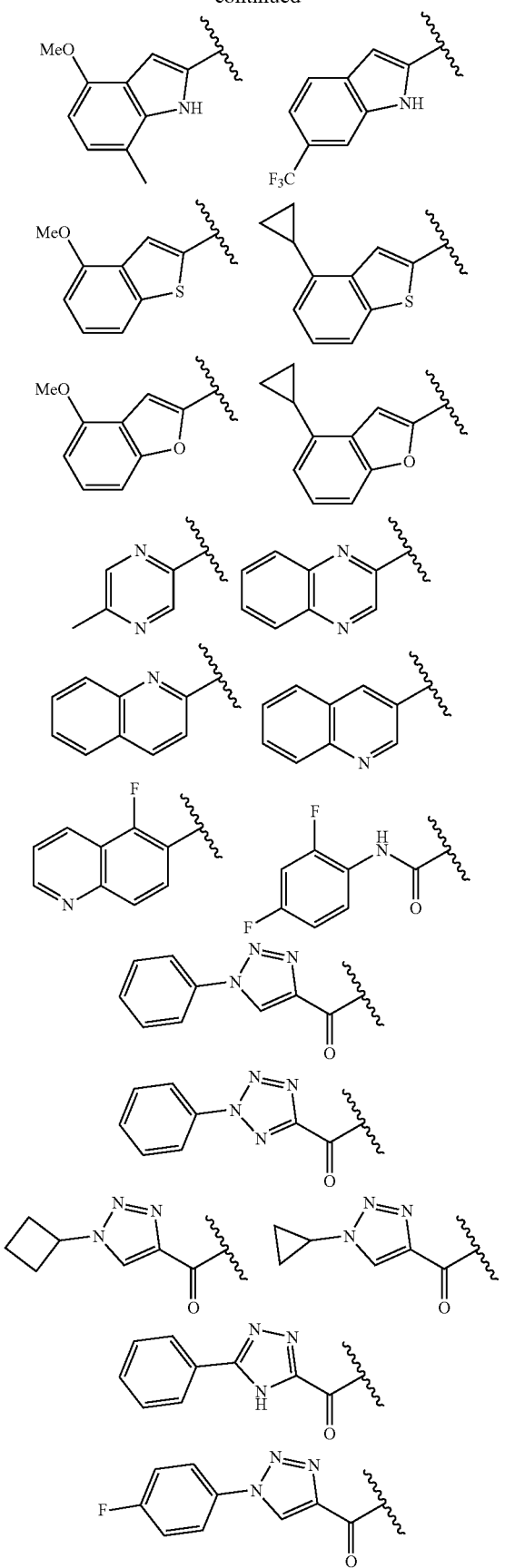
-continued
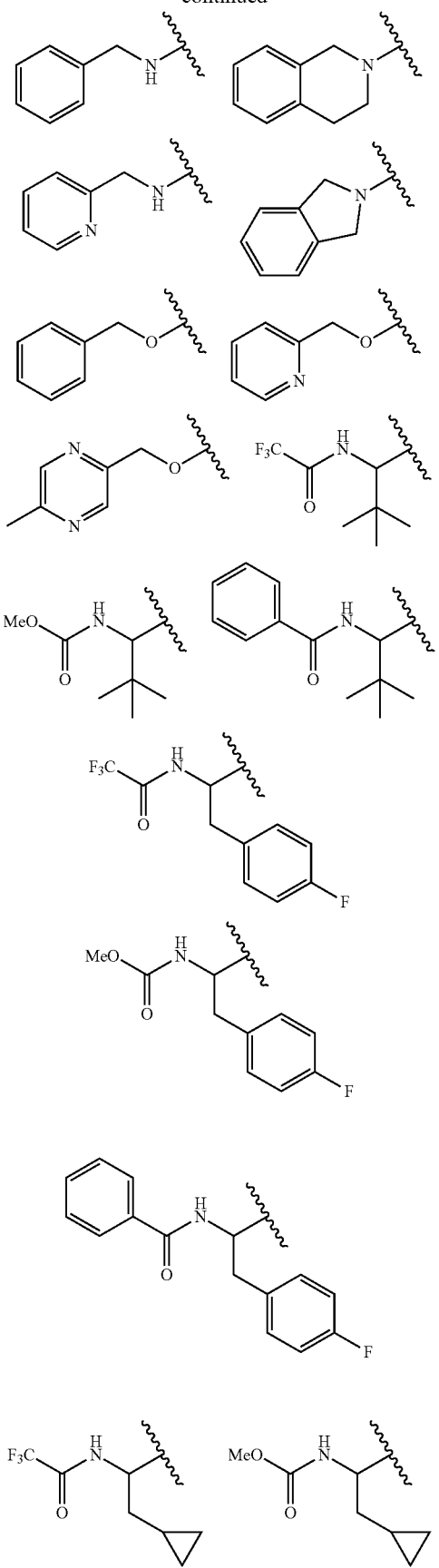

-continued

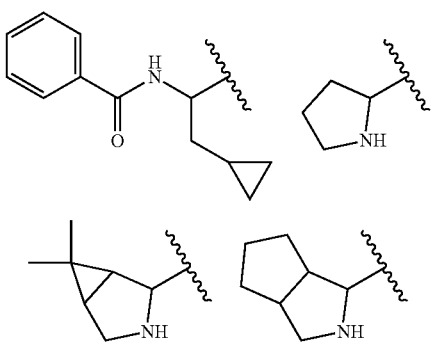

In certain embodiments of the compounds of Formula (I), L is selected from the following groups, and L is optionally substituted:

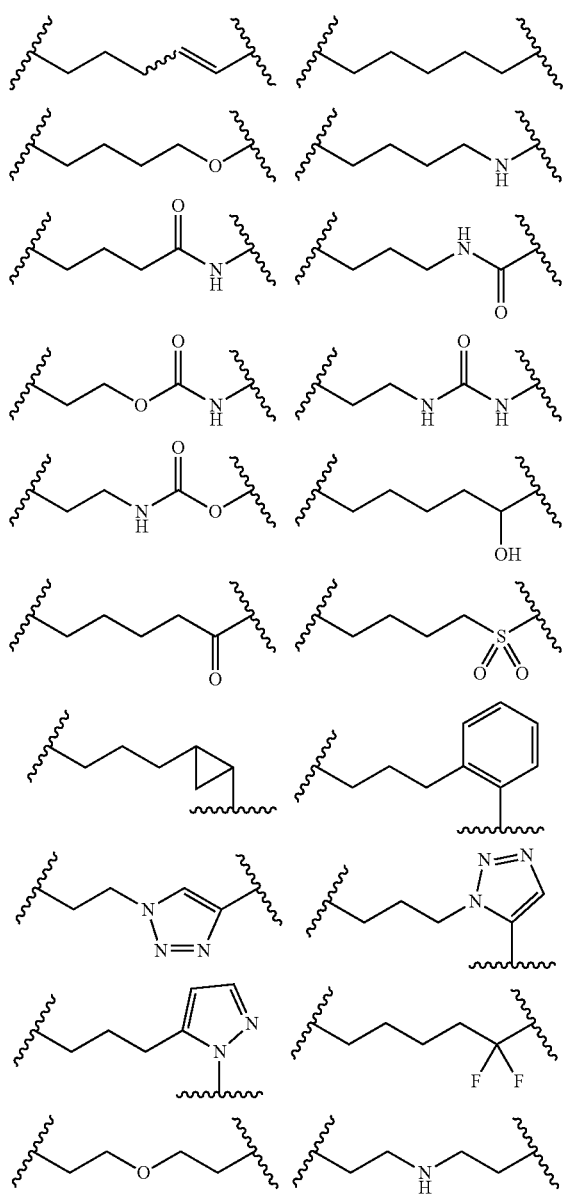

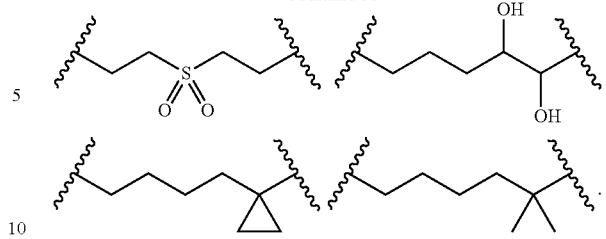

In certain embodiments of the compounds of Formula (I), L is —CH$_2$—(CH$_2$)$_2$—CH$_2$—, —CH$_2$—CH=CH—CH$_2$—, —CH$_2$—(CH$_2$)$_3$—CH$_2$—, or —CH$_2$—CH=CH—CH$_2$—CH$_2$—.

In certain embodiments of the compounds of Formula (I), L is cis-(CH$_2$)$_p$—CH=CH—, where p is 1, 2, 3 or 4, preferably p is 2, 3 or 4. Preferably the olefinic carbon atom is connected to B.

In certain embodiments of the compounds of Formula (I), B is optionally substituted phenyl or optionally substituted pyridinyl.

In certain embodiments, the compound of Formula (I) is represented by Formula (I-a) or Formula (I-b):

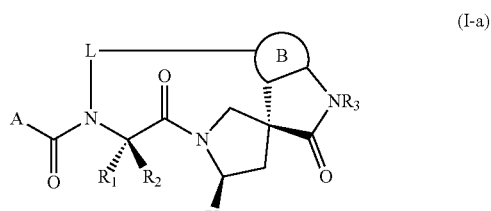

(I-a)

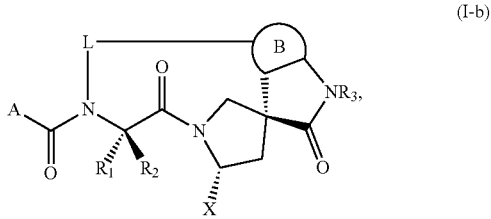

(I-b)

wherein A, B, R$_1$, R$_2$, R$_3$, L and X are as previously defined.

In a preferred embodiment, the compound of Formula (I) has the stereochemistry shown in Formula (I-a).

In certain embodiments, the compound of Formula (I) is represented by Formula (II):

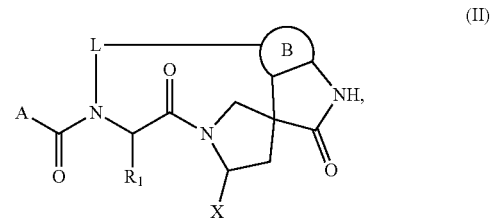

(II)

wherein A, B, R$_1$, L and X are as previously defined.

In certain embodiments, the compound of Formula (I) is represented by one of Formulae (III-1)~(III-3):

(III-1)

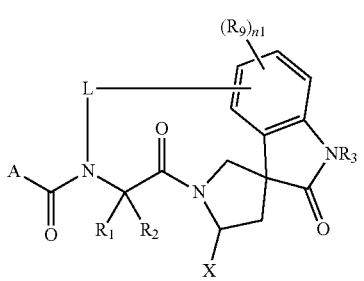

(III-2)

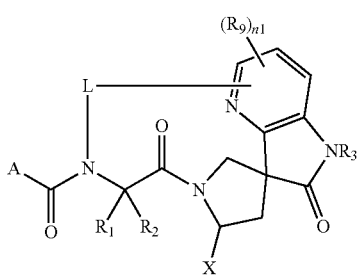

(III-3)

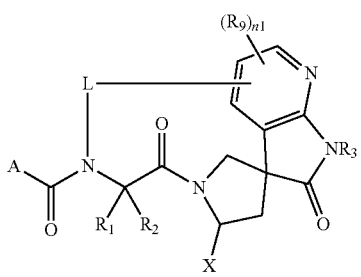

wherein A, $R_1$, $R_2$, $R_3$, L and X are as previously defined. $R_9$ is independently selected from the group consisting of: halogen, —CN, —$OR_{12}$, —$OC(O)R_{11}$, —$OC(O)NR_{13}R_{14}$, —$C(O)NR_{13}R_{14}$, —$SR_{12}$, —$S(O)Rn$, —$S(O)_2$—$R_{11}$, —$S(O)(NH)R_{11}$, —$S(O)_2$—$NR_{13}R_{14}$, —$NR_{13}R_{17}$, optionally substituted —$C_1$-$C_6$ alkyl, optionally substituted —$C_3$-$C_8$ cycloalkyl, optionally substituted 3- to 8-membered heterocycloalkyl, optionally substituted aryl, and optionally substituted heteroaryl, n1 is 0, 1, 2, or 3, and n2 is 0, 1, or 2.

In certain embodiments, the compound of Formula (I) is represented by Formula (TV):

(IV)

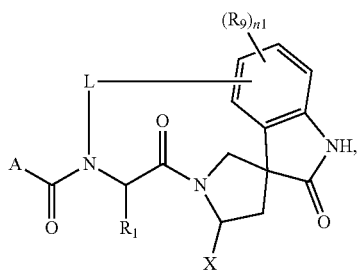

wherein A, $R_1$, $R_9$, n1, L and X are as previously defined.

In certain embodiments, the compound of Formula (I) is represented by Formula (IV-a) or Formula (IV-b):

(IV-a)

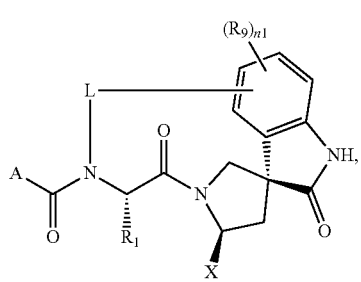

(IV-b)

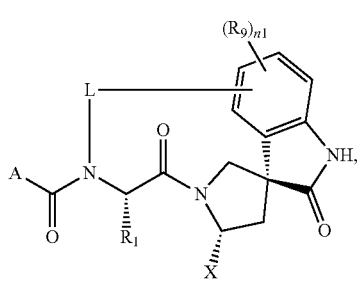

wherein A, $R_1$, $R_9$, n1, L and X are as previously defined.

In a preferred embodiment, the compound of Formula (I) has the stereochemistry shown in Formula (IV-a).

In certain embodiments, the compound of Formula (I) is represented by the Formula (V):

(V)

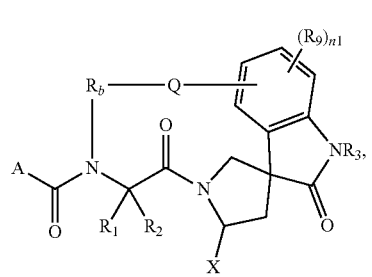

wherein A, $R_1$, $R_2$, $R_3$, $R_9$, $R_b$, Q, n1, and X are as previously defined. Preferably $R_2$ is hydrogen and $R_3$ is hydrogen.

In certain embodiments, the compound of Formula (I) is represented by Formula (VI-1) or Formula (VI-2):

(VI-1)

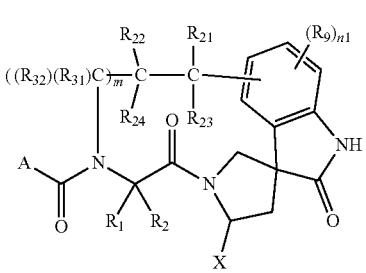

-continued

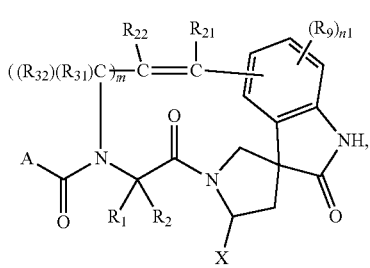

(VI-2)

wherein A, $R_1$, $R_2$, $R_9$, $R_{21}$, $R_{22}$, $R_{23}$, $R_{24}$, n1, and X are as previously defined. $R_{31}$ and $R_{32}$ are each independently selected from the group consisting of hydrogen, halogen, optionally substituted —$C_1$-$C_6$ alkyl, and optionally substituted —$C_3$-$C_6$ cycloalkyl; and m is 1, 2, 3, 4, 5, or 6. Preferably, $R_{31}$ and $R_{32}$ are each independently selected from the group consisting of hydrogen, fluorine, methyl, —$CF_3$ and cyclopropyl, and $R_2$ is hydrogen.

In certain embodiments, the compound of Formula (I) is represented by one of Formula (VII):

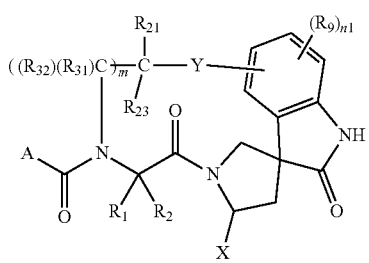

(VII)

wherein Y is independently selected from the group consisting of —O—, —S—, —S(O)$_2$—, —S(O)(NH)—, and —NR$_{17}$—; A, $R_1$, $R_2$, $R_9$, $R_{17}$, $R_{21}$, $R_{23}$, $R_{31}$, $R_{32}$, n1, m and X are as previously defined. Preferably, $R_{31}$ and $R_{32}$ are each independently selected from the group consisting of hydrogen, fluorine, methyl, —$CF_3$ and cyclopropyl, and $R_2$ is hydrogen.

In certain embodiments, the compound of Formula (I) is represented by Formula (VIII):

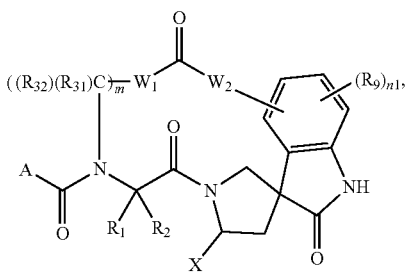

(VIII)

wherein $W_1$ and $W_2$ are independently selected from the group consisting of absent, —O—, —NR$_{13}$—, and —CR$_{21}$R$_{23}$—; wherein A, $R_1$, $R_2$, $R_9$, $R_{13}$, $R_{21}$, $R_{23}$, $R_{31}$, $R_{32}$, n1, m, and X are as previously defined. Preferably, $R_{31}$ and $R_{32}$ are each independently selected from the group consisting of hydrogen, fluorine, methyl, —$CF_3$ and cyclopropyl, and $R_2$ is hydrogen.

In certain embodiments, the present invention provides compounds of Formula (IX):

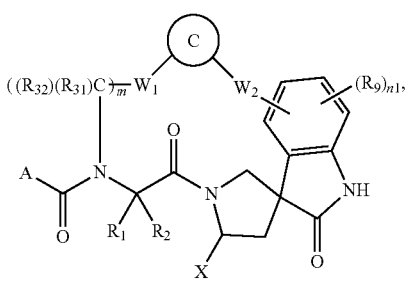

(IX)

wherein Ⓒ is selected from the group consisting of optionally substituted aryl, optionally substituted heteroaryl, optionally substituted —$C_3$-$C_8$ cycloalkyl, and optionally substituted 3- to 8-membered heterocycloalkyl; and A, $R_1$, $R_2$, $R_9$, $R_{31}$, $R_{32}$, $W_1$, $W_2$, n1, m and X are as previously defined. Preferably, $W_2$ is absent. Preferably, $R_{31}$ and $R_{32}$ are each independently selected from the group consisting of hydrogen, fluorine, methyl, —$CF_3$, and cyclopropyl, and $R_2$ is hydrogen.

In certain embodiments, the compound of Formula (I) is represented by one of Formulae (X-1) and (X-2):

(X-1)

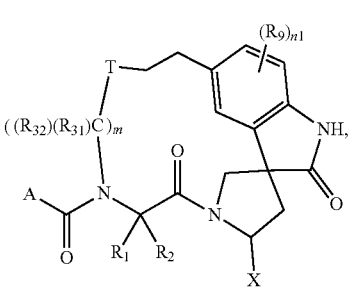

(X-2)

wherein T is —CH=CH—, —$CF_2$—, —$C(CH_3)_2$—, —O—, —S—, —C(O)—, —S(O)$_2$—, —S(O)(NH)—, —NR$_{13}$—, optionally substituted —$C_3$-$C_6$ cycloalkyl, optionally substituted 3- to 6-membered heterocycloalkyl, optionally substituted aryl, or optionally substituted heteroaryl; A, $R_1$, $R_9$, $R_{13}$, $R_{31}$, $R_{32}$, m, n1 and X are as previously defined. Preferably, X is —CN.

In certain embodiments, the compound of Formula (I) is represented by one of Formulae (X-1a) and (X-2a):

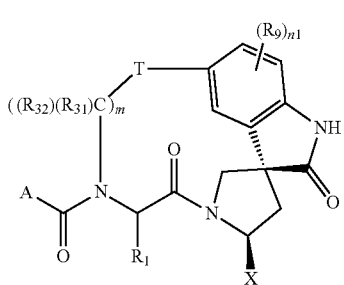
(X-1a)

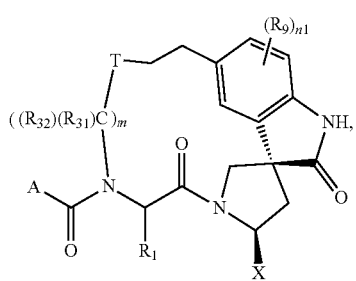
(X-2a)

wherein T, n1, A, R$_1$, R$_9$, R$_{13}$, R$_{31}$, R$_{32}$, m and X are as previously defined. Preferably, X is —CN.

In certain embodiments, the compound of Formula (I) is represented by one of Formulae (XI-1) and (XI-2):

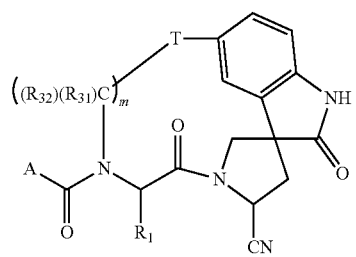
(XI-1)

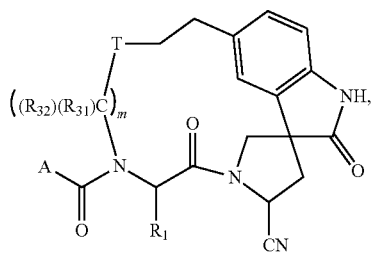
(XI-2)

wherein T, A, R$_1$, R$_{31}$, R$_{32}$, and m are as previously defined.

In certain embodiments, the compound of Formula (I) is represented by one of Formulae (XI-1a) and (XI-2a):

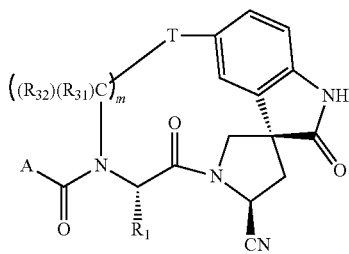
(XI-1a)

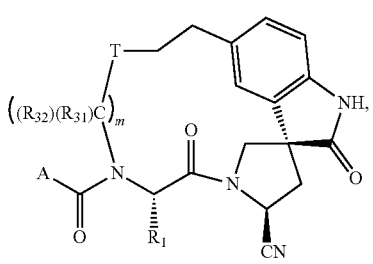
(XI-2a)

wherein T, A, R$_1$, R$_{31}$, R$_{32}$, and m are as previously defined.

In certain embodiments, the compound of Formula (I) is represented by one of Formulae (XII-1)~(XII-6):

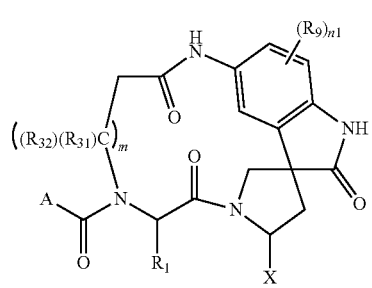
(XII-1)

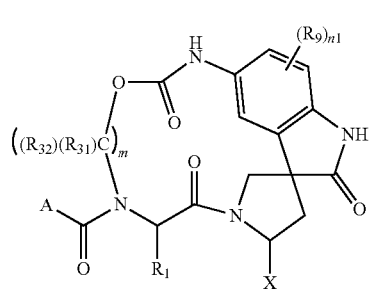
(XII-2)

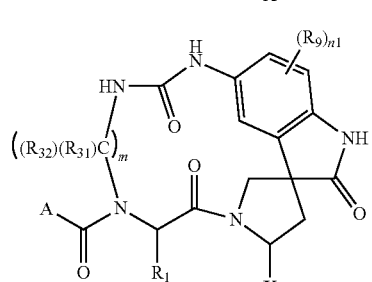
(XII-3)

(XII-4)
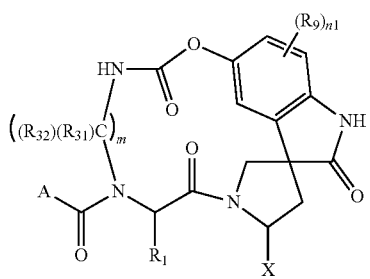

(XII-5)
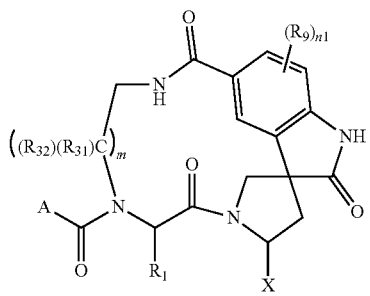

(XII-6)
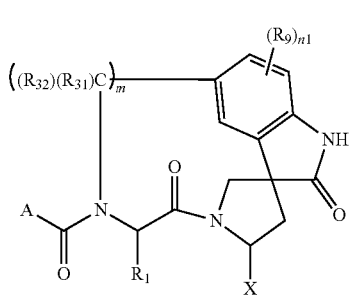

wherein n1, A, $R_1$, $R_9$, $R_{31}$, $R_{32}$, m and X are as previously defined. Preferably, X is —CN.

In certain embodiments, the compound of Formula (I) is represented by one of Formulae (XII-1a)~(XII-6a):

(XII-1a)
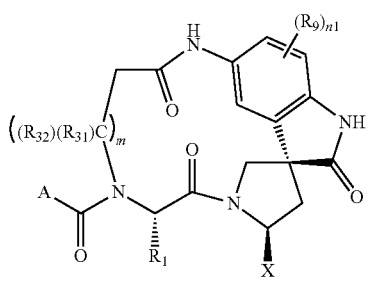

(XII-2a)
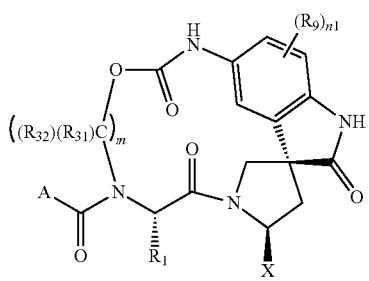

(XII-3a)
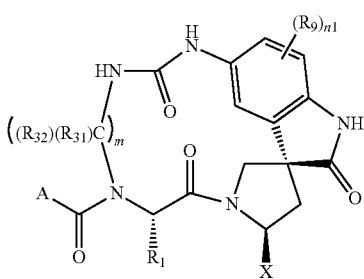

(XII-4a)
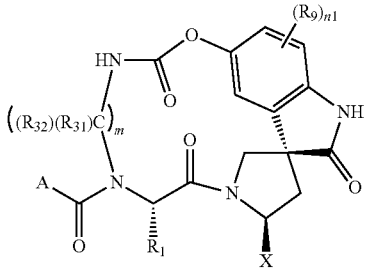

(XII-5a)
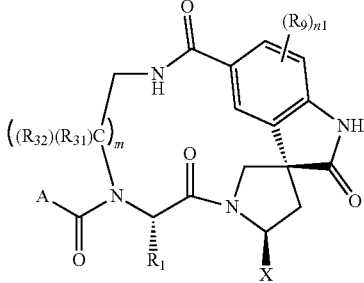

(XII-6a)
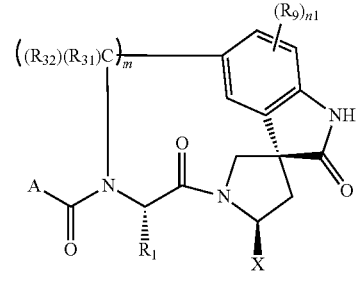

wherein n1, A, $R_1$, $R_9$, $R_{31}$, $R_{32}$, m and X are as previously defined. Preferably, X is —CN.

In certain embodiments, the compound of Formula (I) is represented by one of Formulae (XIII-1)~(XIII-6):

(XIII-1)
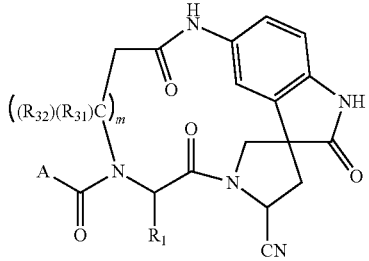

(XIII-2)
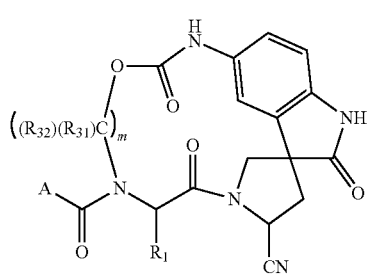
(XIII-3)
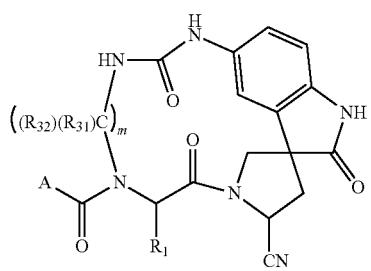
(XIII-4)
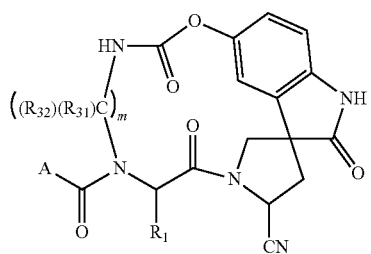
(XIII-5)
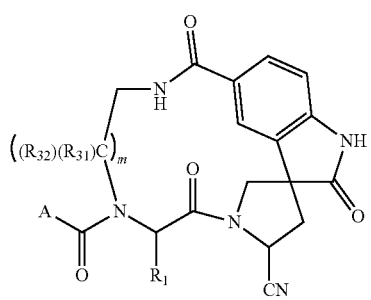
(XIII-6)
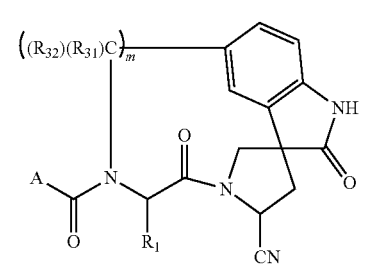
wherein A, $R_1$, $R_{31}$, $R_{32}$, and m are as previously defined.
In certain embodiments, the compound of Formula (I) is represented by one of Formulae (XIII-1a)~(XIII-6a):
(XIII-1a)
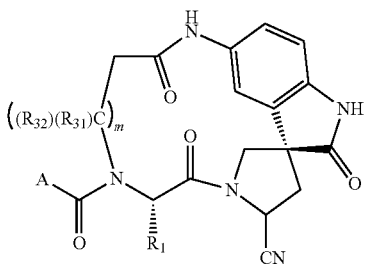
(XIII-2a)
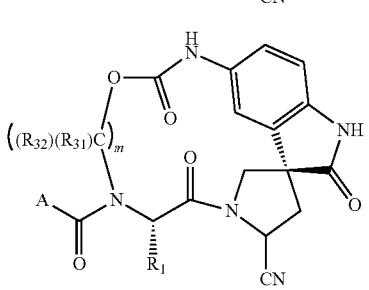
(XIII-3a)
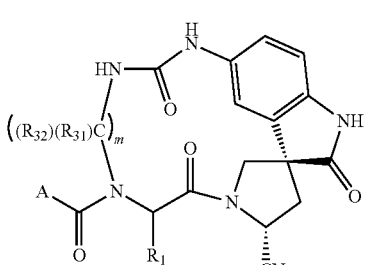
(XIII-4a)
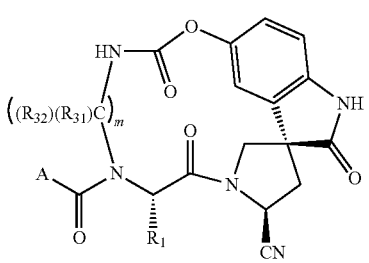
(XIII-5a)
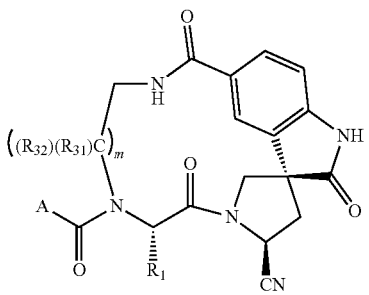
(XIII-6a)
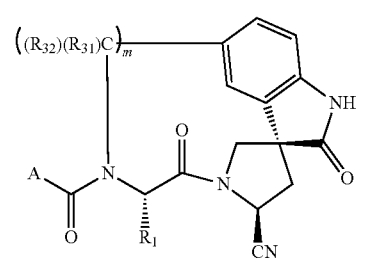
wherein A, $R_1$, $R_{31}$, $R_{32}$, and m are as previously defined.

In certain embodiments, the compound of Formula (I) is represented by one of Formulae (XIII-1)~(XIII-6) and (XIII-1a)~(XIII-6a), wherein $R_1$ is selected from the following groups:
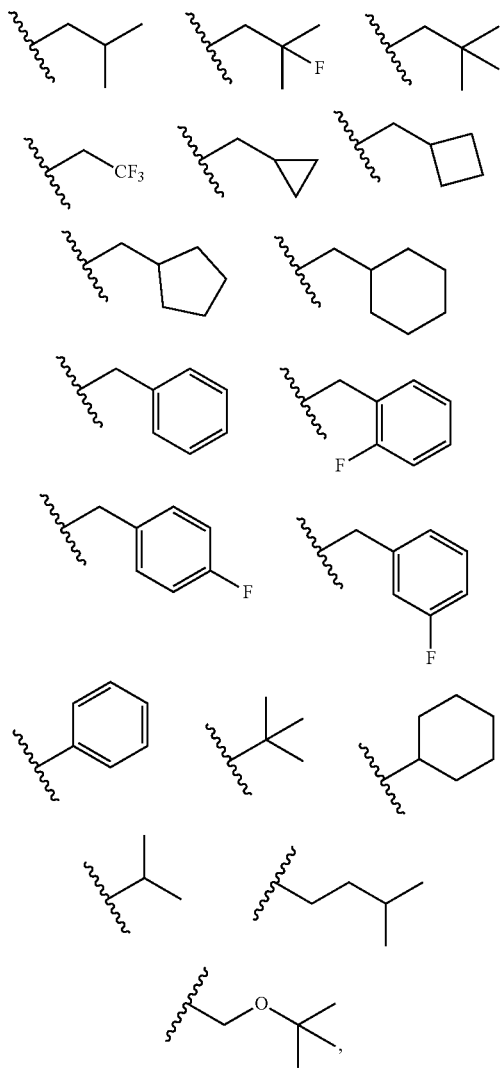
and A is selected from the following groups, wherein $R_{11}$ and $R_{12}$ are as previously defined:
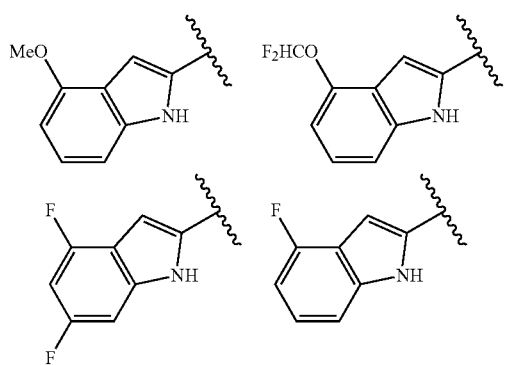
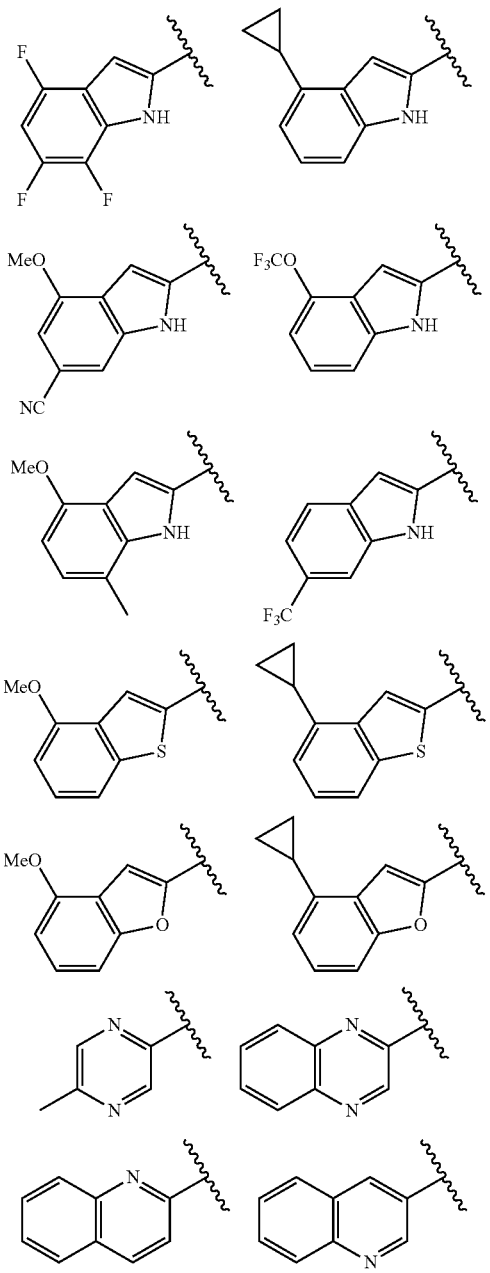
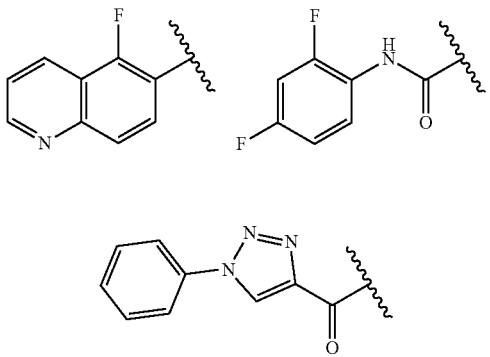

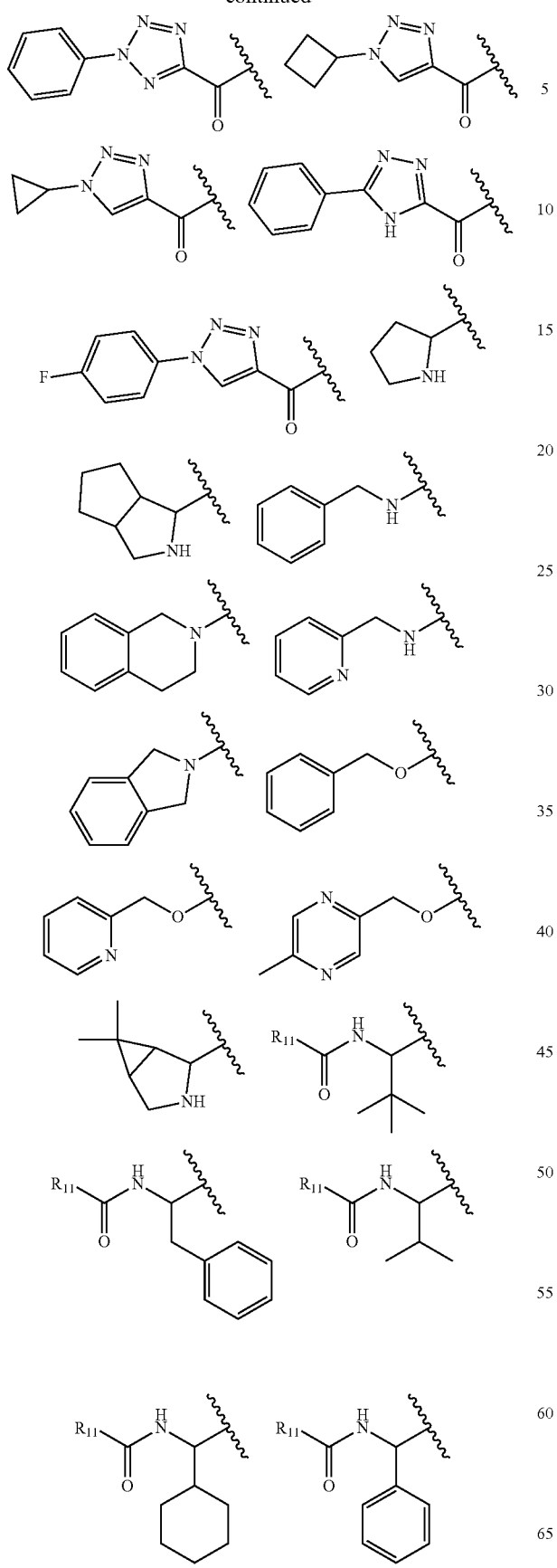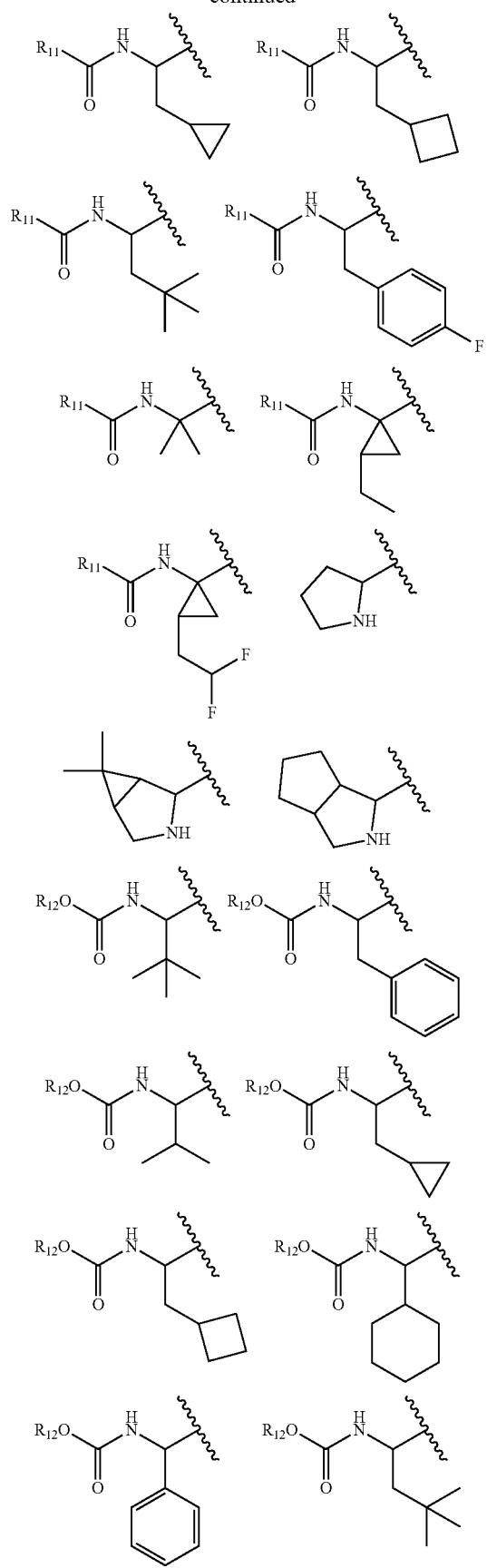

The present invention provides a pharmaceutical composition comprising a biologically active compound of the invention for the treatment of coronavirus in a mammal containing an amount of a coronavirus 3CL pro inhibitor that is effective in treating coronavirus and a pharmaceutically acceptable carrier or expedient.

The present invention provides a method of inhibiting the activity of a coronavirus 3CLpro, comprising contacting the coronavirus 3CLpro with an effective amount of a coronavirus 3CLpro inhibitor compound or agent.

The present invention also provides a method of targeting coronavirus inhibition as a means of treating indications caused by coronavirus related viral infections.

The present invention provides a method of treating or preventing a coronavirus infection in a subject in need thereof, comprising administering to the subject a therapeutically effective amount of a compound or a combination of compounds.

The present invention provides a method of treating or preventing a coronavirus infection in a subject in need thereof, further comprising administering to the subject an additional therapeutic agent selected from the group consisting of a coronavirus protease inhibitor, interferon, viral entry inhibitor, viral maturation inhibitor, inducer of cellular viral RNA sensor, therapeutic vaccine, and agents of distinct or unknown mechanism, and a combination thereof.

The present invention provides a method of reducing viral load in the subject to a greater extent compared to the administering of a compound selected from the group consisting of a coronavirus protease inhibitor, interferon, viral entry inhibitor, viral maturation inhibitor, distinct capsid assembly modulator, inducer of cellular viral RNA sensor, therapeutic vaccine, antiviral compounds of distinct or unknown mechanism, and combination thereof.

The present invention provides a method resulting in a lower incidence of viral mutation and/or viral resistance than the treatment with a compound selected from the group consisting of a coronavirus protease inhibitor, interferon, viral entry inhibitor, viral maturation inhibitor, distinct capsid assembly modulator, inducer of cellular viral RNA sensor, therapeutic vaccine, antiviral compounds of distinct or unknown mechanism, and combination thereof.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_2$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted. Preferably, as used herein, arylalkyl is aryl-$C_1$-$C_6$ alkyl, and heteroarylalkyl is heteroaryl-$C_1$-$C_6$ alkyl.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_2$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_2$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_2$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_2$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_2$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_2$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocycloalkyl, —$OCONH_2$, —OCONH—$C_2$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_2$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_2$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_2$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_2$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_2$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_2$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_2$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_2$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_2$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_2$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_2$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; acetyl, trifluoroacetyl, —CN; —OH; $NH_2$; $C_1$-$C_4$-alkylamino; di($C_1$-$C_4$-alkyl) amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (Lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-lgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, anthelmintic agents, antimalarial agents, antiprotozoal agents, antitubercuiosis agents, and antiviral agents, including those listed at https://www.drugs.com/drug-class/anti-infectives.html. In general, combination therapy is typically preferred over alternation therapy because it induces multiple simultaneous stresses on the virus.

Although the invention has been described with respect to various preferred embodiments, it is not intended to be limited thereto, but rather those skilled in the art will recognize that variations and modifications may be made therein which are within the spirit of the invention and the scope of the appended claims.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH or HOAc for acetic acid; ACN or MeCN or $CH_3CN$ for acetonitrile; $BF_3.OEt_2$ for boron trifluoride diethyl etherate; $Boc_2O$ for di-tert-butyl-dicarbonate; Boc for t-butoxycarbonyl; Bz for benzoyl; Bn for benzyl; t-BuOK for potassium tert-butoxide; Brine for sodium chloride solution in water; CbzCl or Cbz-Cl for benzyl chloroformate; CDI for carbonyldiimidazole; DCM or $CH_2Cl_2$ for dichloromethane; $CH_3$ for methyl; $(COCl)_2$ for oxalyl chloride; $Cl_2CHCN$ for dichloroacetonitrile; $Cs_2CO_3$ for cesium carbonate; CuCl for copper (I) chloride; CuI for copper (I) iodide; $CuSO_4$ for copper (II) sulfate; dba for dibenzylidene acetone; DBU for 1,8-diazabicyclo[5.4.0]-undec-7-ene; DCC for N,N'-dicyclohexylcarbodiimide; DCE for 1,2-dichloroethane; DIBAL-H for diisobutylaluminum hydride; DIPEA or $(i-Pr)_2EtN$ for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylaminopyridine; DME for 1,2-dimethoxyethane; DMF for N,N-dimethylformamide; DMSO for dimethyl sulfoxide; EDC for 1-ethyl-3-(3-dimethylaminopropyl)carbodiimide; EtOAc for ethyl acetate; EtOH for ethanol; $Et_2O$ for diethyl ether; $H_2$ for hydrogen, HATU for O-(7-azabenzotriazol-2-yl)-N,N,N',N',-tetramethyluronium Hexafluoro-phosphate; HCl for hydrogen chloride; $K_2CO_3$ for potassium carbonate; n-BuLi for n-butyl lithium; KHMDS for potassium bis(trimethylsilyl)amide; IBX for 2-iodoxybenzoic acid; In for indium; LDA for lithium diisopropylamide; Li for lithium;

LiBH₄ for lithium borohydride; LiBr for lithium bromide; LiHMDS for lithium bis(trimethylsilyl)amide; LiOH for lithium hydroxide; LiTMP for lithium 2,2,6,6-tetramethyl-piperidinate; MeOH for methanol; Mg for magnesium; MOM for methoxymethyl; Ms for mesyl or —SO₂—CH₃; NaHMDS for sodium bis(trimethylsilyl)amide; NaCl for sodium chloride; NaBH₄ for sodium borohydride; NaBH(OAc)₃ for sodium triacetoxyborohydride; NaH for sodium hydride; NaHCO₃ for sodium bicarbonate or sodium hydrogen carbonate; Na₂CO₃ sodium carbonate; NaOH for sodium hydroxide; Na₂SO₄ for sodium sulfate; NaHSO₃ for sodium bisulfite or sodium hydrogen sulfite; Na₂S₂O₃ for sodium thiosulfate; NBS for N-bromosuccinimide; NH₃ for ammonia; NH₄OH for ammonium hydroxide; NH₂NH₂ for hydrazine; NH₄Cl for ammonium chloride; Ni for nickel; NMM for N-methylmorpholine; n-PrOH for 1-propanol; OH for hydroxyl; OsO₄ for osmium tetroxide; OTf for triflate; PPA for polyphosphoric acid; PTSA or PTSOH for p-toluenesulfonic acid; PPTS for pyridinium p-toluenesulfonate; SiliaMetS DMT for the silica-bound equivalent of 2,4,6-trimercaptotriazine (trithiocyanuric acid, TMT); SO₃ for sulfur trioxide; TBAF for tetrabutylammonium fluoride; TEA or Et₃N or NEt₃ for triethylamine; TFA for trifluoroacetic acid; TFAA for trifluoroacetic anhydride; THF for tetrahydrofuran; T₃P for propylphosphonic anhydride; TPP or PPh₃ for triphenyl-phosphine; Tos or Ts for tosyl or —SO₂—C₆H₄CH₃; Ts₂O for tolylsulfonic anhydride or tosyl-anhydride; TsOH for p-tolylsulfonic acid; Pd for palladium; Pd/C for palladium on carbon; Ph for phenyl; Pd₂(dba)₃ for tris(diben-zylideneacetone) dipalladium (0); Pd(PPh₃)₄ for tetrakis(triphenylphosphine)-palladium (0); PdCl₂(PPh₃)₂ for trans-dichlorobis-(triphenylphosphine) palladium (II); PdCl₂(dppf) for [1,1'-bis(diphenylphosphino)ferrocene]palladium(II) dichloride; Pd(TFA)₂ for palladium(II) trifluoroacetate; for Pt for platinum; Rh for rhodium; rt for room temperature; Ru for ruthenium; TBS for tert-butyl dimethylsilyl; TMS for trimethylsilyl; or TMSCI for trimethylsilyl chloride; TMSOTf for trimethylsilyl trifluoromethanesulfonate; Zhan 1B cat. for dichloro [1,3-bis(2,4,6-trimethylphenyl)-2-imidazolidinylidene][[5-[(dimethylamino)sulfonyl]-2-(1-methylethoxy-O)phenyl]methylene-C]ruthenium(II).

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

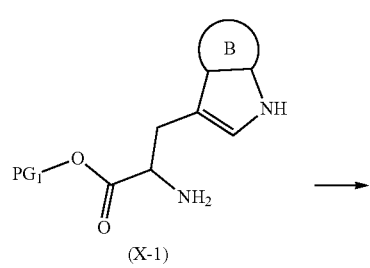

(X-1)

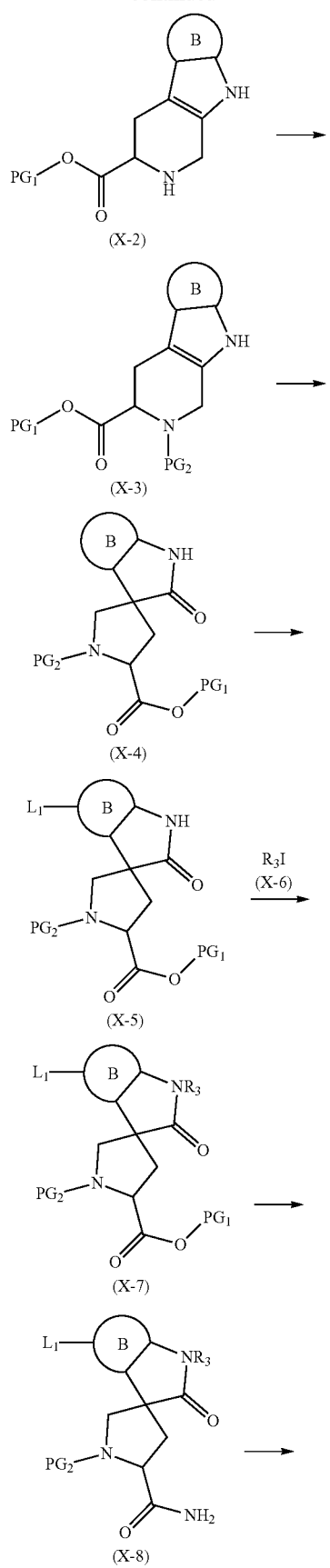

(X-2)

(X-3)

(X-4)

(X-5)

(X-7)

(X-8)

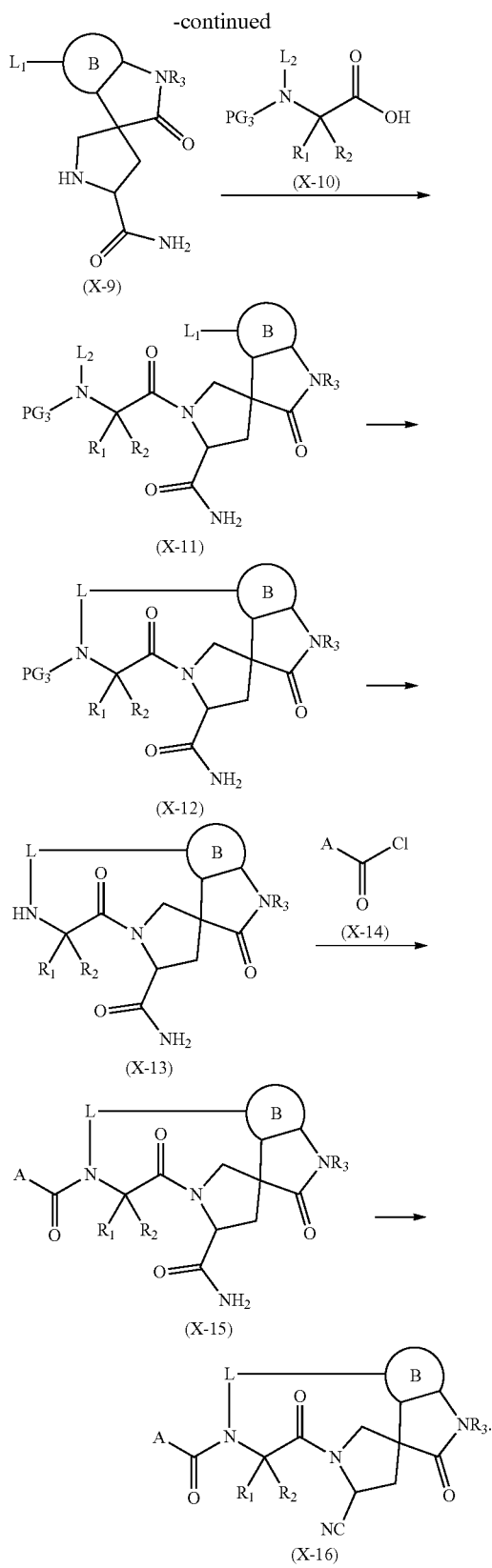

formaldehyde affords the cyclized amine (X-2), which was converted to (X-3) by using appropriate protecting group $PG_2$ (e.g. Boc). Treatment of (X-3) with NBS in solvents containing AcOH at low temperature provides the rearranged spiro-proline derivative (X-4). Examples of this sequence of transformation has been reported in literature (Pellegrini C. et al. "Synthesis of the Oxindole Alkaloid (−)-Horsfiline" Tetrahedron Asymmetry, 1994, vol. 5, No. 10, pp 1979-1992; Efremov, I. V. et al. "Discovery and Optimization of a Novel Spiropyrrolidine Inhibitor of β-Secretase (BACE1) through Fragment-Based Drug Design" Journal of Medicinal Chemistry, 2012, 55, 9069-9088). Direct functionalization of B ring in (X-4) (e.g., halogenation, Suzuki coupling, Heck reaction, transition-metal-catalyzed C—H functionalization, Friedel Crafts reaction, Minisci reaction, etc.) introduces the $L_1$ functional group to (X-5), wherein $L_1$ is the corresponding functionality to form the macrocycle linkage L that is as previously defined. Deprotonation of (X-5) using NaH followed by N-alkylation with (X-6), wherein $R_3$ is as previously defined, provided the ester (X-7). Treatment of ester (X-7) with $NH_3$ (e. g. ammonia in MeOH, $NH_4OH$, etc.) affords the amide compound (X-8), which is converted to amine compound (X-9) by removal of protecting group $PG_2$ (e.g., TFA, HCl, etc). Condensation of the amine (X-9) with acid (X-10) wherein $R_1$, and $R_2$ are as previously defined, $PG_3$ is the appropriate protecting group (e.g., Cbz or Boc.) and $L_2$ is the other corresponding functionality to form the macrocycle linkage L that is as previously defined, under amide coupling conditions (e.g., HATU, EDC, DCC, $T_3P$, etc) provides amide compound (X-11). Macrocyclization of (X-11) (e.g., ring closing metathesis, intramolecular Suzuki coupling, intramolecular click chemistry, macrolactamization, intramolecular Mitsunobu reaction, intramolecular Heck reaction, intramolecular $S_NAr$, intramolecular alkylation, etc.) ties up $L_1$ and $L_2$ functionality together to form macrocyclic compound (X-12), wherein L is as previously defined. These widely-used macrocyclization approaches have been reviewed in the literature (Marsault, E. et al. "Macrocycles Are Great Cycles: Applications, Opportunities, and Challenges of Synthetic Macrocycles in Drug Discovery" J. Med. Chem. 2011, 54, 7, 1961-2004). For example, the application of ring closing metathesis in synthesis of macrocyclic compounds has been reported in the literature (Yu, M. et al. "Ring-Closing Metathesis in Pharmaceutical Development: Fundamentals, Applications, and Future Directions" Org. Process Res. Dev. 2018, 22, 8, 918-946; Damalanka, V. C. et al. "Design, synthesis, and evaluation of a novel series of macrocyclic inhibitors of norovirus 3CL protease" European Journal of Medicinal Chemistry, Volume 127, 15 Feb. 2017, Pages 41-61). The application of intramolecular Suzuki coupling in synthesis of macrocyclic compounds has been reported in the literature (Li, H. et al. "Synthesis of Bis-Macrocyclic HCV Protease Inhibitor MK-6325 via Intramolecular $sp^2$-$sp^3$ Suzuki-Miyaura Coupling and Ring Closing Metathesis" Org. Lett. 2015, 17, 6, 1533-1536). The application of intramolecular click chemistry in synthesis of macrocyclic compounds has been reported in the literature (Weerawarna, P. M. et al. "Structure-based design and synthesis of triazole-based macrocyclic inhibitors of norovirus protease: Structural, biochemical, spectroscopic, and antiviral studies" European Journal of Medicinal Chemistry, Volume 119, 25 Aug. 2016, Pages 300-318). The application of macrolactamization in synthesis of macrocyclic compounds has been reported in the literature (Li, B. et al. "Exploratory Process Development of Lorlatinib" Org. Process Res. Dev.

Scheme 1 illustrates a general method to prepare the nitrile compound (X-16) of formula I from the amino ester compound (X-1), wherein B is as previously defined and $PG_1$ is $C_1$-$C_4$ alkyl or Bn. Treatment of amine (X-1) with 2018, 22, 1289-1293). PG₃ of (X-12) is cleaved by using the appropriate conditions (e.g., hydrogenation or HCl) to afford amine compound (X-13), which is further coupled with acid chloride (X-14) to form the compound (X-15), where A is as previously defined. Amide (X-15) is converted to the nitrile compound (X-16) under dehydration conditions (e.g. TFAA/Et₃N, Pd(TFA)₂/Cl₂CHCN or T₃P).

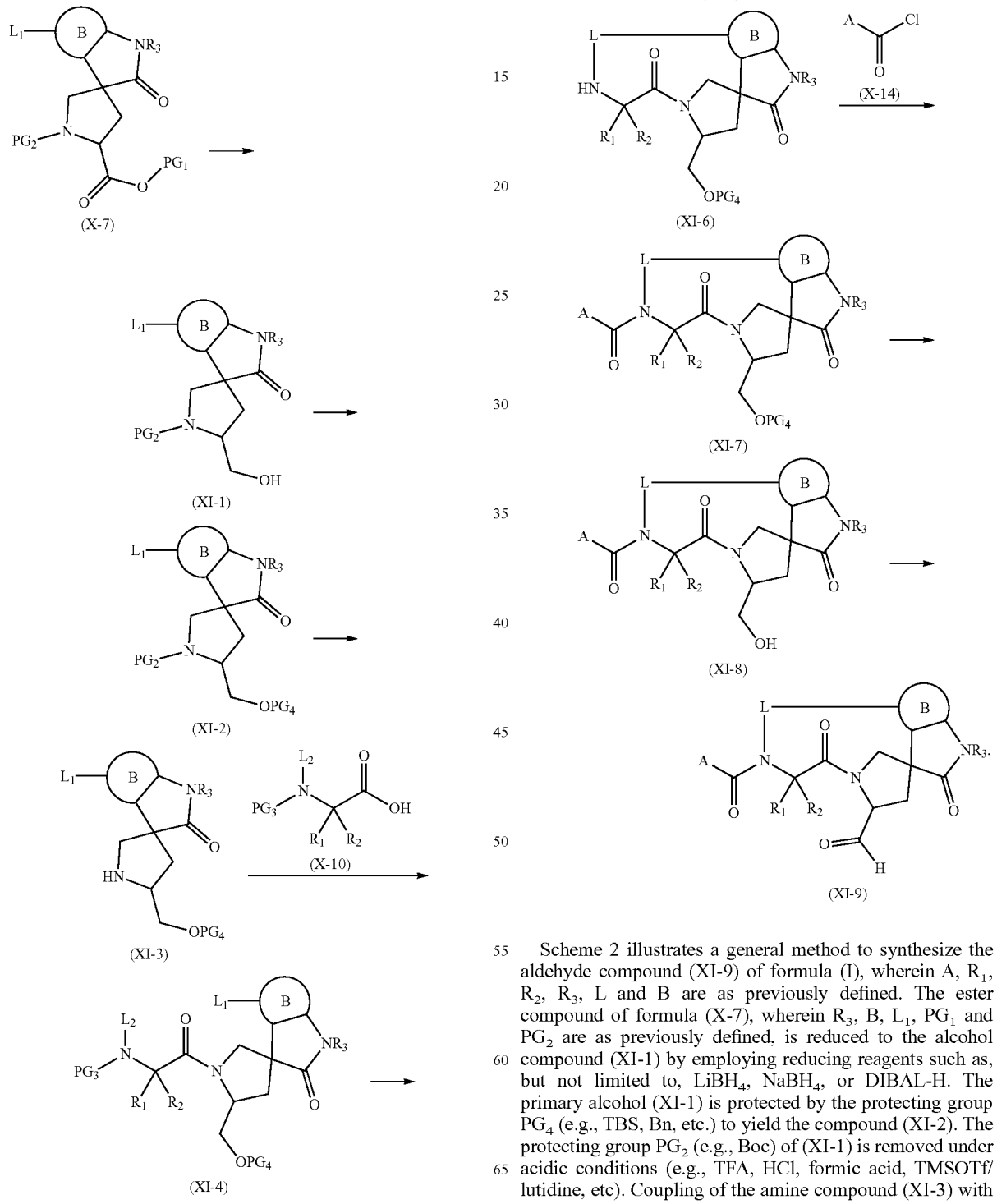

Scheme 2 illustrates a general method to synthesize the aldehyde compound (XI-9) of formula (I), wherein A, R₁, R₂, R₃, L and B are as previously defined. The ester compound of formula (X-7), wherein R₃, B, L₁, PG₁ and PG₂ are as previously defined, is reduced to the alcohol compound (XI-1) by employing reducing reagents such as, but not limited to, LiBH₄, NaBH₄, or DIBAL-H. The primary alcohol (XI-1) is protected by the protecting group PG₄ (e.g., TBS, Bn, etc.) to yield the compound (XI-2). The protecting group PG₂ (e.g., Boc) of (XI-1) is removed under acidic conditions (e.g., TFA, HCl, formic acid, TMSOTf/lutidine, etc). Coupling of the amine compound (XI-3) with the acid compound (X-8) wherein PG₃, L₂, R₁, and R₂ are as previously defined, under amide coupling conditions (e.g., HATU, EDC, DCC, or T₃P) provides compound (XI-4). Similar to the approaches in Scheme 1, macrocyclization of (XI-4) (e.g., ring closing metathesis, intramolecular Suzuki coupling, intramolecular click chemistry, macrolactamization, intramolecular Mitsunobu reaction, intramolecular Heck reaction, intramolecular $S_NAr$, intramolecular alkylation, etc.) ties up $L_1$ and $L_2$ functionality together to form macrocyclic compound (XI-5), wherein L is as previously defined. $PG_3$ is cleaved under the appropriate conditions (e.g., hydrogenation or HCl) to afford amine compound (XI-6), which is further coupled with acid chloride (X-12) to form the compound (XI-7), where A is as previously defined. $PG_4$ was removed (e.g., HCl, TBAF, hydrogenation, etc.) to give primary alcohol compound (XI-8). Oxidation of the alcohol compound (XI-8) (e.g., Dess-Martin periodinane, IBX, $SO_3$-pyridine/DMSO/$Et_3N$, etc.) produces the aldehyde compound (XI-9).

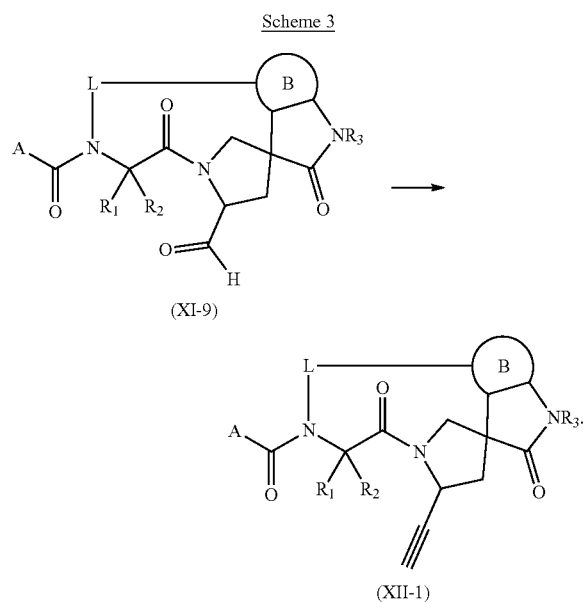

Scheme 3 illustrates a general method to synthesize the alkyne compound (XII-1) of formula (I), wherein A, $R_1$, $R_2$, $R_3$, L and B are as previously defined. The alkyne compound (XII-1) is prepared by Seyferth-Gilbert homologation or Corey-Fuchs reaction from the aldehyde compound (XI-9), wherein A, $R_1$, $R_2$, $R_3$, L and B are as previously defined.

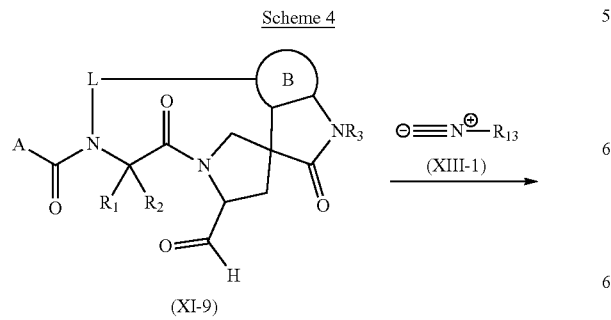

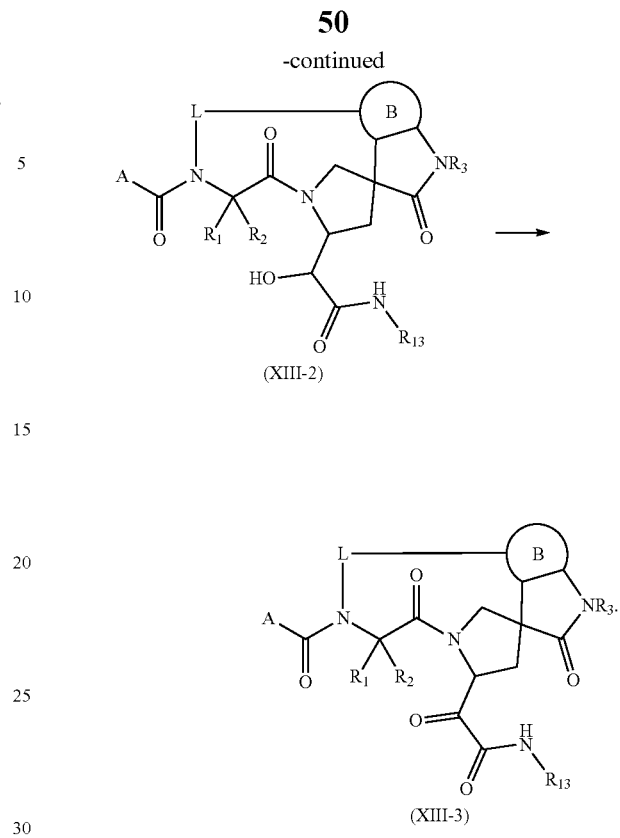

Scheme 4 illustrates a general method to synthesize the α-ketoamide compound (XIII-3) of formula (I), wherein A, $R_1$, $R_2$, $R_3$, $R_{13}$, L and B are as previously defined. Treatment of the aldehyde compound of formula (XI-9), wherein A, $R_1$, $R_2$, $R_3$ and B are as previously defined, with isonitrile compound (XIII-1), wherein $R_{13}$ is as previously defined, affords α-hydroxylamide (XIII-2). Oxidation of compound (XIII-2) with appropriate oxidants such as Dess-Martin periodinane, $(COCl)_2$/DMSO/$Et_3N$, PCC, $SO_3$-pyridine/DMSO/$Et_3N$, affords α-ketoamide compound (XIII-3).

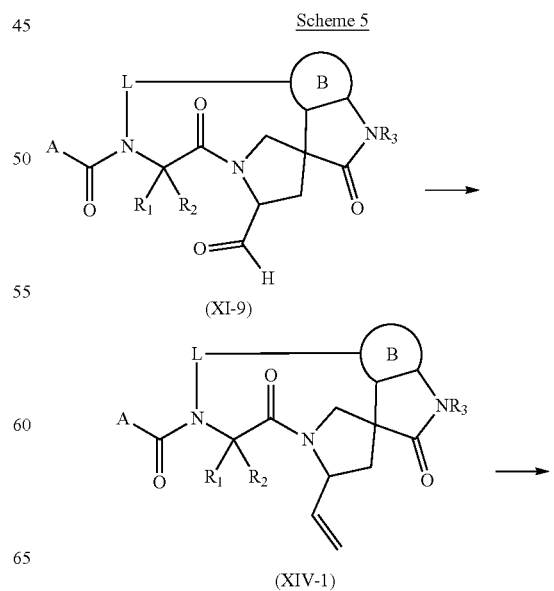

51

-continued

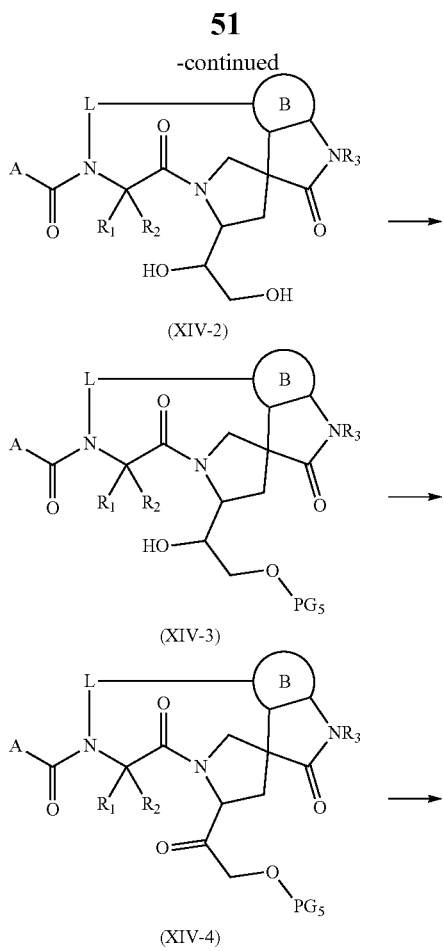

(XIV-2)

(XIV-3)

(XIV-4)

52

-continued

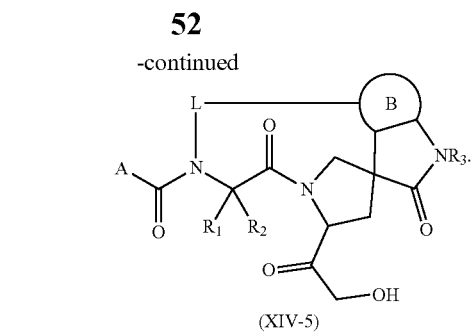

(XIV-5)

Scheme 5 illustrates a general method to synthesize the hydroxyketone compound (XIV-5) of formula (I). The Wittig reaction of the aldehyde (XI-9), wherein A, $R_1$, $R_2$, $R_3$, L and B are as previously defined, provides the alkene (XIV-1). Dihydroxylation of the alkene (XIV-1) using Upjohn Dihydroxylation ($OsO_4$, NMO) affords the diol (XIV-2), whose primary alcohol is selectively protected with an appropriate protecting group $PG_5$ (e.g., TBS) to form the alcohol (XIV-3). Oxidation of the alcohol (XIV-3) with appropriate oxidants (e.g., Dess-Martin periodinane, $(COCl)_2$/DMSO/$Et_3N$, PCC, or $SO_3$-pyridine/DMSO/$Et_3N$) affords the ketone (XIV-4). The removal of $PG_5$ using appropriate conditions (e.g., TBAF) provides the hydroxyketone compound (XIV-5).

EXAMPLES

Example 1

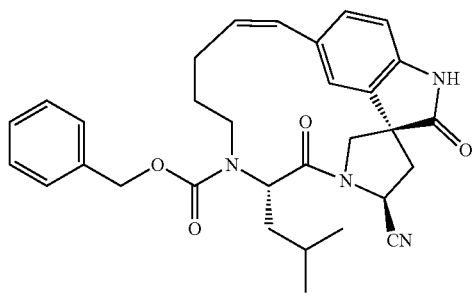

Example 1

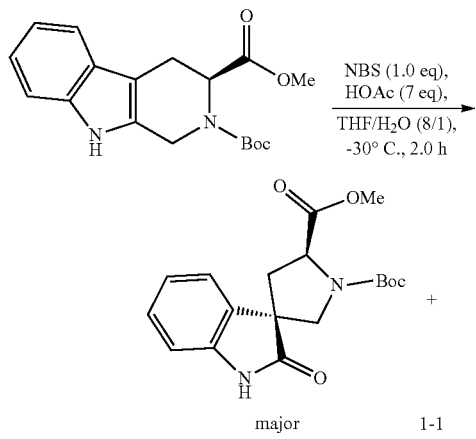

major       1-1

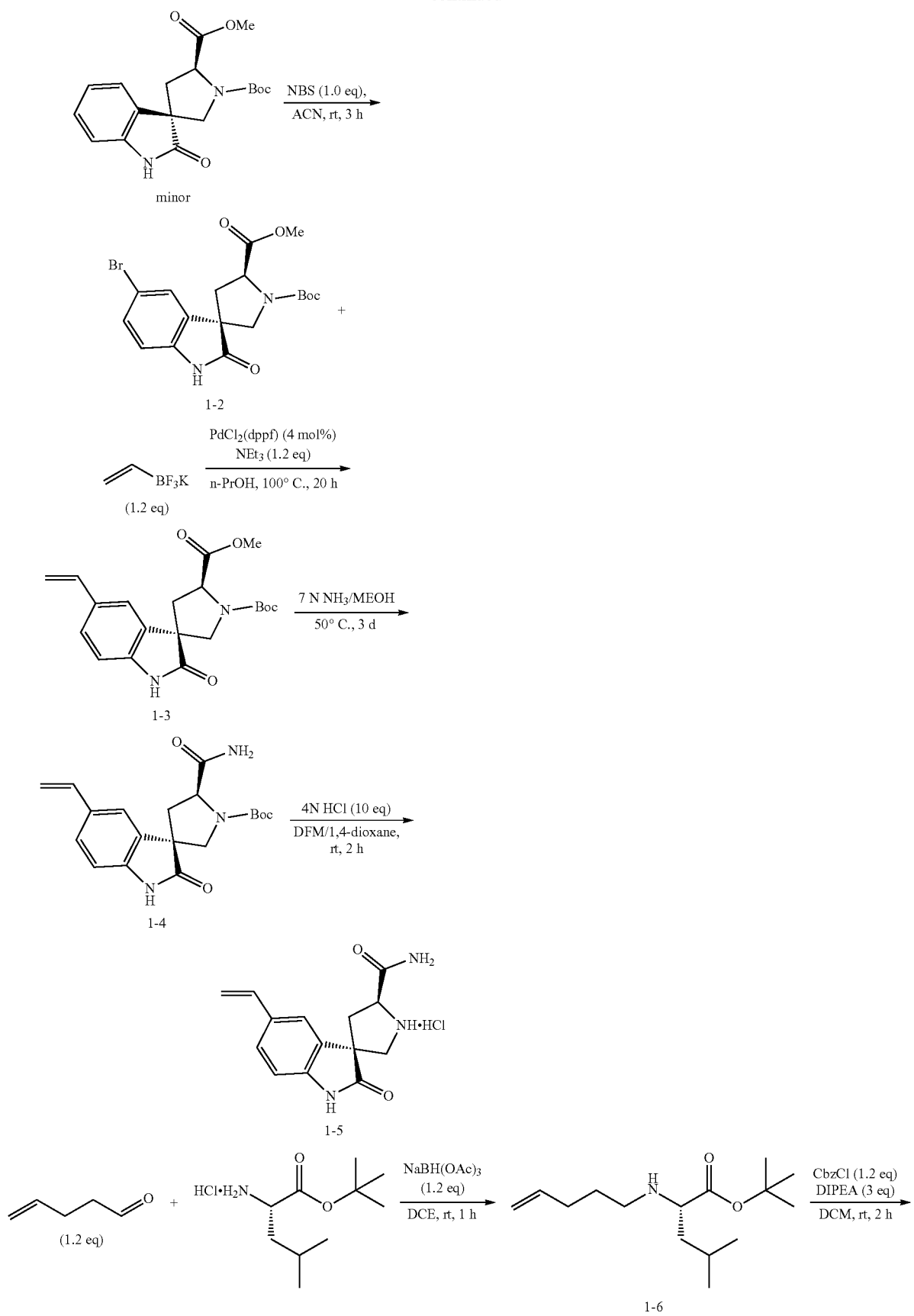

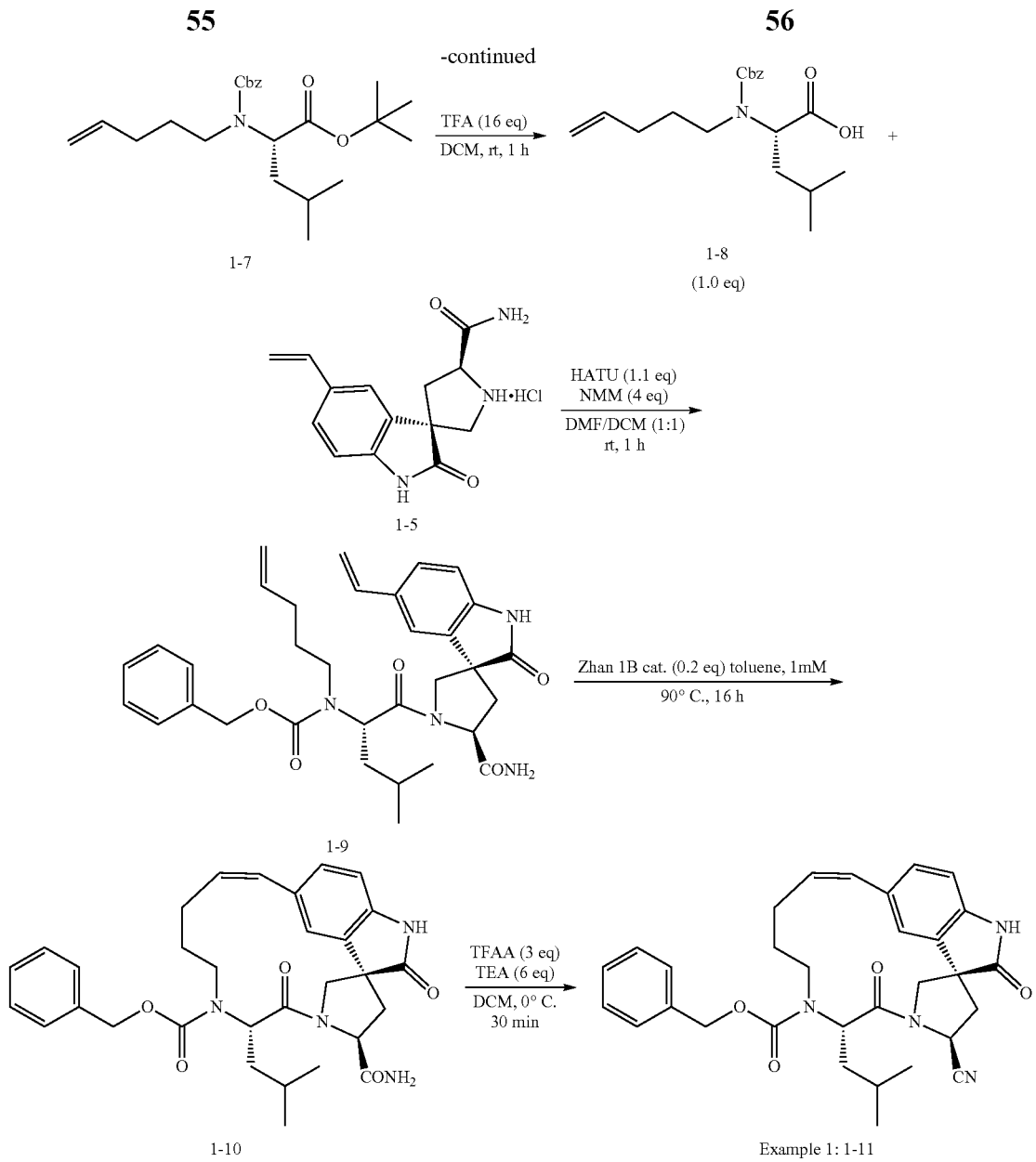

Step 1-1: To a clear colorless solution of 2-(tert-butyl) 3-methyl (S)-1,3,4,9-tetrahydro-2H-pyrido[3,4-b]indole-2,3-dicarboxylate (45.00 g, 136 mmol) in THF (720 ml) in a three neck 2000 mL flask at 0° C. (internal temperature) was added water (90 ml) in one portion. Acetic acid (54.6 ml, 953 mmol) was added at 0° C. The cloudy mixture was cooled to −30° C. (internal temperature). It became a milky solution. A solution of NBS (24.24 g, 136 mmol) in THF/H$_2$O (8/1, 207 ml) was added dropwise over 30 min while maintaining the internal temperature below −30° C. The milky mixture became a yellow cloudy solution and was stirred at −30° C. (internal temperature) for 1.0 h. TLC (CH/EtOAc 1/1) showed no SM. The cloudy yellow solution was allowed to warm up to −20° C. and poured portionwise into a mixture of potassium carbonate (65.9 g, 477 mmol) in cold water (~300 ml), saturated NaHCO$_3$ solution (~400 ml) and EtOAc (300 ml) with stirring. The mixture was further diluted with EtOAc (500 ml). The aqueous layer was extracted with EtOAc (*1). The combined organic layers were washed with brine (*1), dried over Na$_2$SO$_4$ (s), filtered and concentrated to afford crude product as a light yellow sticky oil (56.0 g). The crude product was dissolved in DCM (60 ml) and filtered through a 330 g silica gel column (MTBE/Cyclohexane) to afford the mixture of major and minor diasteromers as an off-white foam (48.20 g, 102%, dr 10/1).

$^1$H NMR (400 MHz, DMSO-d$_6$) δ 10.66 (d, J=1.9 Hz, 1H), 7.23 (td, J=7.7, 1.2 Hz, 1H), 7.07 (ddd, J=15.0, 7.5, 1.3 Hz, 1H), 6.99 (tdd, J=7.5, 2.7, 1.0 Hz, 1H), 6.93-6.87 (m, 1H), 4.68-4.55 (m, 1H), 3.71 (d, J=12.5 Hz, 3H), 3.61-3.46 (m, 2H), 2.38 (ddd, J=12.8, 7.9, 1.5 Hz, 1H), 2.25 (ddd, J=18.4, 12.8, 9.0 Hz, 1H), 1.44-1.32 (m, 9H). ESI MS m/z=369.12 [M+Na]$^+$.

Step 1-2: A clear colorless solution of the mixture of compounds from Step 1-1 (3.94 g, 11.4 mmol, dr 10/1) in acetonitrile (40 mL) was treated with NBS (2.23 g, 12.5 mmol) in three portions at room temperature. The reaction was stirred at room temperature for 3 h. It became a light yellow solution. LCMS showed no SM. The reaction was quenched with aqueous $Na_2S_2O_3$. The mixture was allowed to stir at room temperature for additional 30 min. The cloudy mixture was further diluted with EtOAc (80 mL). The aqueous layer was extracted with EtOAc twice. The combined organic layers were washed with brine, dried over $Na_2SO_4$, filtered and concentrated to afford crude product as an off-white solid. The crude was dissolved in DCM (10 mL) and filtered through a 8 g silica gel pad (MTBE) to afford the desired product (dr 10/1) as a white solid. The product was treated with MTBE/hexane (2:1) (30 mL). The mixture was sonicated over 10 min to form a milky suspension, which was filtered and washed with MTBE/hexane (2:1) to give the desired product as a white solid (4.23 g, 10.0 mmol, dr >100/1).

$^1$H NMR (400 MHz, DMSO-$d_6$) δ 10.78 (s, 1H), 7.42 (dd, J=8.3, 2.0 Hz, 1H), 7.20 (dd, J=18.7, 2.0 Hz, 1H), 6.86 (d, J=8.3 Hz, 1H), 4.68 (dt, J=13.0, 8.4 Hz, 1H), 3.71 (d, J=12.0 Hz, 3H), 3.66-3.59 (m, 1H), 3.47 (dd, J=10.7, 7.4 Hz, 1H), 2.24 (ddd, J=18.4, 12.9, 8.7 Hz, 1H), 1.40 (d, J=5.7 Hz, 6H). ESI MS m/z=422.74, 424.64 [M−H]$^-$.

Step 1-3: A clear colorless solution of the compound from Step 1-2 (4.2 g, 9.9 mmol) in n-PrOH (35 mL) was treated with triethylamine (1.7 mL, 11.9 mmol), potassium vinyltrifluoroborate (1.6 g, 11.9 mmol) and PdCl$_2$(dppf) (290 mg, 0.4 mmol) under $N_2$. The mixture was degassed and backfilled with $N_2$ (*3). The resulting orange suspension was bubbled with $N_2$ for 10 min. The reaction was warmed to 100° C. and stirred for 20 h. It became dark red/brown mixture. TLC (CH/EtOAc 2:1) showed no SM. The reaction was diluted with ethyl acetate (100 mL) and quenched with aqueous $NaHCO_3$. The aqueous layer was extracted with ethyl acetate (*2). The combined organic layers were washed with water and brine, dried over $Na_2SO_4$, filtered and concentrated in vacuo. The crude was redissolved in ethyl acetate (20 mL) and treated with SiliaMetS DMT (8 g) as a metal scavenger. The mixture was stirred at room temperature for 16 h, then filtered, rinsed with MTBE/CH (2:1) (200 mL) and concentrated in vacuo. The brownish crude was redissolved in ethyl acetate (20 mL), treated with activated charcoal and warmed to 60° C. for 1 h. The mixture was filtered after cooling to give a light yellow solution, which was further concentrated in vacuo to give the desired product (3.3 g, 8.7 mmol, 90%) as an off-white foam.

$^1$H NMR (400 MHz, DMSO-$d_6$) δ 10.72 (s, 1H), 7.38-7.30 (m, 1H), 7.22-7.14 (m, 1H), 6.87 (d, J=8.0 Hz, 1H), 6.68 (ddd, J=18.2, 10.9, 7.5 Hz, 1H), 5.65 (dd, J=17.6, 10.4 Hz, 1H), 5.13 (dd, J=11.0, 5.7 Hz, 1H), 4.76-4.65 (m, 1H), 3.71 (d, J=12.0 Hz, 3H), 3.65-3.58 (m, 1H), 3.50 (t, J=10.8 Hz, 1H), 2.44 (dd, J=12.9, 8.1 Hz, 1H), 2.26 (ddd, J=18.9, 12.8, 8.8 Hz, 1H), 1.43-1.36 (m, 9H). ESI MS m/z=370.79 [M−H]$^-$.

Step 1-4: A clear light yellow solution of the compound from Step 1-3 (3.3 g, 8.9 mmol) in 7 N ammonia in MeOH (80 ml, 560 mmol) was stirred at 50° C. in a sealed pressure vessel over the weekend (3 d). LCMS showed no SM. The mixture was allowed to cool down and concentrated in vacuo to give a yellow gel-like solid. The solid was redissolved in 30 mL MeOH/dioxane (1:10), co-evaporated in vacuo to give a light yellow solid. The crude was dried under high vacuum for 1 h, then mashed to small pieces and dried under high vacuum overnight to give a light yellow powder. The powder was washed with 10 mL DCM/MTBE (1:2), sonicated and filtered to give the desired product (3.05 g, 8.5 mmol, 96%) as an off-white solid.

$^1$H NMR (400 MHz, DMSO-$d_6$) δ 10.73 (s, 1H), 7.51 (s, 1H), 7.37-7.29 (m, 1H), 7.17-6.98 (m, 2H), 6.88 (d, J=8.0 Hz, 1H), 6.66 (dt, J=17.5, 10.9 Hz, 1H), 5.58 (dd, J=17.5, 11.8 Hz, 1H), 5.14 (t, J=10.3 Hz, 1H), 4.50 (q, J=8.5, 7.9 Hz, 1H), 3.57 (s, 3H), 3.50 (t, J=10.3 Hz, 1H), 2.31-2.14 (m, 2H), 1.80 (d, J=13.8 Hz, 1H), 1.39 (d, J=25.4 Hz, 9H). ESI MS m/z=355.79 [M−H]$^-$.

Step 1-5: To a clear solution of the compound from Step 1-4 (1.15 g, 3.22 mmol) in DMF (2 ml) at rt was added 4 M HCl in 1,4-dioxane (8 ml, 32 mmol). The resulting clear yellow solution was stirred at rt for 2 h. The mixture was concentrated by rotavapor. The residual clear DMF solution was poured into DCM (150 ml) with stirring to get a white slurry. The mixture was sonicated to form a cloudy suspension. The solid was collected by filtration, washing with DCM, and then MTBE. The solid was dried under vacuum to afford the desired product as an off-white powder (862 mg, 2.93 mmol, 91%). 1 g of the above product was mixed with DMF (2 ml) and heated with a heat gun to get an almost clear solution. Solid started to appear while heating. The mixture was allowed to cool down to rt. The solid was collected by filtration, washing with DMF (0.2 ml), DCM and MTBE. The solid was dried under vacuum to afford the desired product as a white solid (771 mg).

$^1$H NMR (500 MHz, DMSO-$d_6$) δ 10.84 (d, J=3.0 Hz, 1H), 9.03 (s, 1H), 8.13-7.95 (m, 1H), 7.85-7.70 (m, 2H), 7.39 (td, J=8.2, 1.8 Hz, 1H), 6.94-6.81 (m, 1H), 5.31 (qd, J=6.8, 2.0 Hz, 1H), 4.66 (dt, J=11.4, 6.2 Hz, 1H), 2.57-2.52 (m, 1H), 2.25 (ddd, J=12.7, 10.6, 1.5 Hz, 1H), 1.84 (dd, J=6.8, 1.7 Hz, 2H). ESI MS m/z=257.77 [M−H]$^-$.

Step 1-6: A solution of tert-butyl L-leucinate hydrochloride (2.1 g, 9.39 mmol) and pent-4-enal (1 g, 11.89 mmol) in DCE (30 ml) was treated with sodium triacetoxyborohydride (2.7 g, 12.74 mmol) at room temperature. The reaction was stirred at room temperature for 2 h and then quenched with a saturated solution of sodium bicarbonate. The aqueous layer was extracted with dichloromethane over 3 times. The combined organic layer was dried over sodium sulfate, filtered and concentrated in vacuo. The crude was added to a 80 g silica gel column and eluted by MTBE/cyclohexane from 0% to 100% to give the desired product (1.96 g, 7.67 mmol, 82% yield) as a pale yellow oil.

ESI MS m/z=255.84 [M+H]$^+$.

Step 1-7: A solution of the compound from Step 1-6 (1.96 g, 7.67 mmol) in $CH_2Cl_2$ (30 ml) was treated with DIPEA (4.02 ml, 23.02 mmol) and Cbz-Cl (1.315 ml, 9.21 mmol) at 0° C. The reaction was warmed to room temperature and stirred for 2 h. The reaction was quenched with a saturated solution of sodium bicarbonate. The aqueous layer was extracted with dichloromethane over 3 times. The combined organic layer was dried over sodium sulfate, filtered and concentrated in vacuo. The crude was added to a 80 g silica gel column and eluted by MTBE/cyclohexane from 0% to 100% to give the desired product (2.64 g, 6.78 mmol, 88% yield) as a colorless oil.

$^1$H NMR (400 MHz, Chloroform-d) δ 7.34 (t, J=4.8 Hz, 5H), 5.89-5.67 (m, 1H), 5.28-4.88 (m, 4H), 4.54-4.21 (m, 1H), 3.47-3.28 (m, 1H), 3.07-2.91 (m, 1H), 2.04 (dt, J=22.7, 7.2 Hz, 2H), 1.81-1.47 (m, 8H), 1.39 (d, J=10.5 Hz, 11H), 1.00-0.83 (m, 6H). ESI MS m/z=411.93 [M+Na]$^+$.

Step 1-8: A solution of the compound from Step 1-7 (650 mg, 1.669 mmol) in $CH_2Cl_2$ (2 ml) was treated with TFA (2 ml, 26.0 mmol) at room temperature. The reaction was stirred at room temperature for 1 h. The mixture was concentrated in vacuo, then co-evaporated with toluene twice. The crude was dried under high vacuum to give the desired product (547 mg, 1.641 mmol, 98% yield) as an off-white syrup.

$^1$H NMR (400 MHz, Chloroform-d) δ 7.34 (d, J=8.5 Hz, 5H), 5.89-5.63 (m, 1H), 5.29-4.83 (m, 7H), 4.42 (t, J=7.8 Hz, 1H), 3.41 (d, J=20.1 Hz, 1H), 3.06 (ddd, J=15.2, 10.2, 5.6 Hz, 1H), 2.22-1.54 (m, 8H), 1.06-0.79 (m, 6H). ESI MS m/z=331.85 [M−H]$^-$.

Step 1-9: A solution of the compound from Step 1-5 (335 mg, 1.140 mmol) and the compound from Step 1-8 (375 mg, 1.125 mmol) in DMF (2 ml) and CH$_2$Cl$_2$ (2 ml) was treated with N-methylmorpholine (500 μl, 4.55 mmol) and HATU (470 mg, 1.236 mmol). The reaction was stirred at rom temperature for 1 h. The reaction was quenched with a saturated solution of sodium bicarbonate and diluted with ethyl acetate. The organic layer was washed with water and brine twice, dried over sodium sulfate, filtered and concentrated in vacuo. The crude was added to a 12 g silica gel column and eluted by acetone/cyclohexane from 0% to 100% to give the desired product (230 mg, 0.402 mmol, 35% yield) as a white solid.

$^1$H NMR (500 MHz, DMSO-d$_6$) δ 10.78 (d, J=17.6 Hz, 1H), 7.50 (s, 1H), 7.43-7.15 (m, 3H), 7.15-6.83 (m, 4H), 6.58 (dd, J=17.4, 11.0 Hz, 1H), 5.87-5.62 (m, 1H), 5.54 (d, J=17.6 Hz, 1H), 5.19-4.74 (m, 4H), 4.74-4.50 (m, 2H), 3.93 (d, J=10.3 Hz, 1H), 3.74 (d, J=10.2 Hz, 1H), 3.67-3.48 (m, 1H), 3.13 (tt, J=11.9, 6.8 Hz, 2H), 2.35-2.07 (m, 2H), 2.03-1.85 (m, 2H), 1.72-1.34 (m, 4H), 0.95-0.67 (m, 6H). ESI MS m/z=571.07 [M−H]$^-$.

Step 1-10: A solution of the compound from Step 1-9 (163 mg, 0.285 mmol) in toluene (250 ml) was treated with Zhan 1B cat. (41 mg, 0.056 mmol). The mixture was degassed by freeze-pump-thaw and refilled with N$_2$ over 3 times. The reaction was warmed to 90° C. and stirred overnight. The reaction was concentrated in vacuo. The crude was added to a 12 g silica gel column and eluted by acetone/cyclohexane from 0% to 100% to give the desired product (163 mg, 0.285 mmol, 86% yield) as a brownish foam.

$^1$H NMR (500 MHz, Methanol-d$_4$) δ 7.40-6.82 (m, 11H), 6.48 (t, J=10.4 Hz, 1H), 5.67 (dtd, J=39.4, 11.0, 5.9 Hz, 1H), 5.30 (d, J=11.8 Hz, 1H), 5.20 (t, J=7.5 Hz, 1H), 5.04-4.89 (m, 2H), 4.78-4.61 (m, 2H), 4.11-4.00 (m, 1H), 3.78 (d, J=10.0 Hz, 1H), 3.72-3.53 (m, 2H), 3.37 (dd, J=14.2, 3.4 Hz, 1H), 2.51-2.22 (m, 5H), 2.12-1.86 (m, 2H), 1.84-1.30 (m, 8H), 1.00-0.78 (m, 6H). ESI MS m/z=543.06 [M−H]$^-$.

Step 1-11: A solution of the compound from Step 1-10 (30 mg, 0.055 mmol) in CH$_2$Cl$_2$ (0.4 ml) was treated with TEA (60 μl, 0.430 mmol) and TFAA (30 μl, 0.212 mmol) dropwise at 0° C. The reaction was stirred at 0° C. for 2 h and quenched with a saturated solution of sodium bicarbonate. The mixture was stirred at room temperature for 30 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 1 (21 mg, 0.040 mmol, 72% yield) as a white solid.

$^1$H NMR (400 MHz, Chloroform-d) δ 8.14 (d, J=48.9 Hz, 1H), 7.25-7.07 (m, 4H), 7.07-7.00 (m, 1H), 6.94 (dd, J=8.0, 3.5 Hz, 1H), 6.75 (d, J=1.6 Hz, 1H), 6.44 (dd, J=11.1, 4.0 Hz, 1H), 5.66 (td, J=11.0, 5.8 Hz, 1H), 5.25-5.10 (m, 1H), 5.02 (d, J=12.1 Hz, 1H), 4.95-4.79 (m, 2H), 4.23-4.03 (m, 1H), 3.86-3.67 (m, 1H), 3.62 (ddd, J=15.3, 12.6, 2.6 Hz, 1H), 3.45 (dt, J=14.2, 3.4 Hz, 1H), 2.88 (dd, J=12.8, 10.6 Hz, 1H), 2.58-2.40 (m, 1H), 2.16-1.86 (m, 3H), 1.84-1.38 (m, 8H), 1.03-0.75 (m, 10H).
ESI MS m/z=525.05 [M−H]$^-$.

Example 2

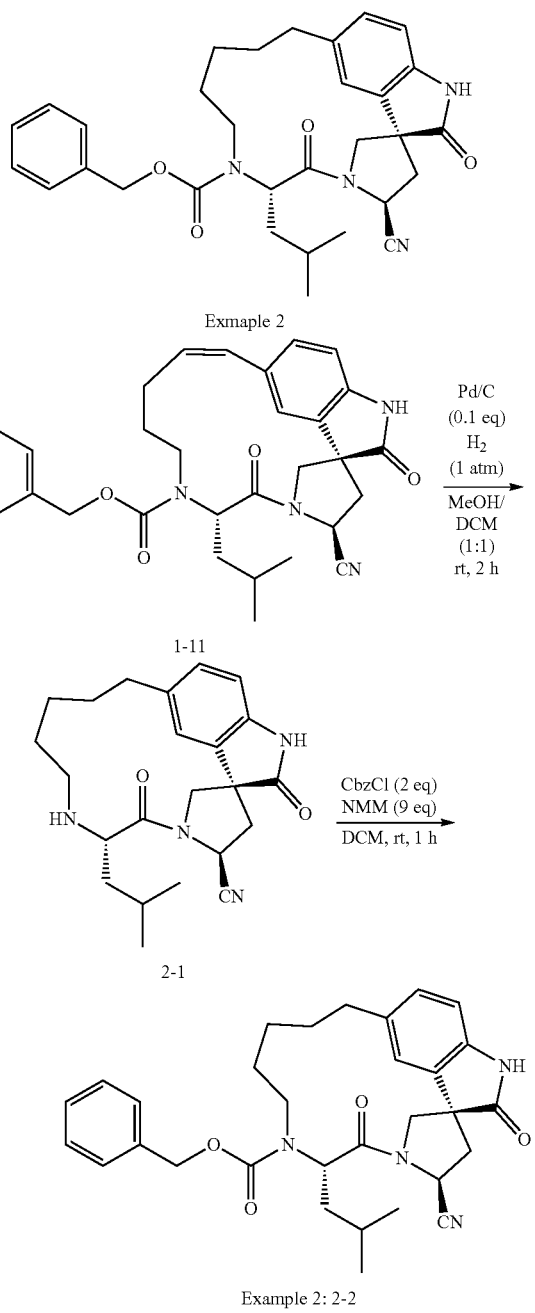

Exmaple 2

Example 2: 2-2

Step 2-1: A solution of the compound from Step 1-11 (19 mg, 0.036 mmol) in MeOH (0.3 ml) and CH$_2$Cl$_2$ (0.3 ml) was treated with Pd—C (4 mg, 3.76 μmol) under H$_2$. The mixture was bubbled with H$_2$ for 5 min. The reaction was stirred at room temperature for 2 h. The mixture was filtered through celite and concentrated in vacuo to give the desired product (12 mg, 0.030 mmol, 84% yield) as an off-white solid.

ESI MS m/z=395.09 [M+H]$^+$.

Step 2-2: A solution of the compound from Step 2-1 (12 mg, 0.030 mmol) was treated with N-methylmorpholine (30 μl, 0.273 mmol) and Cbz-Cl (20 μl, 0.140 mmol) dropwise at room temperature. The reaction was stirred at room temperature for 1 h and then quenched with a saturated solution of sodium bicarbonate. The aqueous layer was extracted with ethyl acetate over 3 times. The combined organic layer was dried over sodium sulfate, filtered and concentrated in vacuo. The crude was added to a 4 g silica gel column and eluted by ethyl acetate/cyclohexane from 0% to 100% to give Example 2 (9 mg, 0.017 mmol, 56% yield) as a white solid.

¹H NMR (400 MHz, Chloroform-d) δ 7.91 (s, 1H), 7.28 (d, J=1.8 Hz, 2H), 7.13 (d, J=7.0 Hz, 2H), 7.02 (d, J=8.0 Hz, 1H), 6.88 (d, J=8.0 Hz, 1H), 6.60 (s, 1H), 5.09 (dd, J=10.4, 8.0 Hz, 2H), 4.94 (s, 1H), 4.19-3.88 (m, 2H), 3.88-3.63 (m, 1H), 3.60-3.40 (m, 2H), 3.33 (d, J=14.2 Hz, 1H), 2.88 (s, 1H), 2.60-2.46 (m, 2H), 2.18 (d, J=2.5 Hz, 1H), 1.87 (dt, J=14.1, 7.6 Hz, 3H), 1.42 (h, J=7.0 Hz, 7H), 1.26 (s, 5H), 0.91 (d, J=15.8 Hz, 7H), 0.71 (s, 1H). ESI MS m/z=527.02 [M−H]⁻.

Example 3

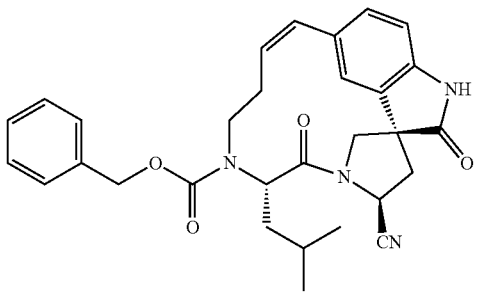

Example 3

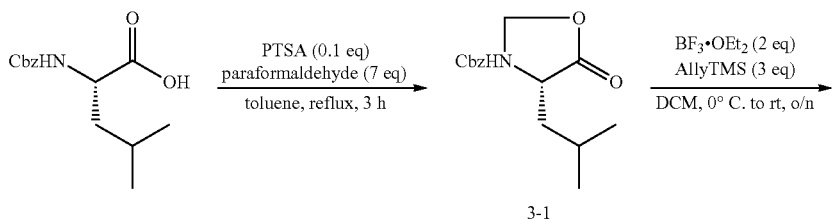

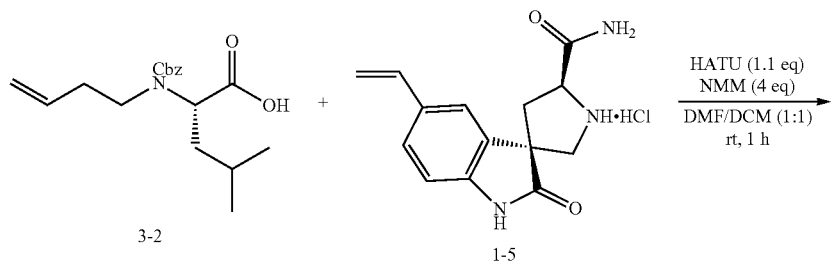

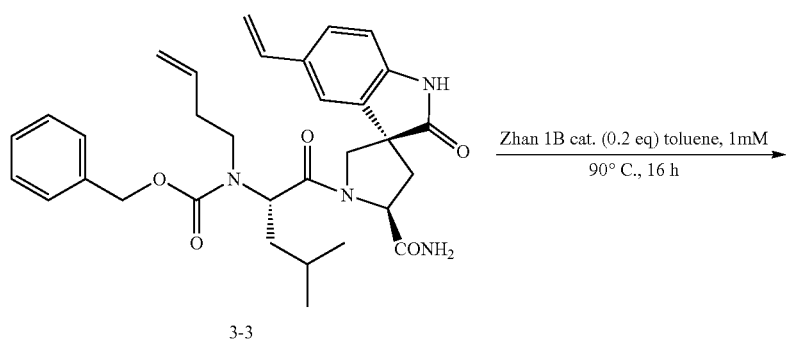

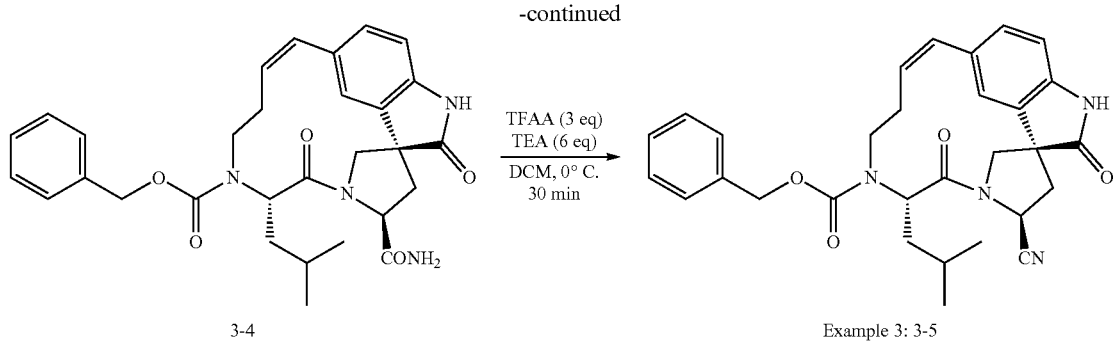

Step 3-1: A solution of ((benzyloxy)carbonyl)-L-leucine (2.24 g, 8.44 mmol) in toluene (150 ml) was treated with paraformaldehyde (1.8 g, 59.9 mmol) and PTSOH (168 mg, 0.883 mmol). The suspension was warmed to 110° C. and refluxed under Dean-Stark conditions for 3 h. The reaction was quenched with a saturated solution of sodium bicarbonate. The aqueous layer was extracted with ethyl acetate over 3 times. The combined organic layer was dried over sodium sulfate, filtered and concentrated in vacuo. The crude was added to a 40 g silica gel column and eluted by ethyl acetate/cyclohexane from 0% to 30% over 20 min to give the desired product (2 g, 7.21 mmol, 85% yield) as a colorless oil.

$^1$H NMR (500 MHz, Chloroform-d) δ 7.37 (qd, J=6.6, 5.9, 2.8 Hz, 5H), 5.60 (s, 2H), 5.25-5.20 (m, 2H), 5.16 (d, J=12.0 Hz, 1H), 4.35 (s, 2H), 1.90-1.61 (m, 4H), 0.93 (s, 6H).

Step 3-2: A solution of the compound from Step 3-1 (2 g, 7.21 mmol) in CH$_2$Cl$_2$ (55 ml) was treated with BF$_3$.OEt$_2$ (1.8 ml, 14.58 mmol) dropwise, followed by allyltrimethylsilane (3.5 ml, 22.02 mmol) at 0° C. The reaction was warmed to room temperature and stirred overnight. The mixture was concentrated and redissolved in MTBE (100 mL). The solution was quenched with a saturated solution of sodium bicarbonate. The organic layer was extracted with a saturated solution of sodium bicarbonate over 3 times. The combined aqueous layer was adjusted to pH=2 with 1 N HCl solution. The aqueous layer was extracted with ethyl acetate over 3 times. The combined organic layer was dried over sodium sulfate, filtered and concentrated in vacuo to give the desired product (1.80 g, 5.64 mmol, 78% yield) as a colorless syrup.

$^1$H NMR (500 MHz, Chloroform-d) δ 7.46-7.28 (m, 5H), 5.87-5.60 (m, 2H), 5.17 (d, J=13.8 Hz, 2H), 5.02 (t, J=11.2 Hz, 2H), 4.56-4.36 (m, 2H), 3.80-3.03 (m, 8H), 2.55-2.19 (m, 4H), 1.98-1.71 (m, 3H), 1.63 (dp, J=13.2, 6.5 Hz, 2H), 1.08-0.80 (m, 6H). ESI MS m/z=317.86 [M−H]$^−$.

Step 3-3: A solution of the compound from Step 1-5 (349 mg, 1.188 mmol) and the compound from Step 3-2 (435 mg, 1.362 mmol) in DMF (3 ml) and CH$_2$Cl$_2$ (3 ml) was treated with N-methylmorpholine (550 μl, 5.00 mmol) and HATU (550 mg, 1.446 mmol). The reaction was stirred at room temperature for 1 h. The reaction was diluted with ethyl acetate and quenched with a saturated solution of sodium bicarbonate. The organic layer was washed with water and brine, dried over sodium sulfate, filtered and concentrated in vacuo. The crude was added to a 4 g silica gel column and eluted by acetone/cyclohexane from 0% to 100% to give the desired product (177 mg, 0.317 mmol, 27% yield) as a yellow syrup.

ESI MS m/z=557.08 [M−H]$^−$.

Step 3-4: A solution of the compound from Step 3-3 (177 mg, 0.317 mmol) in Toluene (300 ml) was treated with Zhan 1B cat. (47 mg, 0.064 mmol). The mixture was degassed and refilled with N2 by freeze-pump-thaw at −78° C. The reaction was warmed to 90° C. and stirred overnight. The mixture was concentrated in vacuo. The crude was added to a 12 g silica gel column and eluted by acetone/cyclohexane from 0% to 100% to give the desired product (17 mg, 0.032 mmol, 10% yield) as a brownish foam.

ESI MS m/z=529.94 [M−H]$^−$.

Step 3-5: A solution of the compound from Step 3-4 (16 mg, 0.030 mmol) in CH$_2$Cl$_2$ (0.4 ml) was treated with TEA (42.0 μl, 0.302 mmol) and TFAA (21.29 μl, 0.151 mmol) dropwise at 0° C. The reaction was stirred at 0° C. for 30 min. The reaction was quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 3 (7 mg, 0.014 mmol, 45.3% yield) as a white solid.

$^1$H NMR (400 MHz, Chloroform-d) δ 7.84 (d, J=17.9 Hz, 2H), 7.46 (d, J=8.9 Hz, 1H), 7.31 (d, J=6.2 Hz, 5H), 6.95 (d, J=8.2 Hz, 2H), 6.82 (ddt, J=22.8, 15.1, 8.2 Hz, 4H), 6.08 (d, J=12.2 Hz, 1H), 5.63 (d, J=10.9 Hz, 1H), 5.27 (t, J=9.1 Hz, 2H), 5.14 (s, 1H), 5.01 (d, J=8.5 Hz, 2H), 4.97-4.80 (m, 4H), 4.77-4.69 (m, 1H), 4.58 (d, J=10.9 Hz, 1H), 4.38 (t, J=11.2 Hz, 2H), 3.96 (d, J=10.7 Hz, 1H), 3.87 (d, J=10.5 Hz, 2H), 3.83-3.74 (m, 2H), 3.72 (s, 1H), 3.48 (d, J=15.6 Hz, 2H), 3.37 (d, J=16.6 Hz, 1H), 3.16 (s, 1H), 2.94 (d, J=10.9 Hz, 1H), 2.92-2.87 (m, 1H), 2.63 (s, 2H), 2.61 (s, 1H), 2.60-2.47 (m, 2H), 2.18 (d, J=2.4 Hz, 5H), 1.76 (d, J=11.0 Hz, 2H), 1.75-1.67 (m, 3H), 1.43 (dp, J=13.7, 7.0 Hz, 3H), 1.26 (s, 7H), 0.93 (s, 5H), 0.91-0.83 (m, 8H), 0.79 (d, J=6.5 Hz, 2H). ESI MS m/z=511.03 [M−H]$^−$.

Example 4

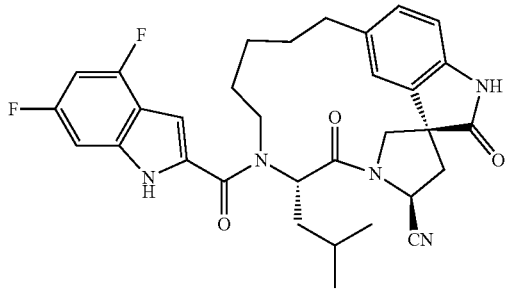

Example 4

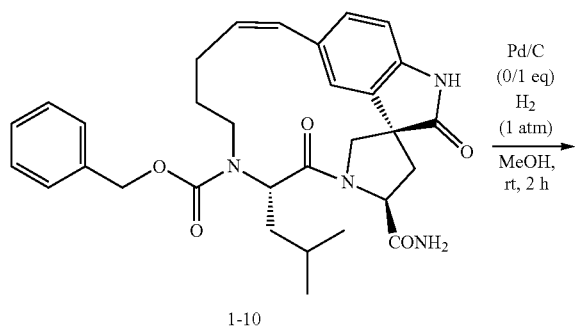

1-10

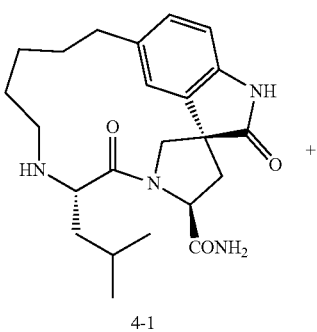

4-1

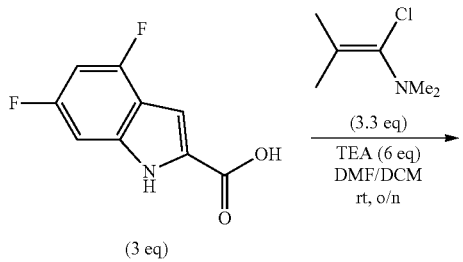

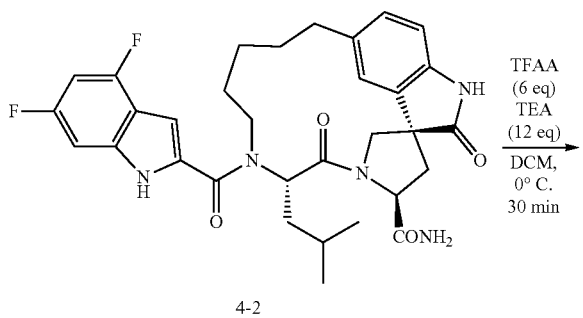

4-2

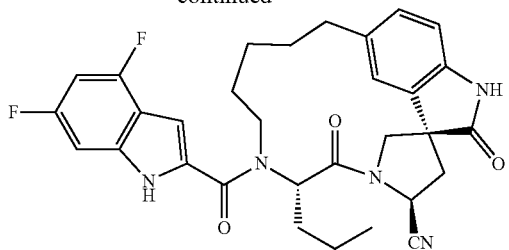

Example 4: 4-3

Step 4-1: A solution of the compound from Step 1-10 (66 mg, 0.121 mmol) in MeOH (1.5 ml) was treated with Pd—C (9 mg, 8.46 µmol) under $H_2$. The mixture was bubbled with $H_2$ over 5 min. The reaction was stirred at room temperature for 2 h. The mixture was filtered through celite, rinsed with dichloromethane and concentrated in vacuo to give the desired product (51 mg, 0.124 mmol, 102% yield).

ESI MS m/z=413.05 [M+H]$^+$.

Step 4-2: A suspension of 4,6-difluoro-1H-indole-2-carboxylic acid (102 mg, 0.517 mmol) in $CH_2Cl_2$ (1.5 ml) was treated with 1-chloro-N,N,2-trimethylprop-1-en-1-amine (100 µl, 0.756 mmol) dropwise. The reaction was stirred at room temperature for 1.5 h to form an orange clear solution. The stock solution of 4,6-difluoro-1H-indole-2-carbonyl chloride (0.35 M) was freshly used. A solution of the compound from Step 4-1 (18 mg, 0.044 mmol) in DMF (0.2 ml) was treated with TEA (40 µl, 0.287 mmol) and a stock solution of 4,6-difluoro-1H-indole-2-carbonyl chloride (0.35 M, 250 µl, 0.085 mmol) in $CH_2Cl_2$ dropwise. The reaction was stirred at room temperature overnight. The mixture was quenched with aqueous ammonia and diluted with ethyl acetate. The organic layer was washed with brine over 3 times, dried over sodium sulfate, filtered and concentrated in vacuo. The crude was added to a 4 g silica gel column and eluted by acetone/cyclohexane from 0% to 100% to give the desired product (10 mg, 0.017 mmol, 39% yield) as an off-white solid.

Step 4-3: A solution of the compound from Step 4-2 (13 mg, 0.022 mmol) in $CH_2Cl_2$ (0.4 ml) was treated with TEA (40 µl, 0.287 mmol) and TFAA (18 µl, 0.127 mmol) dropwise. The reaction was stirred at 0° C. for 1 h and quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 4 (7 mg, 0.012 mmol, 56% yield) as a white solid.

$^1$H NMR (400 MHz, Chloroform-d) δ 9.12 (s, 1H), 8.07 (s, 1H), 7.01 (dd, J=8.0, 1.6 Hz, 1H), 6.88 (d, J=7.9 Hz, 1H), 6.83-6.74 (m, 2H), 6.66-6.55 (m, 2H), 5.44 (t, J=7.5 Hz, 1H), 5.21 (dd, J=10.3, 8.0 Hz, 1H), 4.32 (d, J=10.4 Hz, 1H), 4.13 (dq, J=14.3, 7.3 Hz, 1H), 4.02 (d, J=10.4 Hz, 1H), 3.90-3.74 (m, 1H), 2.94 (dd, J=12.9, 10.3 Hz, 1H), 2.69-2.46 (m, 4H), 1.97 (dt, J=14.4, 7.7 Hz, 1H), 1.67 (ddt, J=69.7, 13.3, 6.7 Hz, 7H), 1.45-1.32 (m, 3H), 1.03-0.76 (m, 9H). ESI MS m/z=572.04 [M−H]$^-$.

Example 5

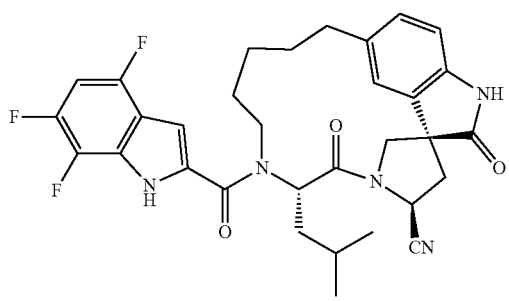

Example 5

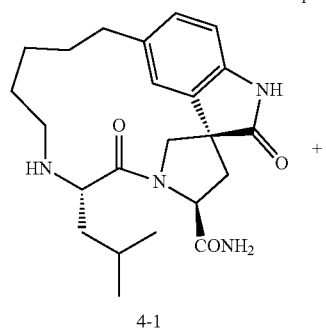

4-1

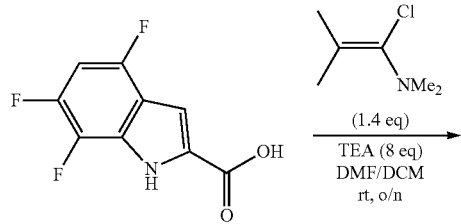

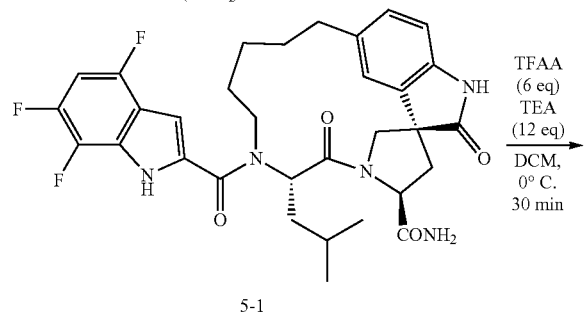

5-1

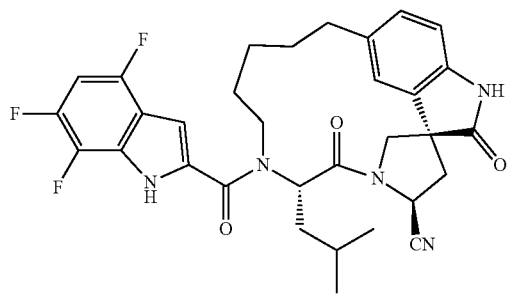

Example 5: 5-2

Step 5-1: A suspension of 4,6,7-trifluoro-1H-indole-2-carboxylic acid (13 mg, 0.060 mmol) in CH$_2$Cl$_2$ (0.3 ml) was treated with 1-chloro-N,N,2-trimethylprop-1-en-1-amine (9 µl, 0.074 mmol) at room temperature. The reaction was stirred at room temperature for 2 h to form a colorless clear solution. The stock solution of 4,6,7-trifluoro-1H-indole-2-carbonyl chloride (0.20 M) was freshly used. A solution of the compound from Step 4-1 (19 mg, 0.046 mmol) in DMF (0.3 ml) was treated with TEA (50 µl, 0.359 mmol) and a stock solution of 4,6,7-trifluoro-1H-indole-2-carbonyl chloride (14 mg, 0.060 mmol) in CH$_2$Cl$_2$ (0.7 ml) freshly prepared dropwise at room temperature. The reaction was stirred at room temperature overnight. The reaction was diluted with ethyl acetate and quenched with aqueous ammonia. The organic layer was washed with brine twice, dried over sodium sulfate, filtered and concentrated in vacuo. The crude was added to a 4 g silica gel column and eluted by acetone/cyclohexane from 0% to 100% to give the desired product (6 mg, 9.84 µmol, 21% yield) as an off-white solid.

Step 5-2: A solution of the compound from Step 5-1 (5.7 mg, 9.35 µmol) in CH$_2$Cl$_2$ (0.4 ml) was treated with TEA (20 µl, 0.143 mmol) and TFAA (8 µl, 0.057 mmol) at 0° C. The reaction was stirred at 0° C. for 30 min. The mixture was quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 5 (4 mg, 6.76 µmol, 72% yield) as a white solid.

$^1$H NMR (400 MHz, Chloroform-d) δ 9.14 (s, 1H), 7.72 (s, 1H), 7.02 (d, J=7.9 Hz, 1H), 6.89 (d, J=7.9 Hz, 1H), 6.81 (s, 1H), 6.72-6.53 (m, 2H), 5.43 (s, 1H), 5.20 (t, J=9.0 Hz, 1H), 4.36 (s, 1H), 4.12 (s, 1H), 4.02 (d, J=10.3 Hz, 1H), 3.83 (d, J=16.0 Hz, 2H), 2.94 (t, J=11.6 Hz, 1H), 2.75-2.45 (m, 4H), 1.96 (s, 1H), 1.89-1.32 (m, 15H), 1.10-0.65 (m, 9H). ESI MS m/z=590.03 [M–H]$^−$.

Example 6

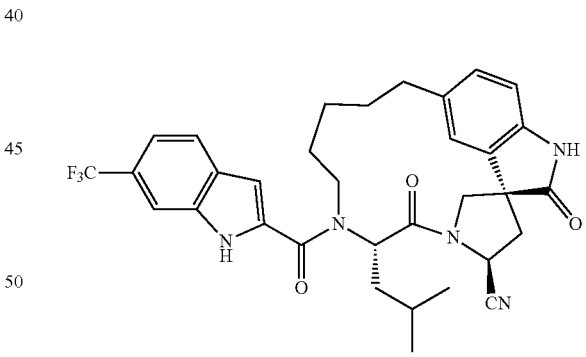

Example 6

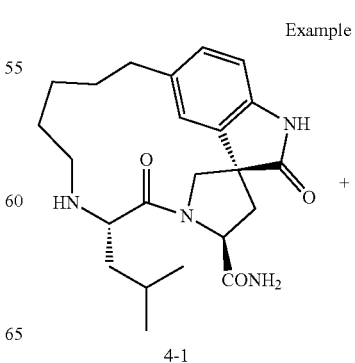

4-1

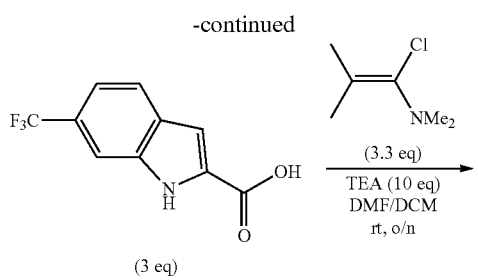

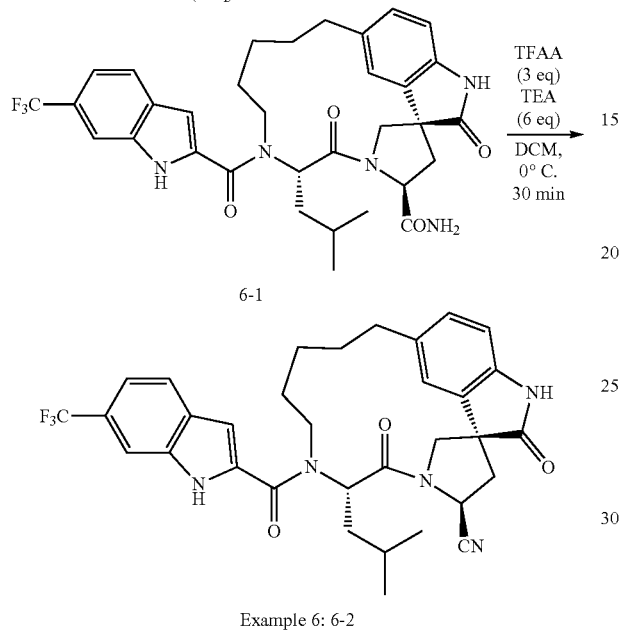

6-1

Example 6: 6-2

Step 5-1: A suspension of 6-(trifluoromethyl)-1H-indole-2-carboxylic acid (36 mg, 0.157 mmol) in CH₂Cl₂ (0.7 ml) was treated with 1-chloro-N,N,2-trimethylprop-1-en-1-amine (25 μl, 0.189 mmol). The mixture turned to a clear yellow solution. The reaction was stirred at room temperature for 1 h. The stock solution of 6-(trifluoromethyl)-1H-indole-2-carbonyl chloride (0.22 M) was freshly used. A solution of the compound from Step 4-1 (19 mg, 0.046 mmol) in DMF (0.400 ml) was treated with a stock solution of 6-(trifluoromethyl)-1H-indole-2-carbonyl chloride (39 mg, 0.158 mmol) in CH₂Cl₂ (0.7 ml). The reaction was stirred at room temperature for 3 h, then quenched with a saturated solution of sodium bicarbonate. The mixture was stirred at room temperature overnight, then diluted with ethyl acetate. The organic layer was washed with brine twice, dried over sodium sulfate, filtered and concentrated in vacuo. The crude was added to a 4 g silica gel column and eluted by acetone/cyclohexane from 0% to 100% to give Product 1 (8 mg, 0.013 mmol, 28% yield) as a white solid. ESI MS m/z=621.99 [M−H]⁻.

Step 6-2: A solution of the compound from Step 14-1 (8 mg, 0.013 mmol) in CH₂Cl₂ (0.3 ml) was treated with TEA (25 μl, 0.179 mmol) and TFAA (9 μl, 0.064 mmol) dropwise at 0° C. The reaction was stirred at 0° C. for 30 min, then quenched with aqueous ammonia. The mixture was stirred at room temperature for 30 min. The aqueous layer was extracted with dichloromethane twice. The combined organic layer was dried over sodium sulfate, filtered and concentrated in vacuo. The crude was added to a 4 g silica gel column and eluted by ethyl acetate/cyclohexane from 0% to 100% to give Example 6 (6.5 mg, 10.73 μmol, 84% yield) as a white solid.

¹H NMR (400 MHz, Chloroform-d) δ 9.06 (s, 1H), 7.84 (s, 1H), 7.66 (dd, J=14.7, 8.4 Hz, 1H), 7.53 (d, J=20.4 Hz, 1H), 7.43-7.30 (m, 1H), 7.12-6.94 (m, 2H), 6.88 (d, J=7.9 Hz, 1H), 6.83-6.74 (m, 1H), 6.63 (s, 1H), 5.47 (t, J=7.6 Hz, 1H), 5.20 (dd, J=10.3, 8.0 Hz, 1H), 4.38 (s, 1H), 4.18 (s, 1H), 4.03 (d, J=10.3 Hz, 1H), 3.82 (d, J=14.9 Hz, 2H), 3.04-2.87 (m, 1H), 2.72-2.40 (m, 4H), 1.98 (dt, J=14.6, 7.1 Hz, 1H), 1.85-1.43 (m, 9H), 1.40-1.29 (m, 2H), 1.07-0.88 (m, 6H), 0.83 (s, 2H). ESI MS m/z=603.89 [M−H]⁻.

Example 7

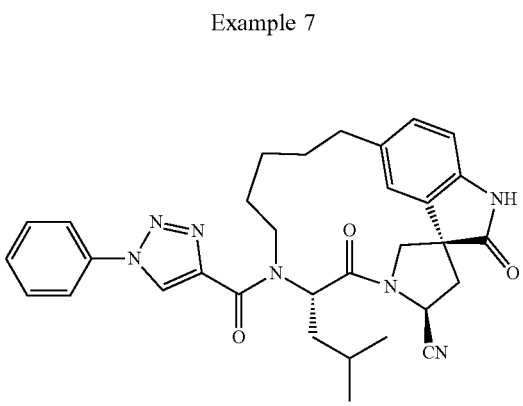

Example 7

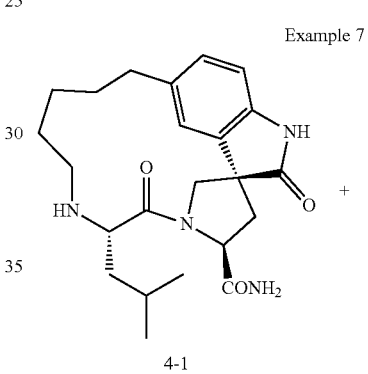

4-1

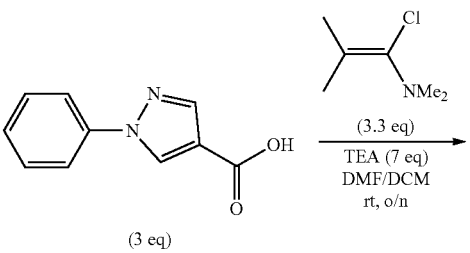

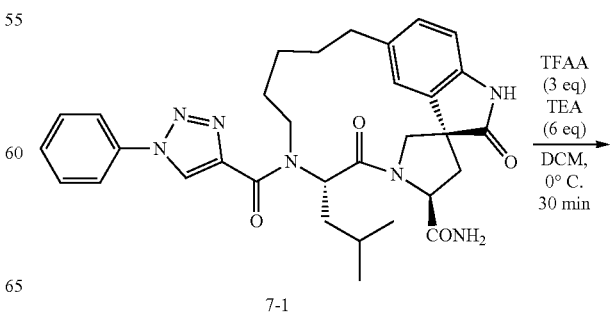

7-1

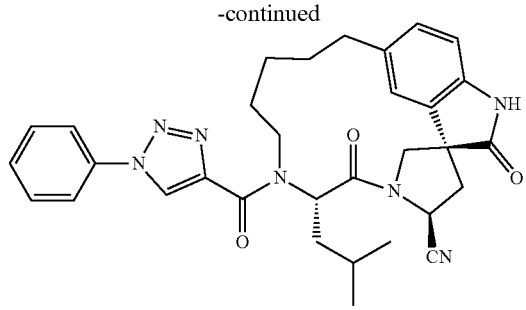

Example 7: 7-2

Step 7-1: A suspension of 1-phenyl-1H-1,2,3-triazole-4-carboxylic acid (50 mg, 0.264 mmol) in CH₂Cl₂ (0.5 ml) was treated with 1-chloro-N,N,2-trimethylprop-1-en-1-amine (40 μl, 0.302 mmol) dropwise. The reaction was stirred at room temperature for 1 h. The stock solution of 1-phenyl-1H-1,2,3-triazole-4-carbonyl chloride (0.53 M) was freshly used. A solution of the compound from Step 7-1 (20 mg, 0.048 mmol) in DMF (0.1 ml) was treated with TEA (50 μl, 0.359 mmol) and a stock solution of 1-phenyl-1H-1,2,3-triazole-4-carbonyl chloride (0.53 M, 300 μl, 0.156 mmol) in CH₂Cl₂ (0.3 ml). The reaction was stirred at room temperature for 1 h and then quenched with aqueous ammonia. The mixture was stirred for additional 10 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (19 mg, 0.033 mmol, 67% yield) as a white solid.

ESI MS m/z=582.03 [M−H]⁻.

Step 7-2: A suspension of the compound from Step 7-1 (18 mg, 0.031 mmol) in CH₂Cl₂ (0.4 ml) was treated with TEA (25 μl, 0.179 mmol) and TFAA (13 μl, 0.092 mmol) dropwise at 0° C. The reaction was stirred at 0° C. for 30 min. The reaction was quenched with a saturated solution of sodium bicarbonate and stirred for 10 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 7 (14 mg, 0.025 mmol, 80% yield) as a white solid.

¹H NMR (400 MHz, Chloroform-d) δ 8.36 (d, J=68.1 Hz, 1H), 7.87 (d, J=73.7 Hz, 1H), 7.69 (dd, J=7.7, 1.8 Hz, 2H), 7.59-7.42 (m, 3H), 6.98 (dd, J=13.5, 7.9 Hz, 1H), 6.82 (dd, J=15.3, 7.9 Hz, 1H), 6.70 (d, J=51.2 Hz, 1H), 6.56 (dd, J=10.1, 4.8 Hz, 1H), 5.57 (t, J=7.4 Hz, 1H), 5.20 (dt, J=18.9, 9.7 Hz, 1H), 4.38 (dd, J=40.3, 10.6 Hz, 1H), 4.10 (dd, J=44.2, 10.5 Hz, 2H), 3.64 (dd, J=90.6, 14.3 Hz, 1H), 2.95 (q, J=11.1 Hz, 1H), 2.62 (h, J=12.9, 11.9 Hz, 3H), 2.33 2.20 (m, 1H), 2.03-1.89 (m, 1H), 1.90-1.32 (m, 9H), 1.15-0.76 (m, 10H). ESI MS m/z=563.99 [M−H]⁻.

Example 8

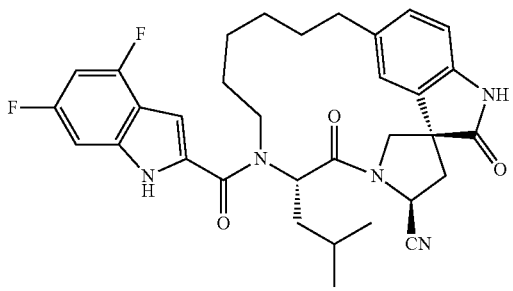

Example 8

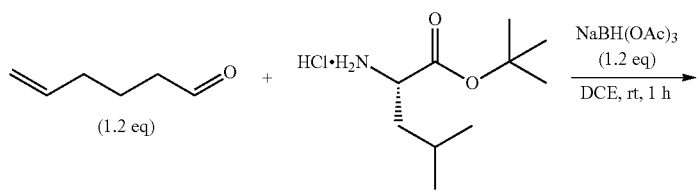

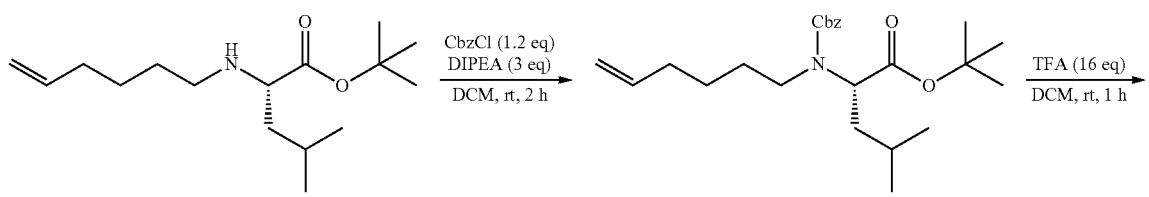

-continued
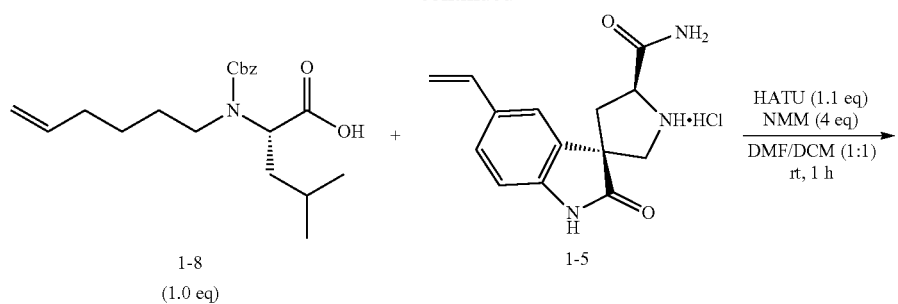
1-8
(1.0 eq)
1-5
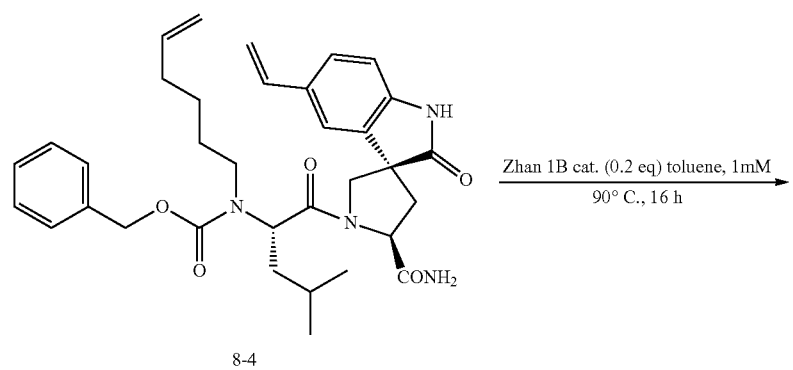
8-4
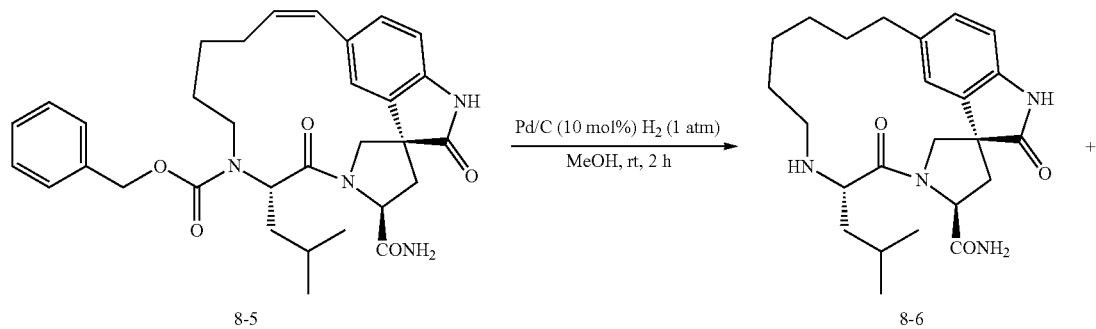
8-5
8-6
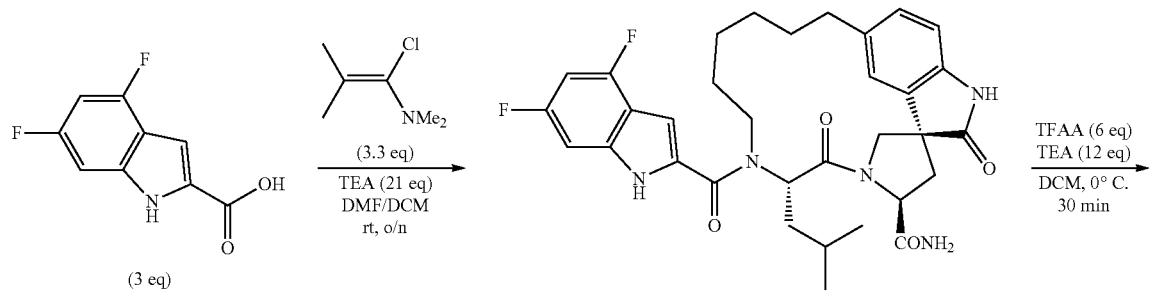
(3 eq)
8-7

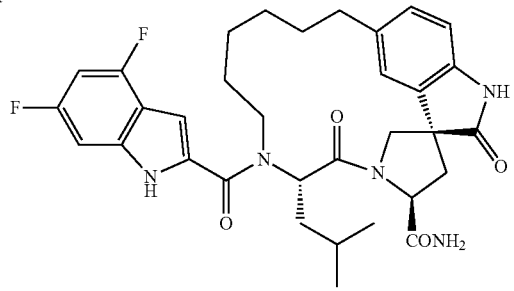

Example 8: 8-8

Step 8-1: A suspension of tert-butyl L-leucinate hydrochloride (5.18 g, 23.15 mmol) and hex-5-enal (2.5 g, 25.5 mmol) in DCE (65 ml) was treated with sodium triacetoxyhydroborate (5.91 g, 27.9 mmol) at room temperature. The reaction was stirred at room temperature for 2 h. The mixture was quenched with a saturated solution of sodium bicarbonate. The mixture was stirred at room temperature for additional 1 h. The aqueous layer was extracted with DCM over 3 times. The combined organic layer was dried over sodium sulfate, filtered and concentrated in vacuo to give the desired product (4.2 g, 15.59 mmol, 67% yield) as a light yellow oil.

ESI MS m/z=269.86 [M+H]$^+$.

Step 8-2: A solution the compound from Step 8-1 (4.2 g, 15.59 mmol) in $CH_2Cl_2$ (60 ml) was treated with TEA (6.5 ml, 46.6 mmol) and Cbz-Cl (2.7 ml, 18.91 mmol) dropwise. The reaction was stirred at room temperature for 2 h. The reaction was quenched with a saturated solution of sodium bicarbonate. The aqueous layer was extracted with dichloromethane over 3 times. The combined organic layer was dried over sodium sulfate, filtered and concentrated in vacuo. The crude was added to a 120 g silica gel column and eluted by MTBE/cyclohexane from 0% to 50% to the desired product (3.5 g, 8.67 mmol, 56% yield) as a colorless oil.

$^1$H NMR (400 MHz, Chloroform-d) δ 7.34 (t, J=4.8 Hz, 5H), 5.89-5.67 (m, 1H), 5.28-4.88 (m, 4H), 4.54-4.21 (m, 1H), 3.47-3.28 (m, 1H), 3.07-2.91 (m, 1H), 2.04 (dt, J=22.7, 7.2 Hz, 2H), 1.81-1.47 (m, 8H), 1.39 (d, J=10.5 Hz, 11H), 1.00-0.83 (m, 6H). ESI MS m/z=425.94 [M+H]$^+$.

Step 8-3: A solution of the compound from Step 8-2 (380 mg, 0.942 mmol) in $CH_2Cl_2$ (2 ml) was treated with TFA (1.5 ml, 19.47 mmol) dropwise. The reaction was stirred at room temperature for 1 h. The mixture was concentrated in vacuo and coevaporated with toluene twice. The crude was dried under high vacuum for 30 min to give the desired product (350 mg, 1.01 mmol, 107% yield).

$^1$H NMR (400 MHz, DMSO-d$_6$) δ 7.35 (s, 5H), 5.84-5.66 (m, 1H), 5.18 (s, 2H), 4.95 (t, J=12.2 Hz, 2H), 4.41 (d, J=6.7 Hz, 1H), 3.42 (s, 1H), 3.06 (s, 1H), 2.01 (d, J=7.2 Hz, 2H), 1.95-1.46 (m, 6H), 1.37 (d, J=25.4 Hz, 2H), 1.02-0.89 (m, 6H). ESI MS m/z=345.84 [M−H]$^-$.

Step 8-4: A solution of the compound from Step 8-3 (350 mg, 1.007 mmol) and the compound from Step 1-5 (296 mg, 1.007 mmol) in DMF (4 ml) was treated with HATU (286 mg, 0.752 mmol) and N-methylmorpholine (550 μL, 5.00 mmol) at 0° C. The reaction was warmed to room temperature and stirred for 1 h, then quenched with aqueous ammonia and diluted with ethyl acetate. The organic layer was washed with brine twice, dried over sodium sulfate, filtered and concentrated in vacuo. The crude was added to 12 g silica gel column and eluted by acetone/cyclohexane from 0% to 100% to give the desired product (84 mg, 0.143 mmol, 14% yield) as a colorless syrup.

ESI MS m/z=585.08 [M−H]$^-$.

Step 8-5: A solution of the compound from Step 8-4 (84 mg, 0.143 mmol) in toluene (140 ml) was treated with Zhan 1B cat. (21 mg, 0.029 mmol). The mixture was degassed by freeze-pump-thaw at −78° C. and backfilled with $N_2$ over 3 times. The reaction was warmed to 90° C. and stirred overnight. The mixture was concentrated in vacuo. The crude was added to a 4 g silica gel column and eluted by acetone/cyclohexane from 0% to 100% to give the desired product (10 mg, 0.018 mmol, 13% yield) as a brownish foam.

ESI MS m/z=557.07 [M−H]$^-$.

Step 8-6: A solution of a mixture of the compound from Step 8-5 (10 mg, 0.018 mmol) in MeOH (0.4 ml) was treated with Pd—C (2 mg, 0.019 mmol) under $N_2$. The mixture was bubbled with 1 atm $H_2$ over 5 min. The reaction was stirred at room temperature for 3 h. The mixture was filtered through a celite, rinsed with MeOH and concentrated in vacuo to the desired product (7.3 mg, 0.017 mmol, 94% yield).

ESI MS m/z=426.97 [M+H]$^+$.

Step 8-7: A solution of 4,6-difluoro-1H-indole-2-carboxylic acid (198 mg, 1.004 mmol) in $CH_2Cl_2$ (2 ml) was treated with 1-chloro-N,N,2-trimethylprop-1-en-1-amine (150 μL, 1.134 mmol) dropwise. The reaction was stirred at room temperature for 2 h. The stock solution of 4,6-difluoro-1H-indole-2-carbonyl chloride (0.5 M) was freshly used. A solution of the compound from Step 8-6 (7.3 mg, 0.017 mmol) in DMF (0.2 ml) was treated with TEA (50 μl, 0.359 mmol) and a stock solution of 4,6-difluoro-1H-indole-2-carbonyl chloride (100 μl, 0.051 mmol) dropwise. The reaction was stirred at room temperature over weekend. The reaction was quenched with aqueous ammonia and stirred for 30 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (2.7 mg, 0.04 mmol, 14% yield) as an off-white solid.

ESI MS m/z=603.93 [M−H]$^-$.

Step 8-8: A solution of a mixture of the compound from Step 8-7 (2.7 mg, 0.04 mmol) in $CH_2Cl_2$ (0.3 ml) was treated with TEA (20 μl, 0.143 mmol) and TFAA (10 μl, 0.071 mmol) dropwise at 0° C. The reaction was stirred at 0° C. for 30 min, then quenched with aqueous ammonia. The mixture was stirred at room temperature for 30 min. The aqueous layer was extracted with dichloromethane over 3 times. The combined organic layer was dried over sodium sulfate, filtered and concentrated in vacuo. The crude was purified by reverse phase HPLC to give Example 8 (0.61 mg, 1.038 μmol, 8% yield) as a white solid.

ESI MS m/z=586.00 [M−H]$^-$.

Example 9
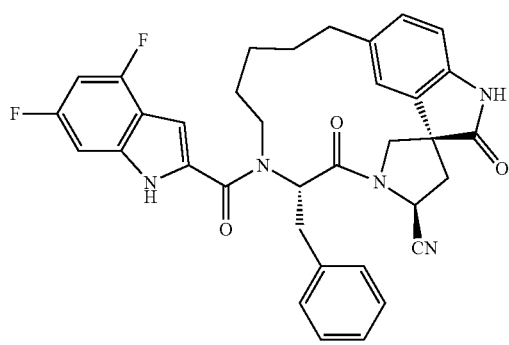
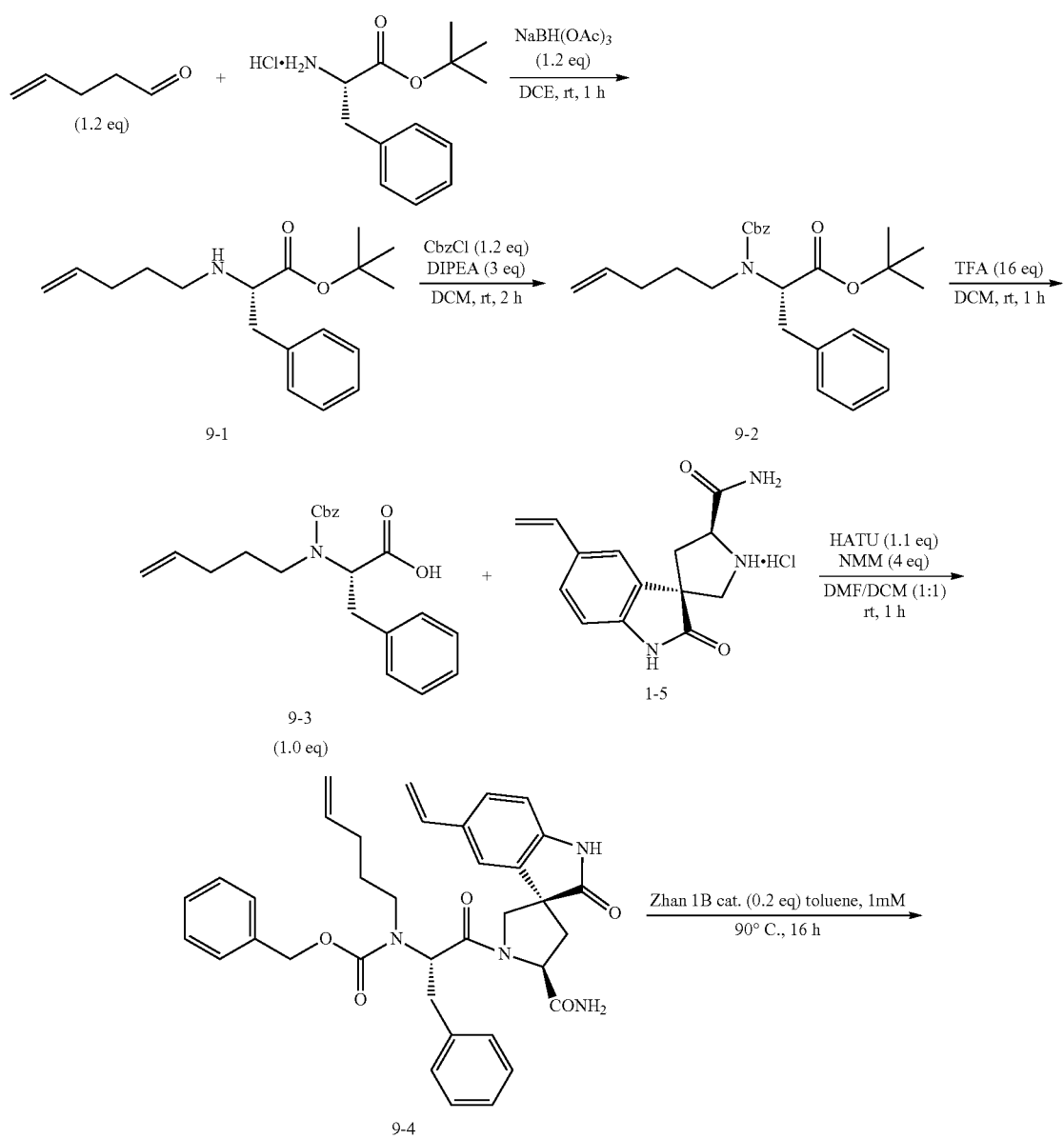

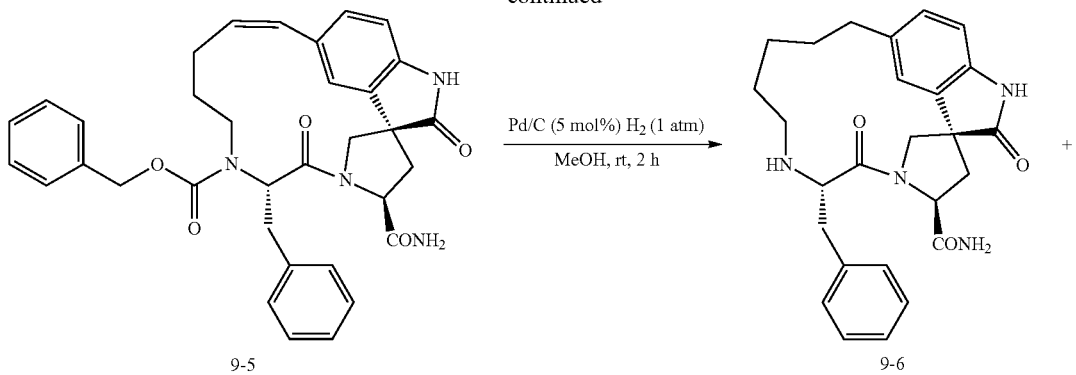

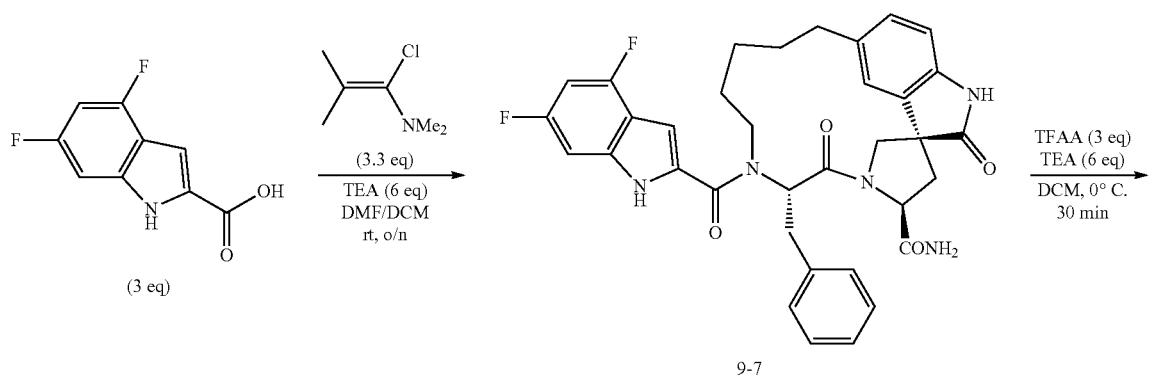

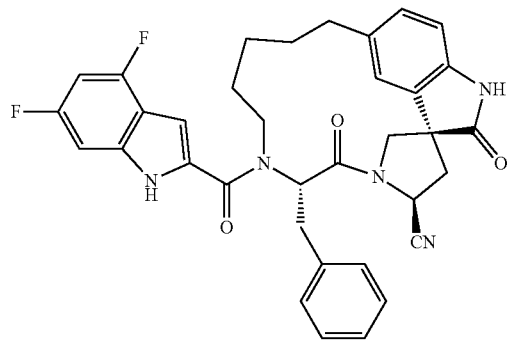

Example 9: 9-8

Step 9-1: A suspension of tert-butyl L-phenylalaninate hydrochloride (16 g, 62.1 mmol) and pent-4-enal (7.3 ml, 73.9 mmol) in DCE (200 ml) was treated with sodium triacetoxyborohydride (19 g, 90 mmol) portionwise over 10 min at room temperature. The reaction was stirred at room temperature overnight to form a light pink solution. The reaction was quenched with a saturated solution of sodium bicarbonate at 0° C. The mixture was stirred at room temperature for 1 h. The aqueous layer was extracted with dichloromethane over 3 times. The combined organic layer was dried over sodium sulfate, filtered and concentrated in vacuo. The crude was added to a 120 g silica gel column and eluted by MTBE/CH from 0% to 60% to give the desired product (8.45 g, 29.2 mmol, 47% yield) as a colorless oil.

$^1$H NMR (400 MHz, Chloroform-d) δ 7.33-7.26 (m, 1H), 7.25 (s, 1H), 7.24-7.17 (m, 3H), 5.77 (ddt, J=16.9, 10.1, 6.6 Hz, 1H), 5.05-4.88 (m, 2H), 3.45 (dd, J=8.1, 6.3 Hz, 1H), 3.00 (ddd, J=54.7, 13.7, 7.3 Hz, 2H), 2.73-2.52 (m, 2H), 2.11-1.99 (m, 2H), 1.63 (q, J=7.0 Hz, 2H), 1.45 (d, J=18.7 Hz, 3H), 1.33 (s, 9H). ESI MS m/z=289.87 [M+H]$^+$.

Step 9-2: A solution of the compound from Step 9-1 (5.34 g, 12.61 mmol, 98% yield) in CH$_2$Cl$_2$ (50 ml) was treated with DIPEA (9 ml, 51.5 mmol) and Cbz-Cl (2.2 ml, 15.41 mmol) dropwise. The reaction was stirred at room temperature for 2 h and quenched with a saturated solution of sodium bicarbonate. The aqueous layer was extracted with dichloromethane over 3 times. The combined organic layer was dried over sodium sulfate, filtered and concentrated in vacuo. The crude was added to an 80 g silica gel column and eluted by MTBE/cyclohexane from 0% to 20% to give the desired product (5.34 g, 12.61 mmol, 98% yield) as a colorless oil.

$^1$H NMR (400 MHz, Chloroform-d) δ 7.35 (q, J=6.3, 5.3 Hz, 4H), 7.25-7.11 (m, 3H), 7.04 (d, J=7.1 Hz, 1H), 5.67 (ddt, J=24.5, 16.2, 8.3 Hz, 1H), 5.15 (s, 1H), 5.06-4.84 (m, 2H), 4.17-3.98 (m, 1H), 3.34-3.01 (m, 3H), 2.64 (dt, J=14.7, 7.6 Hz, 1H), 1.92 (dt, J=25.2, 7.0 Hz, 2H), 1.39 (d, J=6.4 Hz, 9H). ESI MS m/z=445.97 [M+Na]$^+$.

Step 9-3: A solution of the compound from Step 9-2 (739 mg, 1.745 mmol) in CH$_2$Cl$_2$ (3.5 ml) was treated with TFA (2.5 ml, 32.4 mmol) dropwise. The reaction was stirred at room temperature for 1 h. The mixture was concentrated in vacuo, then co-evaporated with toluene twice. The crude was dried under high vacuum overnight to give the desired product (681 mg, 1.853 mmol, 106% yield) as a colorless syrup.

$^1$H NMR (400 MHz, Chloroform-d) δ 7.35 (q, J=4.6, 3.7 Hz, 4H), 7.23 (td, J=6.1, 4.9, 3.1 Hz, 2H), 7.14-7.03 (m, 2H), 5.77-5.54 (m, 1H), 5.32-5.08 (m, 2H), 4.99-4.83 (m, 2H), 4.22-4.04 (m, 1H), 3.44-3.06 (m, 3H), 2.65 (dt, J=14.7, 7.7 Hz, 1H), 1.87 (ddq, J=21.5, 14.4, 7.9, 7.5 Hz, 2H), 1.54-1.22 (m, 2H). ESI MS m/z=365.87 [M−H]$^−$.

Step 9-4: A suspension of the compound from Step 9-3 (670 mg, 1.823 mmol) and the compound from Step 1-5 (529 mg, 1.801 mmol) in DMF (3 ml) and CH$_2$Cl$_2$ (6 ml) was treated with N-methylmorpholine (792 μl, 7.20 mmol). The reaction was stirred at room temperature for 5 min to form a cloudy suspension. The mixture was treated with HATU (698 mg, 1.836 mmol) in one portion. The reaction was stirred at room temperature for 1 h, then quenched with a saturated solution of sodium bicarbonate and diluted with ethyl acetate. The organic layer was washed with water and brine, dried over sodium sulfate, filtered and concentrated in vacuo. The crude was added to a 40 g silica gel column and eluted by acetone/cyclohexane from 0% to 100% to give the desired product (221 mg, 0.364 mmol, 20% yield) as a white foam.

$^1$H NMR (400 MHz, Chloroform-d) δ 7.58 (d, J=49.2 Hz, 1H), 7.29 (d, J=13.7 Hz, 3H), 7.00 (s, 2H), 6.94-6.73 (m, 1H), 6.53 (dd, J=17.7, 10.9 Hz, 1H), 5.74 (d, J=7.1 Hz, 1H), 5.55 (d, J=17.5 Hz, 1H), 5.30 (s, 1H), 5.20-4.93 (m, 2H), 4.91-4.66 (m, 2H), 4.58 (d, J=12.5 Hz, 1H), 4.40 (d, J=10.8 Hz, 1H), 4.15 (dd, J=14.9, 9.2 Hz, 1H), 3.67-3.45 (m, 1H), 3.36 (dt, J=24.2, 9.0 Hz, 2H), 3.08-2.88 (m, 1H), 2.81-2.56 (m, 1H), 2.45-2.23 (m, 1H), 2.04 (d, J=7.9 Hz, 2H), 1.64 (d, J=54.0 Hz, 6H). ESI MS m/z=605.02 [M−H]$^−$.

Step 9-5: A solution of the compound from Step 9-4 (100 mg, 0.165 mmol) in toluene (160 ml) was treated with Zhan 1B cat. (24 mg, 0.033 mmol). The mixture was freezed to −78° C., degassed and backfilled with N$_2$ by freeze-pump-thaw over 3 times. The reaction was warmed to 90° C. and stirred overnight. The mixture was concentrated in vacuo. The crude was added to a 12 g silica gel column and eluted by acetone/cyclohexane from 0% to 100% to give the desired product (27 mg, 0.047 mmol, 28% yield) as a brownish foam.

$^1$H NMR (400 MHz, Methanol-d$_4$) δ 7.30-6.98 (m, 12H), 6.91 (ddd, J=14.6, 9.1, 6.6 Hz, 4H), 6.48 (dd, J=11.0, 6.7 Hz, 1H), 5.67 (dtd, J=27.5, 10.9, 5.7 Hz, 1H), 5.17 (dd, J=10.6, 4.4 Hz, 1H), 4.75-4.60 (m, 2H), 4.15-4.03 (m, 2H), 3.89-3.79 (m, 1H), 3.73-3.51 (m, 3H), 3.13 (dd, J=13.7, 10.8 Hz, 1H), 2.99 (dt, J=33.9, 14.1, 4.9 Hz, 1H), 2.50-2.23 (m, 4H), 2.10-1.95 (m, 2H), 1.88 (d, J=13.5 Hz, 1H), 1.79-1.60 (m, 2H), 1.60-1.42 (m, 2H). ESI MS m/z=576.97 [M−H]$^−$.

Step 9-6: A solution of the compound from Step 9-5 (26 mg, 0.045 mmol) in MeOH (0.3 ml) was treated with Pd—C (3.8 mg, 3.57 μmol) under 1 atm H$_2$. The mixture was bubbled with H$_2$ over 5 min. The reaction was stirred at room temperature for 2 h. The mixture was filtered through celite and rinsed with MeOH. The resulting filtrate was concentrated in vacuo to give the desired product (19 mg, 0.043 mmol, 95% yield) as a brownish foam.

ESI MS m/z=447.11 [M+H]$^+$.

Step 9-7: A suspension of 4,6-difluoro-1H-indole-2-carboxylic acid (102 mg, 0.517 mmol) in CH$_2$Cl$_2$ (1 ml) was treated with 1-chloro-N,N,2-trimethylprop-1-en-1-amine (80 μl, 0.605 mmol) dropwise. The reaction was stirred at room temperature for 2 h to form a brownish solution. The stock solution of 4,6-difluoro-1H-indole-2-carbonyl chloride (0.50 M) was freshly used. A solution of the compound from Step 9-6 (19 mg, 0.043 mmol) in DMF (0.2 ml) was treated with TEA (35.6 μl, 0.255 mmol) and a stock solution of 4,6-difluoro-1H-indole-2-carbonyl chloride (0.50 M, 255 μl, 0.128 mmol) dropwise. The reaction was stirred at room temperature overnight. The reaction was quenched with aqueous ammonia and stirred at room temperature for 30 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (18 mg, 0.029 mmol, 67% yield) as a light yellow foam.

$^1$H NMR (400 MHz, Methanol-d$_4$) δ 11.10 (s, 1H), 7.20 (ddd, J=37.5, 30.6, 7.4 Hz, 6H), 7.00 (dd, J=7.9, 1.6 Hz, 1H), 6.94-6.79 (m, 2H), 6.79-6.70 (m, 1H), 6.54 (td, J=10.2, 2.0 Hz, 1H), 6.09 (d, J=2.1 Hz, 1H), 5.76 (d, J=9.9 Hz, 1H), 5.00 (dd, J=10.2, 8.1 Hz, 1H), 4.37 (s, 1H), 4.11 (t, J=12.7 Hz, 1H), 4.02 (d, J=10.3 Hz, 1H), 3.76 (d, J=11.1 Hz, 2H), 3.41-3.33 (m, 1H), 3.14 (dd, J=14.3, 4.8 Hz, 1H), 2.69-2.57 (m, 2H), 2.57-2.33 (m, 4H), 1.68 (t, J=12.6 Hz, 1H), 1.50 (s, 1H), 1.34 (d, J=16.5 Hz, 3H), 1.21-1.09 (m, 1H), 0.97-0.68 (m, 2H), 0.57 (s, 1H). ESI MS m/z=623.97 [M−H]$^−$.

Step 9-8: A solution of the compound from Step 9-7 (17 mg, 0.027 mmol) in CH$_2$Cl$_2$ (0.5 ml) was treated with TEA (25 μl, 0.179 mmol) and TFAA (13 μl, 0.092 mmol) dropwise at 0° C. The reaction was stirred at 0° C. for 30 min and then quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 9 (12 mg, 0.020 mmol, 73% yield) as a white solid.

$^1$H NMR (400 MHz, Methanol-d$_4$) δ 7.36-7.27 (m, 2H), 7.23 (dd, J=8.4, 6.8 Hz, 2H), 7.19-7.11 (m, 1H), 7.01 (dd, J=7.9, 1.6 Hz, 1H), 6.88 (d, J=7.9 Hz, 1H), 6.79 (dd, J=9.1, 2.0 Hz, 1H), 6.73 (d, J=1.6 Hz, 1H), 6.57 (td, J=10.3, 2.1 Hz, 1H), 6.22 (d, J=0.9 Hz, 1H), 5.64 (t, J=8.0 Hz, 1H), 5.37 (dd, J=10.1, 8.0 Hz, 1H), 4.33 (d, J=10.6 Hz, 1H), 4.20-4.06 (m, 2H), 3.85 (dd, J=12.6, 8.3 Hz, 2H), 2.72 (dd, J=12.7, 10.1 Hz, 1H), 2.66-2.48 (m, 4H), 1.69 (q, J=14.6, 14.1 Hz, 1H), 1.50 (td, J=9.3, 4.7 Hz, 1H), 1.41-1.28 (m, 2H), 1.16 (d, J=10.2 Hz, 1H), 1.01-0.84 (m, 1H), 0.82-0.69 (m, 1H), 0.60 (s, 1H). ESI MS m/z=606.04 [M−H]$^−$.

Example 10

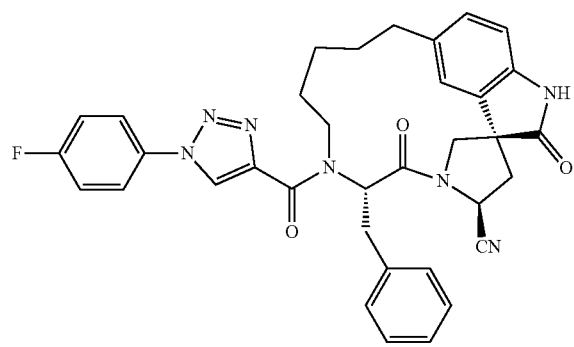

Example 10

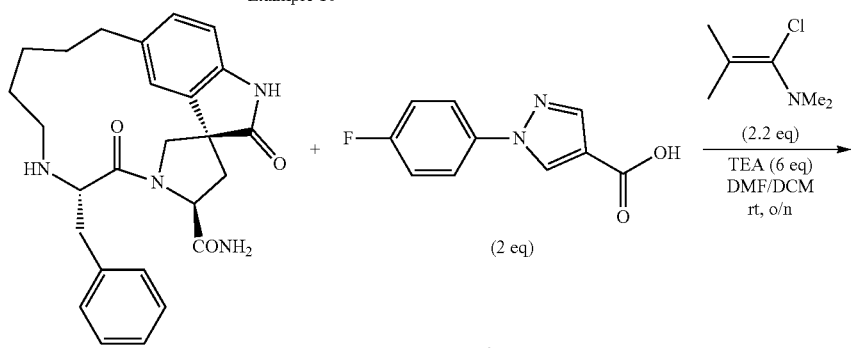

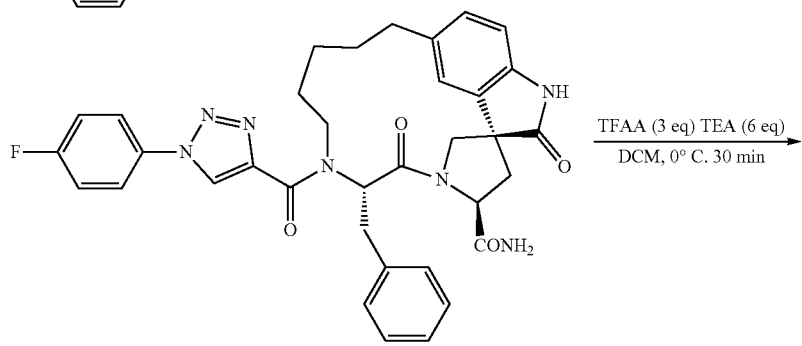

10-1

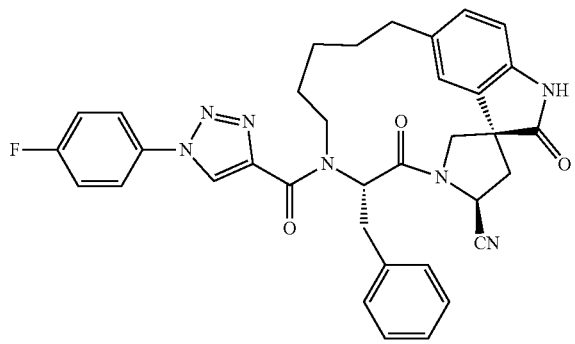

Example 10: 10-2

Step 10-1: A suspension of 1-(4-fluorophenyl)-1H-1,2,3-triazole-4-carboxylic acid (38 mg, 0.183 mmol) in CH$_2$Cl$_2$ (0.6 ml) was treated with 1-chloro-N,N,2-trimethylprop-1-en-1-amine (26 µl, 0.197 mmol) dropwise. The reaction was stirred at room temperature for 1 h. The stock solution of 1-(4-fluorophenyl)-1H-1,2,3-triazole-4-carbonyl chloride (0.30 M) was freshly used. A solution of the compound from Step 9-6 (17 mg, 0.038 mmol) in DMF (0.2 ml) was treated with TEA (30 µl, 0.215 mmol) and a stock solution of 1-(4-fluorophenyl)-1H-1,2,3-triazole-4-carbonyl chloride (250 µl, 0.075 mmol) in DCM dropwise at room temperature. The reaction was stirred at room temperature for 2 h.

The mixture was quenched with ammonium hydroxide and stirred for additional 30 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (15 mg, 0.024 mmol, 62% yield) as a white solid.

$^1$H NMR (400 MHz, Methanol-$d_4$) δ 7.77-7.63 (m, 3H), 7.30 (t, J=8.7 Hz, 4H), 7.15 (d, J=7.3 Hz, 1H), 7.12-6.97 (m, 4H), 6.96-6.78 (m, 6H), 6.32 (dd, J=11.0, 3.1 Hz, 1H), 5.07 (t, J=9.1 Hz, 1H), 4.57 (d, J=8.3 Hz, 2H), 4.23-3.97 (m, 3H), 3.58 (dd, J=13.7, 5.9 Hz, 1H), 3.12 (dd, J=14.1, 11.0 Hz, 2H), 2.91 (dd, J=14.0, 3.2 Hz, 1H), 2.73 (d, J=13.9 Hz, 1H), 2.69-2.35 (m, 7H), 1.89 (d, J=23.0 Hz, 1H), 1.79-1.61 (m, 2H), 1.56-1.28 (m, 5H), 1.11-0.60 (m, 3H). ESI MS m/z=634.04 [M−H]$^−$.

Step 10-2: A solution of the compound from Step 10-1 (15 mg, 0.024 mmol) in CH$_2$Cl$_2$ (0.4 ml) was treated with TEA (25 μl, 0.179 mmol) and TFAA (10 μl, 0.071 mmol) drop- wise at 0° C. The reaction was stirred at 0° C. for 30 min. The reaction was quenched with a saturated solution of sodium bicarbonate. The aqueous layer was extracted with ethyl acetate over 3 times. The combined organic layer was dried over sodium sulfate, filtered and concentrated in vacuo. The crude was added to a 4 g silica gel column and eluted by ethyl acetate/cyclohexane from 0% to 100% to give Example 10 (11 mg, 0.018 mmol, 75% yield) as a white solid.

$^1$H NMR (400 MHz, Chloroform-d) δ 7.71 (d, J=51.7 Hz, 2H), 7.59-7.48 (m, 2H), 7.25-7.18 (m, 3H), 7.11-6.88 (m, 6H), 6.86-6.71 (m, 2H), 6.50 (dd, J=9.6, 5.0 Hz, 1H), 5.20 (dd, J=10.2, 8.0 Hz, 1H), 4.49-4.36 (m, 1H), 4.12 (dd, J=15.1, 8.1 Hz, 2H), 3.60 (dd, J=13.0, 5.9 Hz, 1H), 3.27-2.97 (m, 3H), 2.92 (dd, J=13.0, 10.3 Hz, 1H), 2.71 (d, J=13.7 Hz, 1H), 2.66-2.43 (m, 4H), 1.77 (d, J=41.4 Hz, 4H), 1.62-1.30 (m, 5H), 1.14-0.65 (m, 3H). ESI MS m/z=616.04 [M−H]$^−$.

Example 11

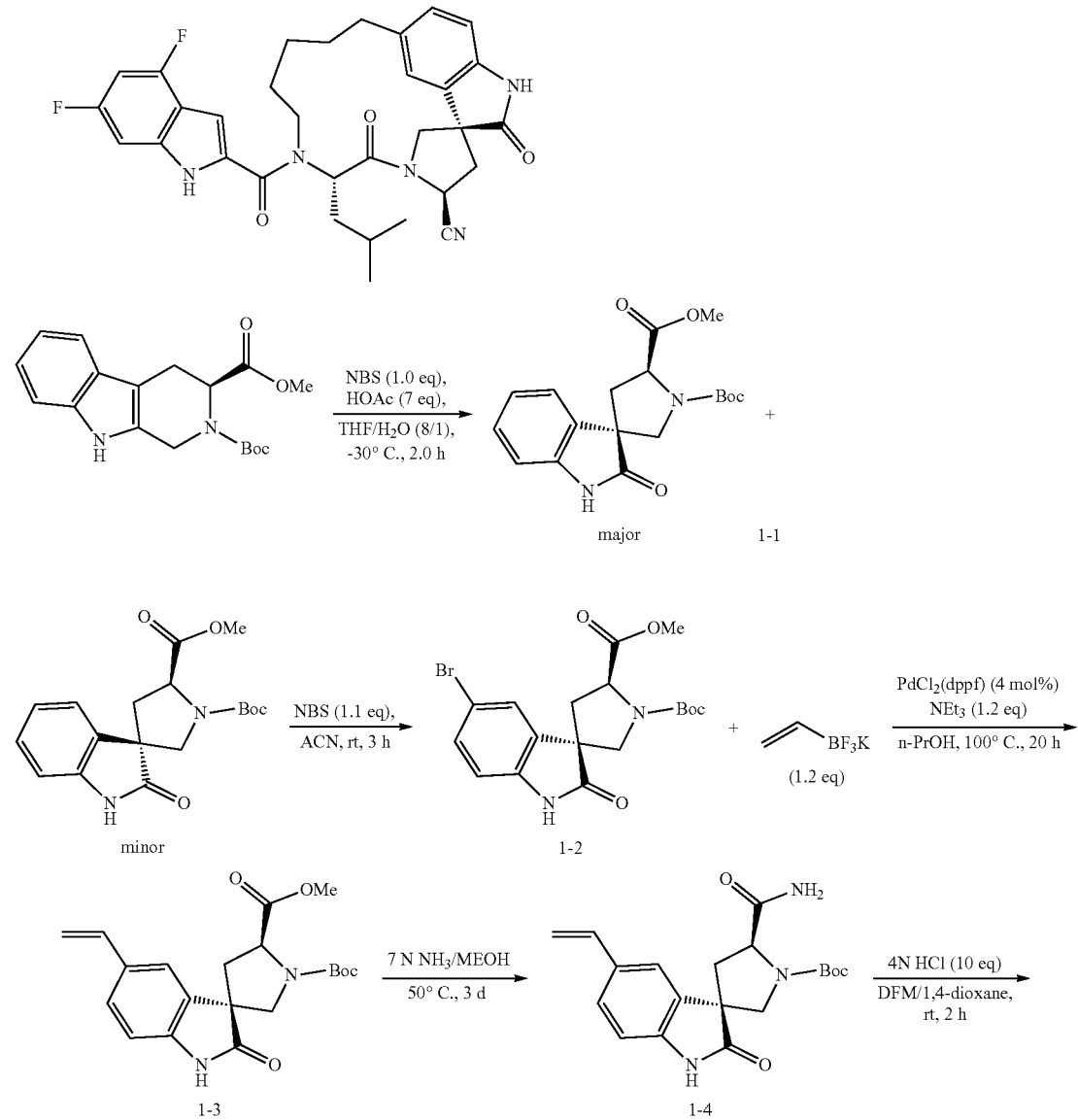

-continued
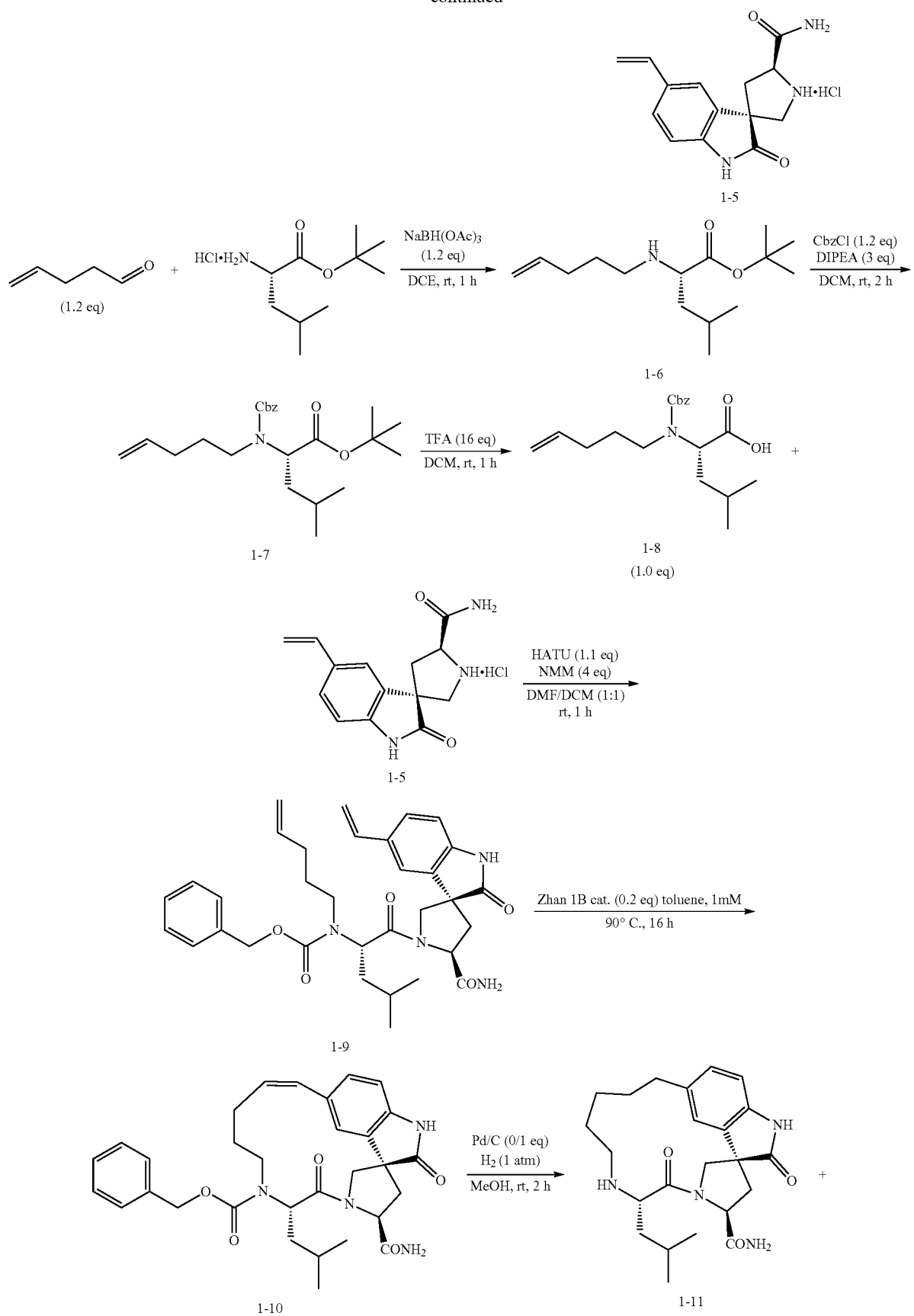

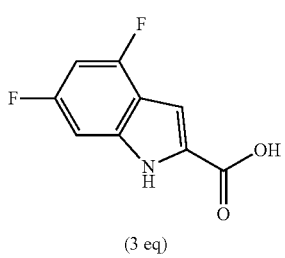
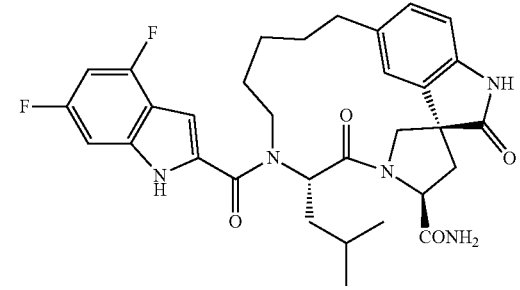

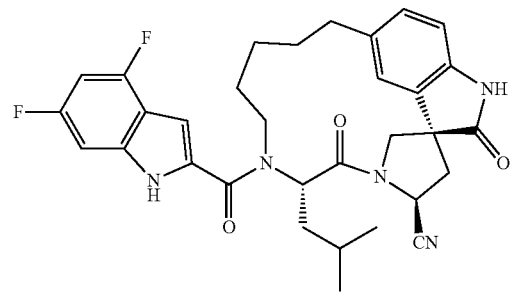

Example 11

Step 11-1: To a clear colorless solution of 2-(tert-butyl) 3-methyl (S)-1,3,4,9-tetrahydro-2H-pyrido[3,4-b]indole-2,3-dicarboxylate (45.00 g, 136 mmol) in THF (720 ml) in a three neck 2000 mL flask at 0° C. (internal temperature) was added water (90 ml) in one portion. Acetic acid (54.6 ml, 953 mmol) was added at 0° C. The cloudy mixture was cooled to −30° C. (internal temperature). It became a milky solution. A solution of NBS (24.24 g, 136 mmol) in THF/120 (8/1, 207 ml) was added dropwise over 30 min while maintaining the internal temperature below −30° C. The milky mixture became a yellow cloudy solution and was stirred at −30° C. for 1.0 h. The cloudy yellow solution was allowed to warm up to −20° C. and poured portionwise into a mixture of potassium carbonate (65.9 g, 477 mmol) in cold water (~300 ml), saturated NaHCO$_3$ solution (~400 ml) and EtOAc (300 ml) with stirring. The mixture was further diluted with EtOAc (500 ml). The aqueous layer was extracted with EtOAc. The combined organic layers were washed with brine, dried over Na$_2$SO$_4$, filtered and concentrated to afford crude product as a light yellow sticky oil (56.0 g). The crude product was dissolved in DCM (60 ml) and filtered through a 330 g silica gel column (MTBE/Cyclohexane) to afford the mixture of major and minor diastereomers as an off-white foam (48.20 g, 102%, dr 10/1).

$^1$H NMR (400 MHz, DMSO-d$_6$) δ 10.66 (d, J=1.9 Hz, 1H), 7.23 (td, J=7.7, 1.2 Hz, 1H), 7.07 (ddd, J=15.0, 7.5, 1.3 Hz, 1H), 6.99 (tdd, J=7.5, 2.7, 1.0 Hz, 1H), 6.93-6.87 (m, 1H), 4.68-4.55 (m, 1H), 3.71 (d, J=12.5 Hz, 3H), 3.61-3.46 (m, 2H), 2.38 (ddd, J=12.8, 7.9, 1.5 Hz, 1H), 2.25 (ddd, J=18.4, 12.8, 9.0 Hz, 1H), 1.44-1.32 (m, 9H). ESI MS m/z=369.12 [M+Na]$^+$.

Step 11-2: A clear colorless solution of the mixture of compounds from Step 11-1 (3.94 g, 11.4 mmol, dr 10/1) in acetonitrile (40 mL) was treated with NBS (2.23 g, 12.5 mmol) in three portions at room temperature. The reaction was stirred at room temperature for 3 h. It became a light-yellow solution. LCMS showed no SM. The reaction was quenched with aqueous Na$_2$S$_2$O$_3$. The mixture was allowed to stir at room temperature for additional 30 min. The cloudy mixture was further diluted with EtOAc (80 mL). The aqueous layer was extracted with EtOAc twice. The combined organic layers were washed with brine, dried over Na$_2$SO$_4$, filtered, and concentrated to afford crude product as an off-white solid. The crude was dissolved in DCM (10 mL) and filtered through a silica gel pad (MTBE) to afford the desired product (dr 10/1) as a white solid. The product was treated with MTBE/hexane (2:1) (30 mL). The mixture was sonicated over 10 min to form a milky suspension, which was filtered and washed with MTBE/hexane (2:1) to give the desired product as a white solid (4.23 g, 10.0 mmol, dr >100/1).

$^1$H NMR (400 MHz, DMSO-d$_6$) δ 10.78 (s, 1H), 7.42 (dd, J=8.3, 2.0 Hz, 1H), 7.20 (dd, J=18.7, 2.0 Hz, 1H), 6.86 (d, J=8.3 Hz, 1H), 4.68 (dt, J=13.0, 8.4 Hz, 1H), 3.71 (d, J=12.0 Hz, 3H), 3.66-3.59 (m, 1H), 3.47 (dd, J=10.7, 7.4 Hz, 1H), 2.24 (ddd, J=18.4, 12.9, 8.7 Hz, 1H), 1.40 (d, J=5.7 Hz, 6H). ESI MS m/z=422.74, 424.64 [M−H]$^−$.

Step 11-3: A clear colorless solution of the compound from Step 11-2 (4.2 g, 9.9 mmol) in n-PrOH (35 mL) was treated with triethylamine (1.7 mL, 11.9 mmol), potassium vinyltrifluoroborate (1.6 g, 11.9 mmol) and PdCl$_2$(dppf) (290 mg, 0.4 mmol) under N$_2$. The mixture was degassed and backfilled with N$_2$. The resulting orange suspension was bubbled with N$_2$ for 10 min. The reaction was warmed to 100° C. and stirred for 20 h. It became dark red/brown mixture. The reaction mixture was diluted with ethyl acetate (100 mL) and quenched with aqueous NaHCO$_3$. The aqueous layer was extracted with ethyl acetate. The combined organic layers were washed with water and brine, dried over Na$_2$SO$_4$, filtered and concentrated in vacuo. The crude was redissolved in ethyl acetate (20 mL) and treated with SiliaMetS DMT (8 g) as a metal scavenger. The mixture was stirred at room temperature for 16 h, then filtered, rinsed with MTBE/CH (2:1) (200 mL) and concentrated in vacuo. The brownish crude was redissolved in ethyl acetate (20 mL), treated with activated charcoal and warmed to 60° C. for 1 h. The mixture was filtered after cooling to give a light-yellow solution, which was further concentrated in vacuo to give the desired product (3.3 g, 8.7 mmol, 90%) as an off-white foam.

$^1$H NMR (400 MHz, DMSO-d$_6$) δ 10.72 (s, 1H), 7.38-7.30 (m, 1H), 7.22-7.14 (m, 1H), 6.87 (d, J=8.0 Hz, 1H), 6.68 (ddd, J=18.2, 10.9, 7.5 Hz, 1H), 5.65 (dd, J=17.6, 10.4 Hz, 1H), 5.13 (dd, J=11.0, 5.7 Hz, 1H), 4.76-4.65 (m, 1H), 3.71 (d, J=12.0 Hz, 3H), 3.65-3.58 (m, 1H), 3.50 (t, J=10.8 Hz, 1H), 2.44 (dd, J=12.9, 8.1 Hz, 1H), 2.26 (ddd, J=18.9, 12.8, 8.8 Hz, 1H), 1.43-1.36 (m, 9H). ESI MS m/z=370.79 [M–H]$^-$.

Step 11-4: A clear light-yellow solution of the compound from Step 11-3 (3.3 g, 8.9 mmol) in 7 N ammonia in MeOH (80 ml, 560 mmol) was stirred at 50° C. in a sealed pressure vessel over the weekend (3 d). LCMS showed no SM. The mixture was allowed to cool down and concentrated in vacuo to give a yellow gel-like solid. The solid was redissolved in 30 mL MeOH/dioxane (1:10), co-evaporated in vacuo to give a light-yellow solid. The crude was dried under high vacuum for 1 h, then mashed to small pieces and dried under high vacuum overnight to give a light-yellow powder. The powder was washed with 10 mL DCM/MTBE (1:2), sonicated and filtered to give the desired product (3.05 g, 8.5 mmol, 96%) as an off-white solid.

$^1$H NMR (400 MHz, DMSO-d$_6$) δ 10.73 (s, 1H), 7.51 (s, 1H), 7.37-7.29 (m, 1H), 7.17-6.98 (m, 2H), 6.88 (d, J=8.0 Hz, 1H), 6.66 (dt, J=17.5, 10.9 Hz, 1H), 5.58 (dd, J=17.5, 11.8 Hz, 1H), 5.14 (t, J=10.3 Hz, 1H), 4.50 (q, J=8.5, 7.9 Hz, 1H), 3.57 (s, 3H), 3.50 (t, J=10.3 Hz, 1H), 2.31-2.14 (m, 2H), 1.80 (d, J=13.8 Hz, 1H), 1.39 (d, J=25.4 Hz, 9H). ESI MS m/z=355.79 [M–H]$^-$.

Step 11-5: To a clear solution of the compound from Step 11-4 (1.15 g, 3.22 mmol) in DMF (2 ml) at rt was added 4 M HCl in 1,4-dioxane (8 ml, 32 mmol). The resulting clear yellow solution was stirred at rt for 2 h. The mixture was concentrated by rotavapor. The residual clear DMF solution was poured into DCM (150 ml) with stirring to get a white slurry. The mixture was sonicated to form a cloudy suspension. The solid was collected by filtration, washing with DCM, and then MTBE. The solid was dried under vacuum to afford the desired product as an off-white powder (862 mg, 2.93 mmol, 91%). 1 g of the above product was mixed with DMF (2 ml) and heated with a heat gun to get an almost clear solution. Solid started to appear while heating. The mixture was allowed to cool down to rt. The solid was collected by filtration, washing with DMF (0.2 ml), DCM and MTBE. The solid was dried under vacuum to afford the desired product as a white solid (771 mg).

$^1$H NMR (500 MHz, DMSO-d$_6$) δ 10.84 (d, J=3.0 Hz, 1H), 9.03 (s, 1H), 8.13-7.95 (m, 1H), 7.85-7.70 (m, 2H), 7.39 (td, J=8.2, 1.8 Hz, 1H), 6.94-6.81 (m, 1H), 5.31 (qd, J=6.8, 2.0 Hz, 1H), 4.66 (dt, J=11.4, 6.2 Hz, 1H), 2.57-2.52 (m, 1H), 2.25 (ddd, J=12.7, 10.6, 1.5 Hz, 1H), 1.84 (dd, J=6.8, 1.7 Hz, 2H). ESI MS m/z=257.77 [M–H]$^-$.

Step 11-6: A solution of tert-butyl L-leucine hydrochloride (2.1 g, 9.39 mmol) and pent-4-enal (1 g, 11.89 mmol) in DCE (30 ml) was treated with sodium triacetoxyborohydride (2.7 g, 12.74 mmol) at room temperature. The reaction was stirred at room temperature for 2 h and then quenched with a saturated solution of sodium bicarbonate. The aqueous layer was extracted with dichloromethane over 3 times. The combined organic layer was dried over sodium sulfate, filtered and concentrated in vacuo. The crude was added to a 80 g silica gel column and eluted by MTBE/cyclohexane from 0% to 100% to give the desired product (1.96 g, 7.67 mmol, 82% yield) as a pale yellow oil.

ESI MS m/z=255.84 [M+H]$^+$.

Step 11-7: A solution of the compound from Step 11-6 (1.96 g, 7.67 mmol) in CH$_2$Cl$_2$ (30 ml) was treated with DIPEA (4.02 ml, 23.02 mmol) and Cbz-Cl (1.315 ml, 9.21 mmol) at 0° C. The reaction was warmed to room temperature and stirred for 2 h. The reaction was quenched with a saturated solution of Na2CO3. The aqueous layer was extracted with dichloromethane over 3 times. The combined organic layer was dried over sodium sulfate, filtered and concentrated in vacuo. The crude was added to an 80 g silica gel column and eluted by MTBE/cyclohexane from 0% to 100% to give the desired product (2.64 g, 6.78 mmol, 88% yield) as a colorless oil.

$^1$H NMR (400 MHz, Chloroform-d) δ 7.34 (t, J=4.8 Hz, 5H), 5.89-5.67 (m, 1H), 5.28-4.88 (m, 4H), 4.54-4.21 (m, 1H), 3.47-3.28 (m, 1H), 3.07-2.91 (m, 1H), 2.04 (dt, J=22.7, 7.2 Hz, 2H), 1.81-1.47 (m, 8H), 1.39 (d, J=10.5 Hz, 11H), 1.00-0.83 (m, 6H). ESI MS m/z=411.93 [M+Na]$^+$.

Step 11-8: A solution of the compound from Step 11-7 (650 mg, 1.669 mmol) in CH$_2$Cl$_2$ (2 ml) was treated with TFA (2 ml, 26.0 mmol) at room temperature. The reaction was stirred at room temperature for 1 h. The mixture was concentrated in vacuo, then co-evaporated with toluene twice. The crude was dried under high vacuum to give the desired product (547 mg, 1.641 mmol, 98% yield) as an off-white syrup.

$^1$H NMR (400 MHz, Chloroform-d) δ 7.34 (d, J=8.5 Hz, 5H), 5.89-5.63 (m, 1H), 5.29-4.83 (m, 7H), 4.42 (t, J=7.8 Hz, 1H), 3.41 (d, J=20.1 Hz, 1H), 3.06 (ddd, J=15.2, 10.2, 5.6 Hz, 1H), 2.22-1.54 (m, 8H), 1.06-0.79 (m, 6H). ESI MS m/z=331.85 [M–H]$^-$.

Step 11-9: A solution of the compound from Step 11-5 (335 mg, 1.140 mmol) and the compound from Step 11-8 (375 mg, 1.125 mmol) in DMF (2 ml) and CH$_2$Cl$_2$ (2 ml) was treated with N-methyl morpholine (500 μl, 4.55 mmol) and HATU (470 mg, 1.236 mmol). The reaction was stirred at room temperature for 1 h. The reaction was quenched with a saturated solution of sodium bicarbonate and diluted with ethyl acetate. The organic layer was washed with water and brine twice, dried over sodium sulfate, filtered and concentrated in vacuo. The crude was added to a 12 g silica gel column and eluted by acetone/cyclohexane from 0% to 100% to give the desired product (230 mg, 0.402 mmol, 35% yield) as a white solid.

$^1$H NMR (500 MHz, DMSO-d$_6$) δ 10.78 (d, J=17.6 Hz, 1H), 7.50 (s, 1H), 7.43-7.15 (m, 3H), 7.15-6.83 (m, 4H), 6.58 (dd, J=17.4, 11.0, 1H), 5.87-5.62 (m, 1H), 5.54 (d, J=17.6 Hz, 1H), 5.19-4.74 (m, 4H), 4.74-4.50 (m, 2H), 3.93 (d, J=10.3 Hz, 1H), 3.74 (d, J=10.2 Hz, 1H), 3.67-3.48 (m, 1H), 3.13 (tt, J=11.9, 6.8 Hz, 2H), 2.35-2.07 (m, 2H), 2.03-1.85 (m, 2H), 1.72-1.34 (m, 4H), 0.95-0.67 (m, 6H). ESI MS m/z=571.07 [M–H]$^-$.

Step 11-10: A solution of the compound from Step 11-9 (163 mg, 0.285 mmol) in toluene (250 ml) was treated with Zhan 1B cat. (41 mg, 0.056 mmol). The mixture was degassed by freeze-pump-thaw and refilled with N$_2$ over 3 times. The reaction was warmed to 90° C. and stirred overnight. The reaction was concentrated in vacuo. The crude washed added to a 12 g silica gel column and eluted by acetone/cyclohexane from 0% to 100% to give the desired product (163 mg, 0.285 mmol, 86% yield) as a brownish foam.

$^1$H NMR (500 MHz, Methanol-d$_4$) δ 7.40-6.82 (m, 11H), 6.48 (t, J=10.4 Hz, 1H), 5.67 (dtd, J=39.4, 11.0, 5.9 Hz, 1H), 5.30 (d, J=11.8 Hz, 1H), 5.20 (t, J=7.5 Hz, 1H), 5.04-4.89 (m, 2H), 4.78-4.61 (m, 2H), 4.11-4.00 (m, 1H), 3.78 (d, J=10.0 Hz, 1H), 3.72-3.53 (m, 2H), 3.37 (dd, J=14.2, 3.4 Hz, 1H), 2.51-2.22 (m, 5H), 2.12-1.86 (m, 2H), 1.84-1.30 (m, 8H), 1.00-0.78 (m, 6H). ESI MS m/z=543.06 [M−H]⁻.

Step 11-11: A solution of the compound from Step 11-10 (66 mg, 0.121 mmol) in MeOH (1.5 ml) was treated with Pd—C (9 mg, 8.46 µmol) under H₂. The mixture was bubbled with H₂ over 5 min. The reaction was stirred at room temperature for 2 h. The mixture was filtered through celite, rinsed with dichloromethane and concentrated in vacuo to give the desired product (51 mg, 0.124 mmol, 102% yield).

ESI MS m/z=413.05 [M+H]⁺.

Step 11-12: A suspension of 4,6-difluoro-1H-indole-2-carboxylic acid (102 mg, 0.517 mmol) in CH₂Cl₂ (1.5 ml) was treated with 1-chloro-N,N,2-trimethylprop-1-en-1-amine (100 µl, 0.756 mmol) dropwise. The reaction was stirred at room temperature for 1.5 h to form an orange clear solution. The stock solution of 4,6-difluoro-1H-indole-2-carbonyl chloride (0.35 M) was freshly used. A solution of the compound from Step 1-11 (18 mg, 0.044 mmol) in DMF (0.2 ml) was treated with TEA (40 µl, 0.287 mmol) and a stock solution of 4,6-difluoro-1H-indole-2-carbonyl chloride (0.35 M, 250 µl, 0.085 mmol) in CH₂Cl₂ dropwise. The reaction was stirred at room temperature overnight. The mixture was quenched with aqueous ammonia and diluted with ethyl acetate. The organic layer was washed with brine over 3 times, dried over sodium sulfate, filtered and concentrated in vacuo. The crude was added to a 4 g silica gel column and eluted by acetone/cyclohexane from 0% to 100% to give the desired product (10 mg, 0.017 mmol, 39% yield) as an off-white solid.

ESI MS m/z=591.95 [M+H]⁺.

Step 11-13: A solution of the compound from Step 11-12 (13 mg, 0.022 mmol) in CH₂Cl₂ (0.4 ml) was treated with TEA (40 µl, 0.287 mmol) and TFAA (18 µl, 0.127 mmol) dropwise. The reaction was stirred at 0° C. for 1 h and quenched with a saturated solution of sodium bicarbonate. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 11 (7 mg, 0.012 mmol, 56% yield) as a white solid.

¹H NMR (400 MHz, Chloroform-d) δ 9.12 (s, 1H), 8.07 (s, 1H), 7.01 (dd, J=8.0, 1.6 Hz, 1H), 6.88 (d, J=7.9 Hz, 1H), 6.83-6.74 (m, 2H), 6.66-6.55 (m, 2H), 5.44 (t, J=7.5 Hz, 1H), 5.21 (dd, J=10.3, 8.0 Hz, 1H), 4.32 (d, J=10.4 Hz, 1H), 4.13 (dq, J=14.3, 7.3 Hz, 1H), 4.02 (d, J=10.4 Hz, 1H), 3.90-3.74 (m, 1H), 2.94 (dd, J=12.9, 10.3 Hz, 1H), 2.69-2.46 (m, 4H), 1.97 (dt, J=14.4, 7.7 Hz, 1H), 1.67 (ddt, J=69.7, 13.3, 6.7 Hz, 7H), 1.45-1.32 (m, 3H), 1.03-0.76 (m, 9H). ESI MS m/z=572.04 [M−H]⁻.

Example 12

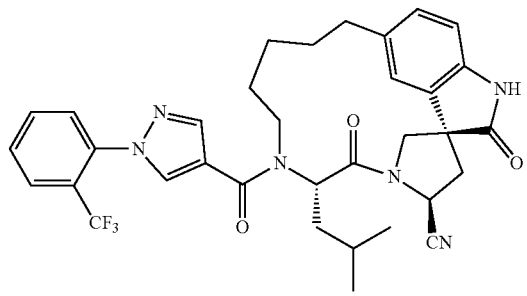

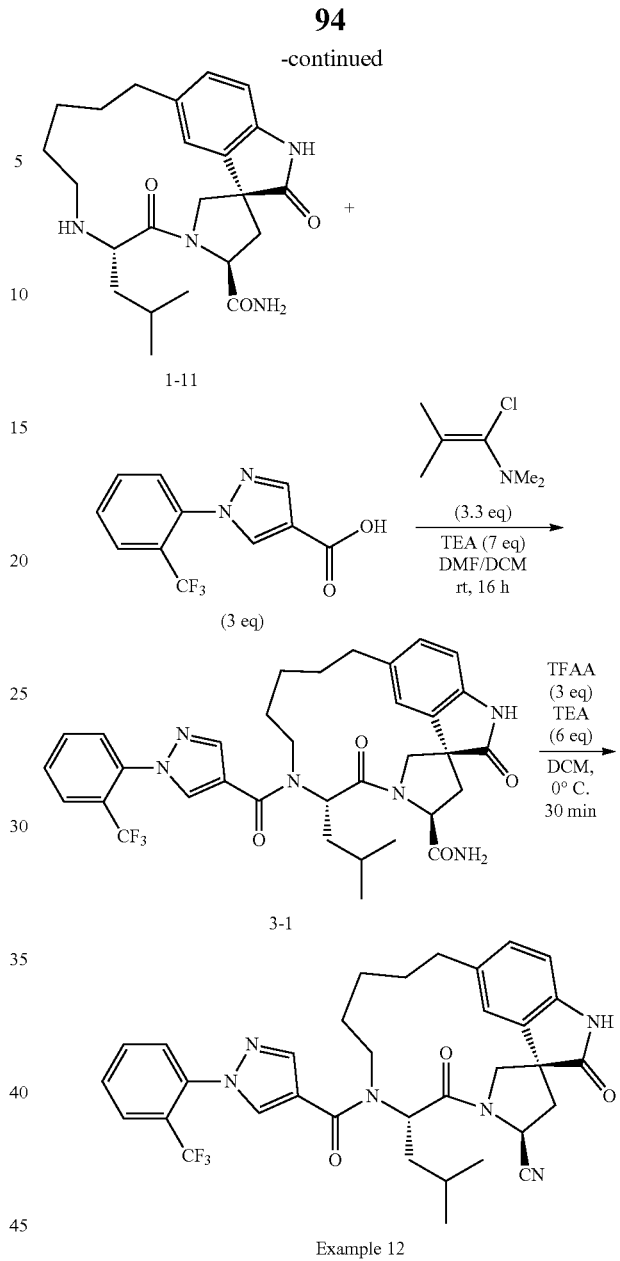

Example 12

Step 12-1: A suspension of 1-(2-(trifluoromethyl)phenyl)-1H-pyrazole-4-carboxylic acid (55 mg, 0.215 mmol) in CH₂Cl₂ (0.5 ml) was treated with 1-chloro-N,N,2-trimethylprop-1-en-1-amine (34 µl, 0.257 mmol) dropwise. The reaction was stirred at room temperature for 1 h. The stock solution of 1-(2-(trifluoromethyl)phenyl)-1H-pyrazole-4-carbonyl chloride (0.42 M) was freshly used. A solution of the compound from Step 1-11 (14 mg, 0.034 mmol) in DMF (0.1 ml) was treated with TEA (40 µl, 0.287 mmol) and a stock solution of 1-(2-(trifluoromethyl)phenyl)-1H-pyrazole-4-carbonyl chloride (0.42 M, 250 µl, 0.105 mmol) in CH₂Cl₂ dropwise. The reaction was stirred at room temperature overnight and then quenched with aqueous ammonia. The mixture was stirred for additional 10 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (18 mg, 0.028 mmol, 82% yield) as a white solid.

$^1$H NMR (500 MHz, Methanol-d$_4$) δ 8.03 (s, 1H), 7.90 (dd, J=7.9, 1.6 Hz, 1H), 7.80 (td, J=7.7, 1.5 Hz, 1H), 7.78-7.71 (m, 1H), 7.69 (s, 1H), 7.53 (d, J=7.8 Hz, 1H), 7.05 (dd, J=7.9, 1.6 Hz, 1H), 6.89 (d, J=7.9 Hz, 1H), 6.86 (d, J=1.8 Hz, 1H), 5.62-5.35 (m, 1H), 4.99 (dd, J=10.1, 8.0 Hz, 1H), 4.02-3.81 (m, 2H), 3.61 (d, J=14.9 Hz, 1H), 2.71-2.56 (m, 2H), 2.55-2.40 (m, 2H), 1.85 (s, 1H), 1.79-1.45 (m, 6H), 1.33 (d, J=17.2 Hz, 2H), 0.94 (dd, J=27.6, 6.6 Hz, 8H).

ESI MS m/z=649.40 [M−H]$^-$.

Step 12-2: A suspension of the compound from Step 12-1 (17 mg, 0.026 mmol) in CH$_2$Cl$_2$ (0.3 ml) was treated with TEA (30 μl, 0.215 mmol) and TFAA (12 μl, 0.085 mmol) dropwise at 0° C. The reaction was stirred at 0° C. for 30 min. The reaction was quenched with aqueous ammonia and stirred for 10 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 12 (16 mg, 0.025 mmol, 97% yield) as a white solid.

$^1$H NMR (400 MHz, Methanol-d$_4$) δ 8.05 (s, 1H), 7.90 (dd, J=7.8, 1.7 Hz, 1H), 7.81 (dd, J=8.4, 6.6 Hz, 1H), 7.77-7.63 (m, 2H), 7.54 (d, J=7.8 Hz, 1H), 7.05 (dd, J=8.0, 1.6 Hz, 1H), 6.90 (dd, J=7.9, 1.2 Hz, 1H), 6.74 (d, J=1.7 Hz, 1H), 5.41 (dd, J=9.9, 8.1 Hz, 2H), 4.17-4.04 (m, 1H), 3.90 (t, J=11.5 Hz, 2H), 3.66 (d, J=15.3 Hz, 1H), 2.82-2.74 (m, 1H), 2.64 (td, J=14.0, 13.5, 8.5 Hz, 3H), 1.93 (s, 1H), 1.78 (d, J=9.7 Hz, 1H), 1.58 (dt, J=13.3, 8.0 Hz, 3H), 1.50 (s, 1H), 1.38-1.28 (m, 1H), 1.28-1.21 (m, 2H), 1.06-0.74 (m, 8H).

ESI MS m/z=631.42 [M−H]$^-$.

Example 13

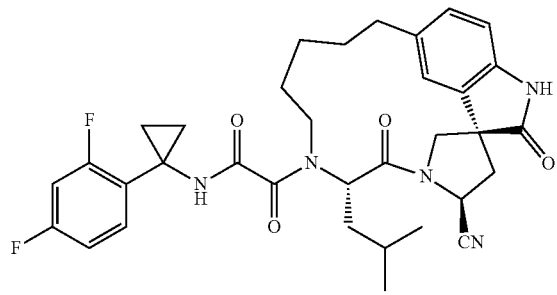

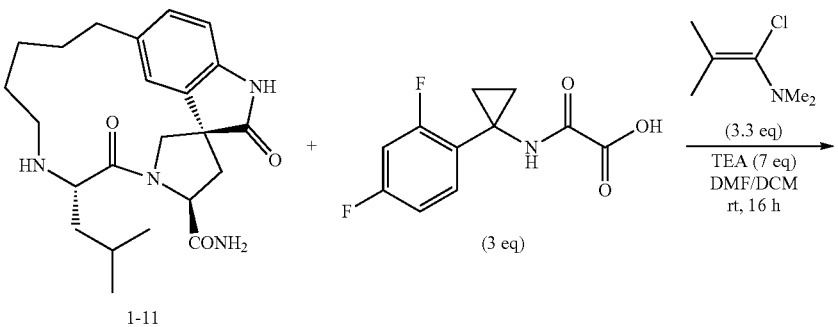

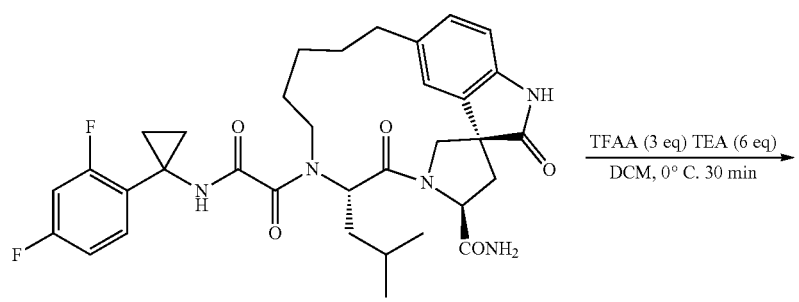

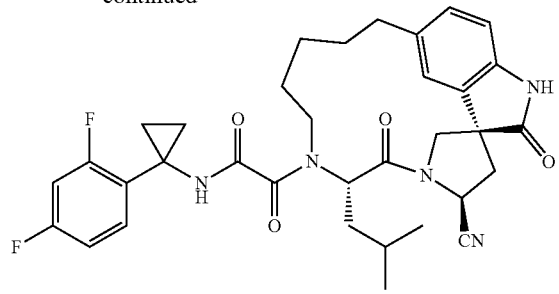

Example 13

Step 13-1: A suspension of 2-((1-(2,4-difluorophenyl)cyclopropyl)amino)-2-oxoacetic acid (39 mg, 0.162 mmol) in CH$_2$Cl$_2$ (0.4 ml) was treated with 1-chloro-N,N,2-trimethylprop-1-en-1-amine (24 µl, 0.181 mmol) dropwise at room temperature. The reaction was stirred at room temperature for 1 h to give a clear stock solution (0.404 molar) of 2-((1-(2,4-difluorophenyl)cyclopropyl)amino)-2-oxoacetyl chloride in DCM that was freshly used. A solution of the compound from Step 1-11 (17 mg, 0.041 mmol) in DMF (0.1 ml) was treated with TEA (40 µl, 0.287 mmol) and a stock solution of 2-((1-(2,4-difluorophenyl)cyclopropyl)amino)-2-oxoacetyl chloride (300 µl, 0.120 mmol) in DCM dropwise. The reaction was stirred at room temperature overnight, then quenched with ammonium hydroxide. The mixture was stirred for additional 30 min. The aqueous layer was extracted with dichloromethane over 3 times. The combined organic layer was dried over sodium sulfate, filtered and concentrated in vacuo. The crude was added to a 4 g silica gel column and eluted by acetone/cyclohexane from 0% to 100% to give the desired product (14 mg, 0.022 mmol, 53.4% yield) as a white solid.

1H NMR (400 MHz, Methanol-d$_4$) (mixture of rotamers) δ 8.00 (s, 1H), 7.70-7.52 (m, 1H), 7.07 (ddd, J=12.4, 7.8, 1.6 Hz, 1H), 6.99-6.82 (m, 3H), 5.31 (t, J=7.4 Hz, 0.5H), 4.96 (ddd, J=17.9, 10.1, 7.9 Hz, 0.5H), 4.44 (dd, J=11.2, 4.1 Hz, 0.5H), 4.18 (d, J=9.9 Hz, 0.5H), 3.98-3.80 (m, 1H), 3.74 (t, J=12.4 Hz, 0.5H), 3.66 (d, J=10.0 Hz, 0.5H), 3.39 (s, 1H), 2.76-2.62 (m, 1H), 2.63-2.34 (m, 3H), 2.16-2.06 (m, 1H), 1.82-1.69 (m, 1H), 1.59 (dt, J=13.8, 7.0 Hz, 2H), 1.52-1.41 (m, 2H), 1.29 (d, J=16.5 Hz, 3H), 1.23-1.09 (m, 3H), 1.09-0.98 (m, 2H), 0.97-0.83 (m, 4H), 0.79 (d, J=6.6 Hz, 2H), 0.61 (s, 1H), 0.52 (d, J=6.5 Hz, 2H). ESI MS m/z=634.44 [M−H]$^−$.

Step 13-2: A solution of the compound from Step 13-1 (14 mg, 0.022 mmol) in CH$_2$Cl$_2$ (0.3 ml) was treated with TEA (20 µl, 0.143 mmol) and TFAA (10 µl, 0.071 mmol) dropwise at 0° C. The reaction was stirred at 0° C. for 1 h, and then quenched with ammonium hydroxide. The mixture was stirred for additional 30 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 13 (12 mg, 0.019 mmol, 88% yield) as a white solid.

$^1$H NMR (400 MHz, Chloroform-d) (mixture of rotamers) δ 7.91 (s, 0.5H), 7.72 (s, 0.5H) 7.57-7.43 (m, 1H), 7.10 (s, 0.5H), 7.01 (td, J=7.7, 1.6 Hz, 1H), 6.92 (d, J=7.9 Hz, 0.5H), 6.88-6.70 (m, 2H), 6.64 (s, 0.5H), 6.49 (s, 0.5H), 5.56 (dd, J=9.3, 5.4 Hz, 0.5H), 5.25 (t, J=7.5 Hz, 0.5H), 5.12 (ddd, J=13.8, 10.2, 8.1 Hz, 1H), 4.46 (t, J=12.7 Hz, 0.5H), 4.38-4.29 (m, 0.5H), 4.22 (dd, J=10.6, 1.7 Hz, 0.5H), 4.12 (q, J=7.1 Hz, 1H), 3.92 (d, J=10.6 Hz, 1H), 3.77 (t, J=12.6 Hz, 0.5H), 3.61-3.47 (m, 0.5H), 3.45-3.35 (m, 0.5H), 2.90 (ddd, J=12.9, 10.2, 1.4 Hz, 1H), 2.71-2.61 (m, 0.5H), 2.61-2.43 (m, 2H), 1.85 (dt, J=13.7, 7.5 Hz, 0.5H), 1.76-1.56 (m, 5H), 1.53-1.35 (m, 2H), 1.35-1.21 (m, 4H), 1.21-1.10 (m, 2H), 1.10-0.99 (m, 2H), 0.91 (d, J=6.6 Hz, 1.5H), 0.86 (d, J=6.6 Hz, 1.5H), 0.70 (d, J=6.6 Hz, 1.5H), 0.62 (d, J=6.5 Hz, 1.5H), 0.51-0.36 (m, 1H). ESI MS m/z=616.30 [M−H]$^−$.

Example 14

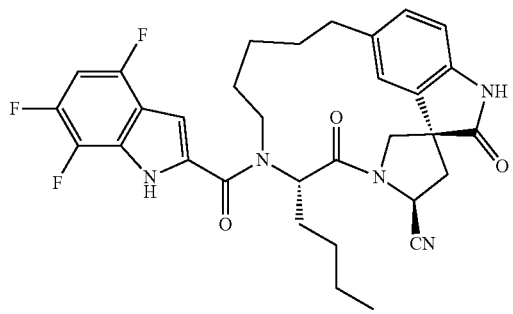

-continued
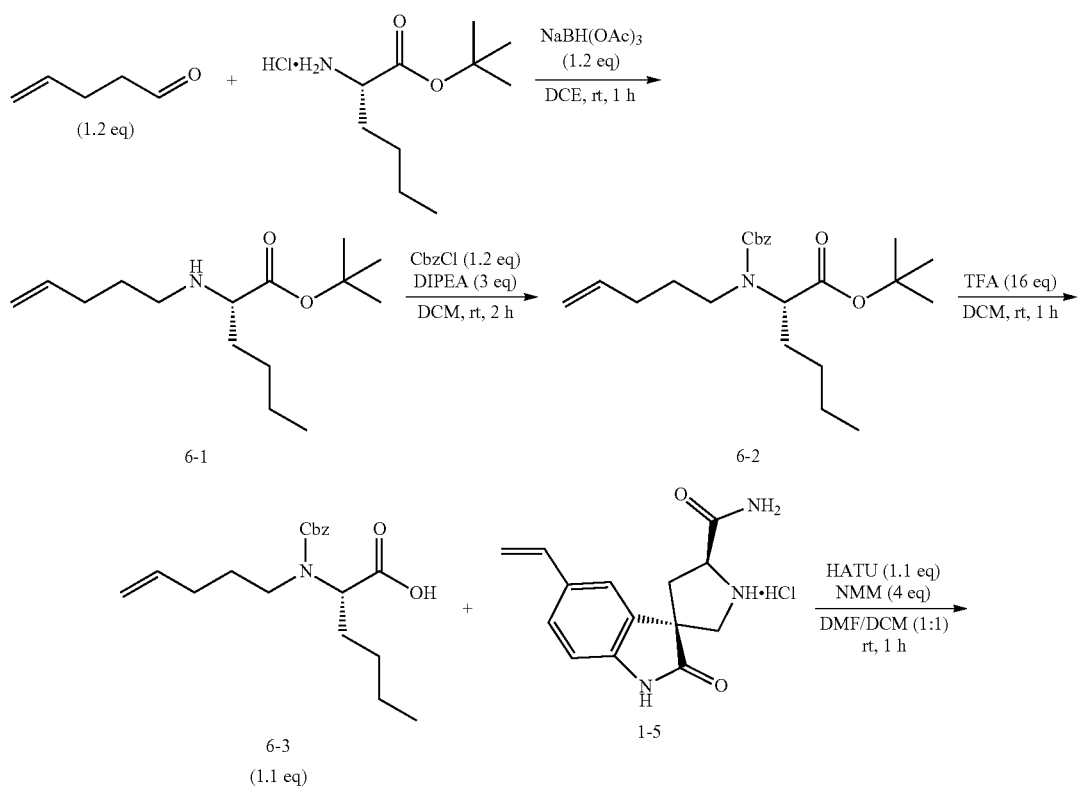
6-1
6-2
6-3 (1.1 eq)
1-5
6-5
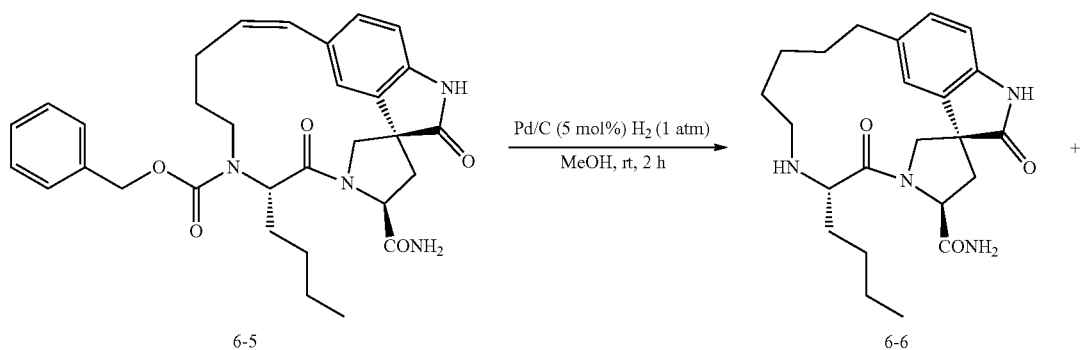
6-5
6-6

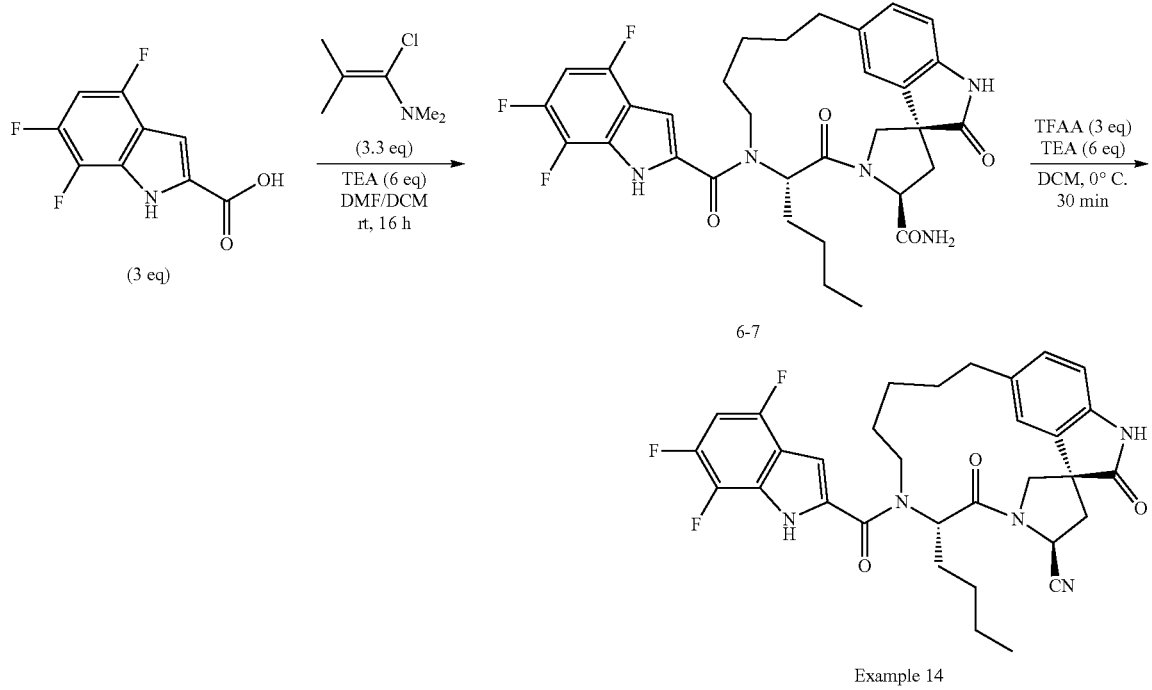

Example 14

Step 14-1: A solution of tert-butyl (S)-2-aminohexanoate (5 g, 26.7 mmol) and pent-4-enal (2.9 ml, 29.3 mmol) in DCE (100 ml) was treated with sodium triacetoxyborohydride (7.92 g, 37.4 mmol) portion wise at room temperature. The reaction was stirred at room temperature for 6 h. The reaction was quenched with a saturated solution of sodium bicarbonate. The mixture was stirred overnight. The aqueous layer was extracted with dichloromethane over 3 times. The combined organic layer was dried over sodium sulfate, filtered and concentrated in vacuo. The crude was added to a 80 g silica gel column and eluted by MTBE/cyclohexane from 0% to 100% to give the desired product (5 g, 19.58 mmol, 73% yield) as a colorless oil.

$^1$H NMR (500 MHz, Chloroform-d) δ 5.83 (ddt, J=16.9, 10.1, 6.6 Hz, 1H), 5.13-4.94 (m, 2H), 3.14 (tdd, J=8.7, 6.8, 6.4, 2.6 Hz, 1H), 2.69-2.49 (m, 2H), 2.18-2.06 (m, 2H), 1.71-1.57 (m, 3H), 1.55-1.27 (m, 15H), 0.99-0.88 (m, 3H). ESI MS m/z=256.49 [M+H]$^+$.

Step 14-2: A solution of the compound from Step 14-1 (5 g, 19.58 mmol) in CH$_2$Cl$_2$ (100 ml) was treated with DIPEA (11 ml, 63.0 mmol) and Cbz-Cl (3.4 ml, 23.82 mmol) dropwise at room temperature. The reaction was stirred at room temperature for 1 h and then quenched with a saturated solution of sodium bicarbonate. The aqueous layer was extracted with dichloromethane over 3 times. The combined organic layer was dried over sodium sulfate, filtered and concentrated in vacuo. The crude was added to a 120 g silica gel column and eluted by MTBE/cyclohexane from 0% to 10% to give the desired product (5.1 g, 13.09 mmol, 67% yield) as a colorless oil.

$^1$H NMR (500 MHz, Chloroform-d) δ 7.42-7.25 (m, 5H), 5.89-5.68 (m, 1H), 5.28-4.90 (m, 3H), 4.20 (ddd, J=94.0, 9.7, 5.5 Hz, 1H), 3.48-3.30 (m, 1H), 3.10-2.93 (m, 1H), 2.14-1.86 (m, 2H), 1.83-1.58 (m, 2H), 1.54-1.44 (m, 1H), 1.43-1.20 (m, 15H), 0.89 (tt, J=12.3, 5.0 Hz, 3H). ESI MS m/z=412.51 [M+Na]$^+$.

Step 14-3: A solution of the compound from Step 14-2 (5.1 g, 13.09 mmol) in CH$_2$Cl$_2$ (30 ml) was treated with TFA (12 ml, 156 mmol) dropwise at 0° C. The reaction was warmed to room temperature and stirred for 4 h. The reaction was concentrated in vacuo. The crude was co-evaporated with toluene twice, and then dried over high vacuum to give the desired product (4.5 g, 13.50 mmol, 103% yield) as a colorless syrup.

$^1$H NMR (400 MHz, Chloroform-d) δ 7.31 (d, J=37.4 Hz, 5H), 5.87-5.64 (m, 1H), 5.16 (d, J=13.2 Hz, 2H), 4.99 (q, J=14.2, 10.7 Hz, 2H), 4.60 (s, 1H), 4.23 (dd, J=9.4, 5.8 Hz, 1H), 3.43 (s, 1H), 3.10 (ddd, J=14.8, 9.8, 5.4 Hz, 1H), 2.16-1.92 (m, 3H), 1.74 (d, J=73.8 Hz, 3H), 1.34 (s, 4H), 0.89 (d, J=7.8 Hz, 3H). ESI MS m/z=332.28 [M−H]$^-$.

Step 14-4: A suspension of the compound from Step 14-3 (1.06 g, 3.18 mmol) and the compound from Step 1-5 (0.762 g, 2.96 mmol) in DMF (3 ml) and CH$_2$Cl$_2$ (9 ml) was treated with N-methyl morpholine (1 ml, 9.10 mmol) and HATU (1.2 g, 3.16 mmol). The reaction was stirred at room temperature overnight. The mixture was concentrated and then quenched with a saturated solution of sodium bicarbonate. The mixture was diluted with ethyl acetate. The organic layer was washed with brine over 3 times, dried over sodium sulfate, filtered and concentrated in vacuo. The crude was added to a 40 g silica gel column and eluted by acetone/cyclohexane from 0% to 100% to give the desired product (447 mg, 0.781 mmol, 26% yield) as a white foam.

ESI MS m/z=571.46 [M−H]$^-$.

Step 14-5: A solution of the compound from Step 14-4 (440 mg, 0.768 mmol) in toluene (770 ml) was treated with Zhan 1B cat. (114 mg, 0.155 mmol) under N$_2$. The mixture was degassed and backfilled with N$_2$ at −78° C. by freeze-pump-thaw over 3 times. The reaction was warmed to 90° C. and stirred overnight. The mixture was concentrated in vacuo. The crude was added to a 24 g silica gel column and eluted by acetone/cyclohexane from 0% to 100% to give the desired product (324 mg, 0.595 mmol, 77% yield) as a brownish solid.

¹H NMR (500 MHz, Chloroform-d) δ 8.86 (s, 1H), 7.25-7.18 (m, 2H), 7.15 (td, J=7.0, 6.4, 3.6 Hz, 2H), 7.08 (d, J=7.4 Hz, 1H), 6.99 (d, J=7.1 Hz, 1H), 6.92 (dd, J=8.1, 3.9 Hz, 1H), 6.89-6.83 (m, 1H), 6.52 (d, J=26.2 Hz, 1H), 6.43 (d, J=11.0 Hz, 1H), 5.88 (s, 1H), 5.59-5.75 (m, 1H), 5.22-5.06 (m, 1H), 5.03 (d, J=12.2 Hz, 1H), 4.84 (d, J=12.0 Hz, 1H), 4.79-4.66 (m, 1H), 4.12 (q, J=10.4 Hz, 1H), 3.94-3.65 (m, 1H), 3.60 (t, J=13.3 Hz, 1H), 3.40 (t, J=15.0 Hz, 1H), 2.79 (dt, J=45.1, 11.6 Hz, 1H), 2.31-2.22 (m, 1H), 2.12-1.93 (m, 1H), 1.93-1.66 (m, 4H), 1.55 (ddd, J=54.0, 26.8, 11.9 Hz, 2H), 1.39-1.23 (m, 2H), 1.22-1.03 (m, 2H), 0.79-0.89 (m, 3H). ESI MS m/z=543.44 [M−H]⁻.

Step 14-6: A solution of the compound from Step 14-5 (100 mg, 0.184 mmol) in MeOH (1 ml) was treated with Pd—C (8 mg, 7.52 µmol) under H₂. The mixture was bubbled with H₂ for 5 min. The reaction was stirred at room temperature overnight. The mixture was filtered through celite and rinsed with methanol. The filtrate was concentrated in vacuo to give the desired product (76 mg, 0.184 mmol, 100% yield) as a brownish solid.

ESI MS m/z=413.50 [M+H]⁺.

Step 14-7: A suspension of 4,6,7-trifluoro-1H-indole-2-carboxylic acid (42 mg, 0.195 mmol) in CH₂Cl₂ (0.4 ml) was treated with 1-chloro-N,N,2-trimethylprop-1-en-1-amine (28.4 µl, 0.215 mmol) dropwise at room temperature. The reaction was stirred at room temperature for 1 h. The resulting solution of 4,6,7-trifluoro-1H-indole-2-carbonyl chloride (0.488 M) in DCM was freshly used. A solution of the compound from Step 14-6 (14 mg, 0.034 mmol) in DMF (0.1 ml) was treated with TEA (30 µl, 0.215 mmol) and a freshly prepared stock solution of 4,6,7-trifluoro-1H-indole-2-carbonyl chloride (0.488 M, 220 µl, 0.106 mmol) in CH₂Cl₂ dropwise at room temperature. The reaction was stirred at room temperature overnight, then quenched with ammonium hydroxide and stirred for additional 30 min. The aqueous layer was extracted with ethyl acetate over 3 times. The combined organic layer was dried over sodium sulfate, filtered and concentrated in vacuo. The crude was added to a 4 g silica gel column and eluted by acetone/cyclohexane from 0% to 100% to give the desired product (5 mg, 8.20 µmol, 24% yield) as a white solid.

ESI MS m/z=608.42 [M−H]⁻.

Step 14-8: A solution of the compound from Step 14-7 (9 mg, 0.015 mmol) in CH₂Cl₂ (0.3 ml) was treated with TEA (18 µl, 0.129 mmol) and TFAA (8 µl, 0.057 mmol) dropwise at 0° C. The reaction was stirred at 0° C. for 1 h, then quenched with a saturated solution of sodium bicarbonate and stirred for additional 30 min. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 14 (8 mg, 0.014 mmol, 92% yield) as a white solid.

¹H NMR (500 MHz, Chloroform-d) δ 9.33 (s, 1H), 8.04 (s, 1H), 7.02 (dd, J=8.0, 1.6 Hz, 1H), 6.89 (d, J=7.9 Hz, 1H), 6.79 (t, J=2.5 Hz, 1H), 6.70-6.64 (m, 1H), 6.64-6.61 (m, 1H), 5.32 (d, J=16.7 Hz, 1H), 5.21 (dd, J=10.3, 8.0 Hz, 1H), 4.22 (d, J=19.7 Hz, 1H), 4.12 (q, J=7.1 Hz, 2H), 4.02 (d, J=10.4 Hz, 1H), 3.80 (d, J=15.0 Hz, 1H), 2.94 (dd, J=12.8, 10.3 Hz, 1H), 2.69-2.47 (m, 4H), 2.13-2.05 (m, 1H), 1.89 (dq, J=14.7, 7.5 Hz, 1H), 1.75-1.53 (m, 7H), 1.43-1.32 (m, 4H), 1.32-1.23 (m, 4H), 0.91 (t, J=7.2 Hz, 4H), 0.87-0.76 (m, 1H). ESI MS m/z=590.28 [M−H]⁻.

Example 15

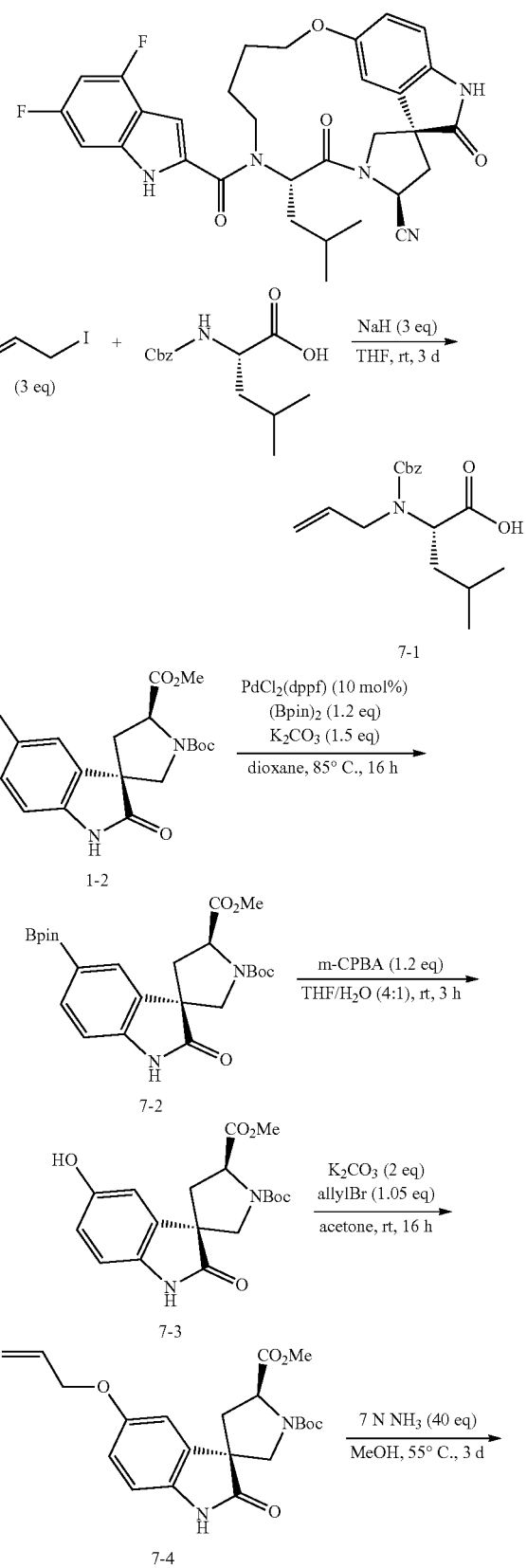

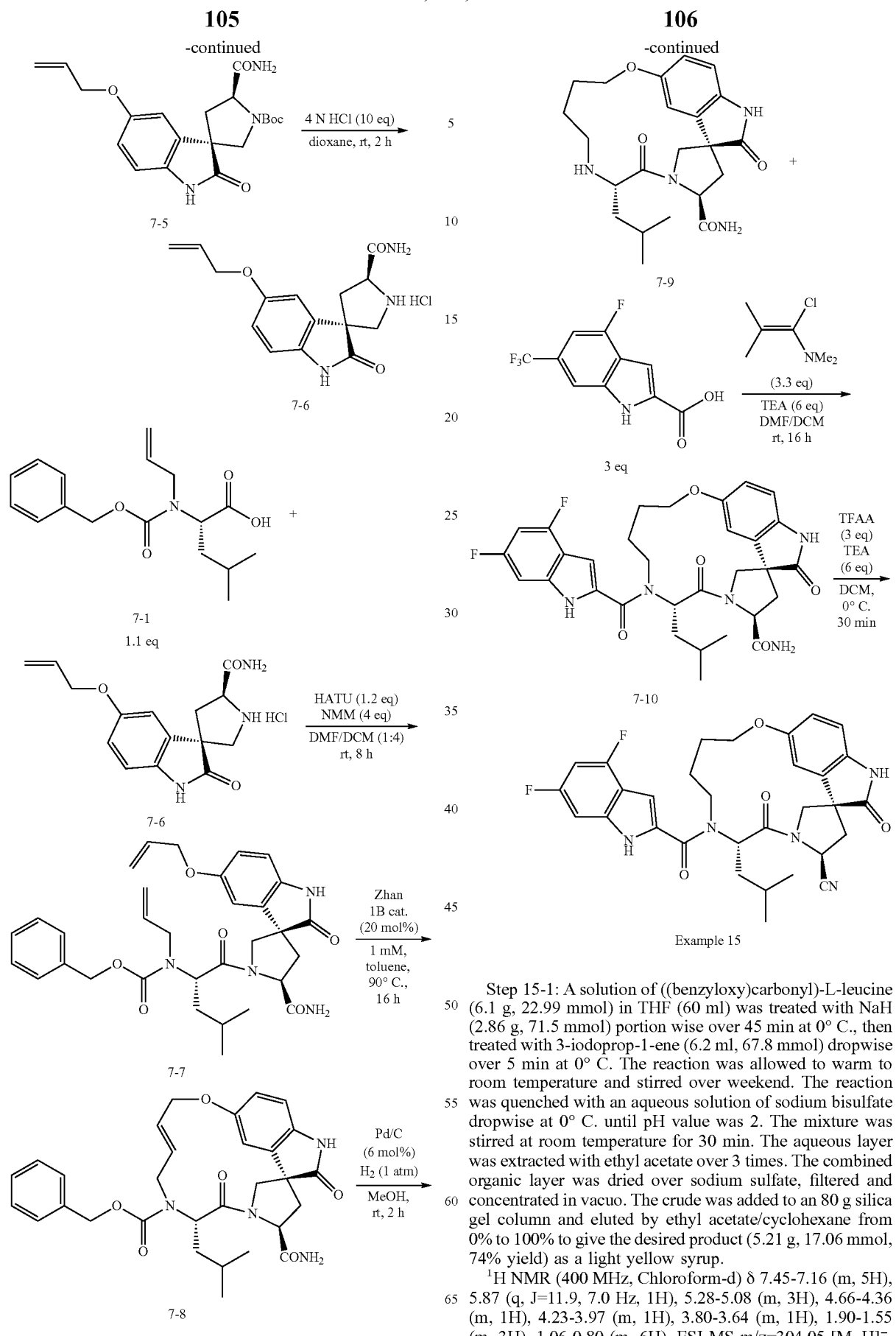

Example 15

Step 15-1: A solution of ((benzyloxy)carbonyl)-L-leucine (6.1 g, 22.99 mmol) in THF (60 ml) was treated with NaH (2.86 g, 71.5 mmol) portion wise over 45 min at 0° C., then treated with 3-iodoprop-1-ene (6.2 ml, 67.8 mmol) dropwise over 5 min at 0° C. The reaction was allowed to warm to room temperature and stirred over weekend. The reaction was quenched with an aqueous solution of sodium bisulfate dropwise at 0° C. until pH value was 2. The mixture was stirred at room temperature for 30 min. The aqueous layer was extracted with ethyl acetate over 3 times. The combined organic layer was dried over sodium sulfate, filtered and concentrated in vacuo. The crude was added to an 80 g silica gel column and eluted by ethyl acetate/cyclohexane from 0% to 100% to give the desired product (5.21 g, 17.06 mmol, 74% yield) as a light yellow syrup.

$^1$H NMR (400 MHz, Chloroform-d) δ 7.45-7.16 (m, 5H), 5.87 (q, J=11.9, 7.0 Hz, 1H), 5.28-5.08 (m, 3H), 4.66-4.36 (m, 1H), 4.23-3.97 (m, 1H), 3.80-3.64 (m, 1H), 1.90-1.55 (m, 3H), 1.06-0.80 (m, 6H). ESI MS m/z=304.05 [M−H]⁻.

Step 15-2: A solution of the compound from Step 15-1 (5.09 g, 11.97 mmol) in 1,4-Dioxane (50 ml) was treated with $K_2CO_3$ (2.53 g, 18.31 mmol), bis(pinacolato)di-boron (3.67 g, 14.45 mmol) and $PdCl_2$(dppf) (880 mg, 1.203 mmol) under $N_2$. The mixture was bubbled with $N_2$ over 10 min. The reaction was warmed to 85° C. and stirred overnight. The mixture was filtered through celite and rinsed with ethyl acetate. The filtrate was concentrated in vacuo. The crude was added to an 80 g silica gel column and eluted by ethyl acetate/cyclohexane from 0% to 100% to give the desired product (4.5 g, 9.53 mmol, 80% yield) as an off-white foam.

ESI MS m/z=471.33 [M−H]⁻.

Step 15-3: A solution of the compound from Step 15-2 (4.5 g, 9.53 mmol) in THF (20 ml) and water (5 ml) was treated with m-CPBA (2.8 g, 11.36 mmol). The reaction was stirred at room temperature for 3 h. The reaction was quenched with a saturated solution of sodium thiosulfate. The mixture was stirred for additional 30 min. The aqueous layer was extracted with ethyl acetate over 3 times. The combined organic layer was dried over sodium sulfate, filtered and concentrated in vacuo. The crude was added to an 80 g silica gel column and eluted by acetone/cyclohexane from 0% to 100% to give the desired product (2.4 g, 6.62 mmol, 70% yield) as a white foam.

$^1$H NMR (500 MHz, DMSO-$d_6$) δ 10.38 (d, J=5.0 Hz, 1H), 9.12 (d, J=9.3 Hz, 1H), 6.70 (dd, J=8.3, 1.9 Hz, 1H), 6.62 (ddd, J=8.3, 5.9, 2.4 Hz, 1H), 6.53 (t, J=2.0 Hz, 1H), 4.57-4.45 (m, 1H), 3.71 (d, J=16.2 Hz, 3H), 3.58-3.44 (m, 3H), 2.36 (ddd, J=12.6, 8.0, 1.4 Hz, 1H), 2.22 (ddd, J=24.0, 12.8, 9.2 Hz, 1H), 1.39 (d, J=5.2 Hz, 9H). ESI MS m/z=361.32 [M−H]⁻.

Step 15-4: A solution of the compound from Step 15-3 (2.19 g, 6.04 mmol) in acetone (25 ml) was treated with $K_2CO_3$ (1.78 g, 12.88 mmol) and allyl bromide (0.55 ml, 6.36 mmol). The reaction was stirred at room temperature overnight. The mixture was filtered and concentrated in vacuo. The crude was added to a 40 g silica gel column and eluted by acetone/cyclohexane from 0% to 100% to give the desired product (1.7 g, 4.22 mmol, 70% yield) as a white solid.

$^1$H NMR (500 MHz, Chloroform-d) δ 8.08 (d, J=7.4 Hz, 1H), 6.79-6.66 (m, 3H), 5.96 (dddt, J=17.2, 10.6, 8.8, 5.4 Hz, 1H), 5.34 (dq, J=17.2, 1.5 Hz, 1H), 5.23 (ddq, J=9.8, 6.9, 1.4 Hz, 1H), 4.67-4.49 (m, 1H), 4.41 (ddt, J=9.1, 5.4, 1.6 Hz, 2H), 3.78 (d, J=1.6 Hz, 1H), 3.72 (s, 3H), 3.63 (dd, J=10.6, 1.6 Hz, 1H), 2.49 (ddd, J=16.7, 12.8, 9.1 Hz, 1H), 2.36-2.26 (m, 1H), 1.40 (d, J=9.5 Hz, 9H). ESI MS m/z=401.29 [M−H]⁻.

Step 15-5: The compound from Step 15-4 (2 g, 4.97 mmol) was treated with 7 N ammonia in MeOH (30 ml, 210 mmol). The reaction was warmed to 55° C. and stirred over weekend. The mixture was concentrated in vacuo and dried under high vacuum to give the desired product (1.85 g, 4.77 mmol, 96% yield) as an off-white solid.

$^1$H NMR (500 MHz, DMSO-$d_6$) δ 10.48 (s, 1H), 7.53-7.44 (m, 1H), 7.16-7.04 (m, 1H), 6.87-6.78 (m, 2H), 6.55 (dd, J=17.4, 2.4 Hz, 1H), 6.01 (dddd, J=22.6, 10.5, 7.0, 5.2 Hz, 1H), 5.36 (dtd, J=17.3, 4.3, 3.9, 1.8 Hz, 1H), 5.28-5.21 (m, 1H), 4.54-4.38 (m, 3H), 3.62-3.44 (m, 2H), 2.19 (t, J=9.7 Hz, 2H), 1.39 (d, J=20.9 Hz, 9H). ESI MS m/z=386.32 [M−H]⁻.

Step 15-6: A suspension of the compound from Step 15-5 (1.8 g, 4.65 mmol) in 1,4-dioxane (12 ml) was treated with 4N HCl in dioxane (15 ml, 60.0 mmol). The reaction was stirred at room temperature for 3 h. The mixture was concentrated in vacuo and dried under high vacuum to give the desired product (1.7 g, 5.25 mmol, 113% yield) as a white solid.

$^1$H NMR (400 MHz, DMSO-$d_6$) δ 10.58 (d, J=4.3 Hz, 1H), 9.14 (s, 1H), 8.07-7.90 (m, 1H), 7.78 (s, 1H), 7.46-7.24 (m, 1H), 6.95-6.69 (m, 2H), 6.17-5.97 (m, 1H), 5.42 (dq, J=17.2, 2.0 Hz, 1H), 5.34-5.18 (m, 1H), 4.72-4.59 (m, 1H), 4.54 (td, J=4.4, 3.4, 1.8 Hz, 2H), 3.57 (d, J=3.1 Hz, 4H), 3.46 (dd, J=12.0, 2.8 Hz, 1H), 2.22 (ddd, J=13.4, 10.8, 2.5 Hz, 1H). ESI MS m/z=288.34 [M+H]⁺.

Step 15-7: A solution of the compound Step 15-1 (543 mg, 1.778 mmol) and the compound from Step 15-6 (500 mg, 1.544 mmol) in DMF (1.5 ml) and $CH_2Cl_2$ (4.5 ml) was treated with N-methyl morpholine (700 μl, 6.37 mmol) and HATU (704 mg, 1.851 mmol). The reaction was stirred at room temperature for 8 h, quenched with a saturated solution of sodium bicarbonate and diluted with ethyl acetate. The organic layer was washed with brine over 3 times, dried over sodium sulfate, filtered and concentrated in vacuo. The crude was added to a 40 g silica gel column and eluted by acetone/cyclohexane from 0% to 100% to give the desired product (680 mg, 1.183 mmol, 77% yield) as a white solid.

$^1$H NMR (500 MHz, Methanol-$d_4$) δ 7.28 (s, 2H), 7.19 (s, 1H), 7.01 (d, J=7.6 Hz, 1H), 6.89 (d, J=8.9 Hz, 1H), 6.79 (d, J=8.4 Hz, 1H), 6.56 (d, J=2.5 Hz, 1H), 6.04 (s, 1H), 5.99-5.78 (m, 2H), 5.40 (d, J=17.0 Hz, 1H), 5.28 (d, J=17.7 Hz, 1H), 5.22-5.01 (m, 3H), 4.73 (dt, J=19.2, 9.9 Hz, 2H), 4.60 (d, J=20.0 Hz, 2H), 4.49 (s, 1H), 4.39-4.29 (m, 1H), 4.28-4.10 (m, 2H), 4.00 (dd, J=15.8, 5.7 Hz, 1H), 3.90 (dd, J=14.8, 8.1 Hz, 1H), 3.78-3.57 (m, 2H), 2.39 (ddd, J=46.7, 24.7, 10.3 Hz, 2H), 1.74-1.58 (m, 2H), 1.58-1.47 (m, 1H), 0.92 (q, J=13.6, 9.8 Hz, 4H). ESI MS m/z=573.25 [M−H]⁻.

Step 15-8: A solution of the compound from Step 15-7 (680 mg, 1.183 mmol) in toluene (1200 ml) was treated with Zhan 1B cat. (178 mg, 0.243 mmol) under $N_2$. The mixture was degassed and backfilled with $N_2$ through freeze-pump-thaw at −78° C. over 5 times. The reaction was warmed to 90° C. and stirred overnight. The mixture was concentrated in vacuo. The crude was added to a 40 g silica gel column and eluted by acetone/cyclohexane from 0% to 100% to give the desired product (600 mg, 1.098 mmol, 93% yield) as a brownish solid.

$^1$H NMR (500 MHz, Methanol-$d_4$) δ 7.38-7.21 (m, 3H), 7.19-7.03 (m, 2H), 6.89-6.75 (m, 2H), 6.72-6.61 (m, 1H), 5.76 (dt, J=15.5, 7.3 Hz, 2H), 5.52 (ddd, J=15.8, 8.4, 3.6 Hz, 1H), 5.03 (d, J=16.7 Hz, 2H), 4.72-4.48 (m, 4H), 4.08 (dd, J=16.8, 9.1 Hz, 2H), 3.97 (s, 1H), 3.88 (d, J=10.5 Hz, 1H), 3.59 (d, J=41.0 Hz, 2H), 2.51-2.40 (m, 2H), 2.40-2.30 (m, 1H), 1.64 (dt, J=14.2, 7.4 Hz, 2H), 1.50-1.39 (m, 1H), 0.93 (dd, J=13.3, 6.6 Hz, 7H). ESI MS m/z=545.37 [M−H]⁻.

Step 15-9: A solution of the compound from Step 15-8 (600 mg, 1.098 mmol) in MeOH (10 ml) was treated with Pd—C (75 mg, 0.070 mmol) under $H_2$ (2.213 mg, 1.098 mmol) (1 atm). The reaction was stirred at room temperature for 3 h. The mixture was filtered through celite and rinsed with methanol. The filtrate was concentrated in vacuo. The crude mixture was added to a 24 g silica gel column and eluted by dichloromethane/methanol from 0% to 20% to give the desired product (145 mg, 0.350 mmol, 32% yield) as a white solid.

$^1$H NMR (400 MHz, Methanol-$d_4$) δ 6.86 (d, J=8.4 Hz, 1H), 6.79 (dd, J=8.4, 2.5 Hz, 1H), 6.75 (d, J=2.5 Hz, 1H), 4.29 (dt, J=12.8, 6.4 Hz, 1H), 4.18 (d, J=10.3 Hz, 1H), 4.01 (dt, J=12.8, 6.6 Hz, 1H), 3.87 (d, J=10.3 Hz, 1H), 3.65 (t, J=7.0 Hz, 1H), 2.67-2.51 (m, 2H), 2.51-2.37 (m, 2H), 1.81-1.68 (m, 1H), 1.68-1.57 (m, 2H), 1.48 (ddt, J=26.2, 12.9, 7.2 Hz, 4H), 0.91 (dd, J=17.9, 6.3 Hz, 6H). ESI MS m/z=415.44 [M+H]$^+$.

Step 15-10: A suspension of 4,6-difluoro-1H-indole-2-carboxylic acid (63 mg, 0.320 mmol) in DCM (0.6 ml) was treated with 1-chloro-N,N,2-trimethylprop-1-en-1-amine (51 µl, 0.385 mmol) dropwise at room temperature. The reaction was stirred at room temperature for 2 h to give the resulting solution (0.533 M) of 4,6-difluoro-1H-indole-2-carbonyl chloride. A solution of the compound from Step 15-9 (20 mg, 0.048 mmol) in DMF (0.1 ml) was treated with TEA (40 µl, 0.287 mmol) and a freshly prepared stock solution of 4,6-difluoro-1H-indole-2-carbonyl chloride (300 µl, 0.150 mmol) in DCM dropwise. The reaction was stirred at room temperature overnight, and then quenched with ammonium hydroxide. The aqueous layer was extracted with ethyl acetate over 3 times. The combined organic layer was dried over sodium sulfate, filtered and concentrated in vacuo. The crude was added to a 4 g silica gel column and eluted by ethyl acetate/cyclohexane from 0% to 100% to give the desired product (9 mg, 0.015 mmol, 31% yield) as a white solid.

$^1$H NMR (400 MHz, Chloroform-d) δ 9.56 (s, 1H), 8.47 (s, 1H), 6.96-6.72 (m, 3H), 6.63 (td, J=10.0, 2.0 Hz, 2H), 6.36 (s, 1H), 5.99 (s, 1H), 5.53 (s, 1H), 4.97 (t, J=9.0 Hz, 1H), 4.55 (s, 1H), 4.30-4.12 (m, 2H), 4.06 (d, J=10.4 Hz, 1H), 3.91 (d, J=14.8 Hz, 1H), 3.85-3.70 (m, 1H), 3.10-2.88 (m, 1H), 2.48-2.32 (m, 1H), 1.87 (d, J=20.0 Hz, 2H), 1.81-1.51 (m, 9H), 1.31 (d, J=6.8 Hz, 1H), 0.96 (dd, J=33.6, 6.6 Hz, 6H). ESI MS m/z=592.34 [M-H]$^-$.

Step 15-11: A solution of the compound from Step 15-10 (8 mg, 0.013 mmol) in $CH_2Cl_2$ (0.3 ml) was treated with TEA (14 µl, 0.100 mmol) and TFAA (7 µl, 0.050 mmol) at 0° C. The reaction was stirred at 0° C. for 30 min, and then quenched with ammonium hydroxide. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 15 (6 mg, 10.42 µmol, 77% yield) as a white solid.

$^1$H NMR (400 MHz, Chloroform-d) δ 8.98 (s, 1H), 7.75 (s, 1H), 6.87 (d, J=8.6 Hz, 1H), 6.85-6.82 (m, 1H), 6.78 (td, J=9.2, 8.6, 2.2 Hz, 2H), 6.62 (td, J=9.9, 2.0 Hz, 1H), 6.31 (t, J=2.5 Hz, 1H), 5.59 (t, J=7.5 Hz, 1H), 5.04 (dd, J=10.1, 8.1 Hz, 1H), 4.57 (s, 1H), 4.35-4.16 (m, 2H), 4.04 (d, J=10.5 Hz, 1H), 3.89 (d, J=14.9 Hz, 1H), 3.74-3.62 (m, 1H), 2.95 (ddd, J=13.0, 10.1, 5.7 Hz, 1H), 2.65-2.54 (m, 1H), 2.08-1.96 (m, 2H), 1.78 (dt, J=13.7, 6.8 Hz, 2H), 1.68 (d, J=12.8 Hz, 1H), 1.37 (dt, J=13.6, 6.2 Hz, 1H), 1.19 (s, 1H), 1.05-0.88 (m, 6H), 0.84 (d, J=7.0 Hz, 1H). ESI MS m/z=574.38 [M-H]$^-$.

Biological Activity

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 µL of test compound was dissolved in DMSO then incubated with SARS-CoV-2 3CL-protease (10 nM) in 10 µL assay buffer (50 mM HEPES [pH 7.5], 1 mM DTT, 0.01% BSA, 0.01% Triton-X 100) for 30 min at RT. Next, 10 µL of 3CL-protease substrate (40 µM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 µM). Data were fitted to normalized activity (variable slope) versus concentration fit in GraphPad Prism 7 to determine $IC_{50}$. All experiments were run in duplicate, and $IC_{50}$ ranges are reported as follows: A<0.1 µM; B 0.1-1 µM; C>1 µM.

SARS-CoV-2 Cellular Assay (Vero 76): Test compounds are serially diluted using eight half-log dilutions in test medium (MEM supplemented with 2% FBS and 50 pg/mL gentamicin).

Each dilution is added to 5 wells of a 96-well plate with 80-100% confluent Vero 76 cells. Three wells of each dilution are infected with virus (SARS-CoV-2 USA-WA1/2020), and two wells remain uninfected as toxicity controls. Six wells are infected and untreated as virus controls, and six wells are uninfected and untreated as cell controls. Viruses are prepared to achieve the lowest possible multiplicity of infection (MOI ~0.002) that would yield >80% cytopathic effect (CPE) at 6 days. Plates are incubated at 37±2° C., 5% $CO_2$. For neutral red assay, on day 6 post-infection, once untreated virus control wells reach maximum CPE, plates are stained with neutral red dye for approximately 2 hours (±15 minutes). Supernatant dye is removed, and wells are rinsed with PBS, and the incorporated dye is extracted in 50:50 Sorensen citrate buffer/ethanol for >30 minutes and the optical density is read on a spectrophotometer at 540 nm. Optical densities are converted to percent of cell controls and normalized to the virus control, then the concentration of test compound required to inhibit CPE by 50% ($EC_{50}$) is calculated by regression analysis. The concentration of compound that would cause 50% cell death in the absence of virus was similarly calculated ($CC_{50}$). $EC_{50}$ ranges are reported as follows: A<1 µM; B 1-10 µM; C>10 µM. $CC_{50}$ ranges are reported as follows: A<1 µM; B 1-50 µM; C>50 µM.

229E Cellular Assay (MRC5): $EC_{50}$ ranges are reported as follows: A<0.1 µM; B 0.1-1 µM; C>1 µM.

Viral stock preparation: MRC-5 cells, (a diploid cell culture line composed of fibroblasts, originally developed from the lung tissue of a 14-week-old aborted Caucasian male fetus), were used for the culturing of 229E human corona virus (hCoV). Flasks were inoculated with hCoV-229E and viral stocks were collected once cytopathic effect (CPE) was greater than 70%. Viral stocks in Growth Media (EMEM, 1% Penn/Strep, 1% nonessential amino acids, 10% heat-inactivated FBS) plus 5% glycerol were snap frozen using liquid nitrogen and stored at −80° C. Viral stock titers were quantified by a $TCID_{50}$ (50% median tissue culture infectious dose) assay, as described elsewhere.

229E live virus assay: 384-well black cell-culture-treated plastic clear-bottom plates are used in this assay. Using an ECHO liquid dispenser, 3-fold serial dilutions of control and test compounds suspended in DMSO are added to the plate wells in duplicate in a total volume of 125 nL per well. MRC-5 cells below passage 17 are seeded into the inner 240 wells of the 384-well plate at 1,500 cells per well in a volume of 12.5 µL using Growth Media. Viral stock is then added to the wells at a multiplicity of infection (MOI) of 0.05 in a volume of 12.5 µL per well, bringing the total volume of each well to ~25 µL. Each plate has a control row of 20 wells with cells plus DMSO and virus but no compound (positive control, max CPE, minimum ATPlite signal), and a row with cells plus DMSO but no compound or virus (negative control, minimum CPE, maximum ATPlite signal), and a row with no cells or virus or compound (background plate/reagent control). The control wells with cells but no virus are given an additional 12.5 µL of growth media containing an equal quantity of glycerol as those wells receiving the viral stock in order to keep consistent in media and volume conditions. The outer 2 rows/columns of wells are filled with 30 µL of moat media (DMEM, 1% Penn/Strep) to act as a thermal and evaporative barrier around the test wells. Following addition of all components, the sides of the plates are gently tapped by hand to promote even cell distribution across the wells. Upon confirmation of cell distribution, plates are incubated at 34° C. in a $CO_2$ humidity-controlled incubator for 6 days. Following the 6-day incubation period, the plates are read using ATPlite (12.5 µL added per well), which quantifies the amount of ATP (a measure of cell health) present in each well. Assay plates are read using an Envision luminometer. These data are used to calculate the percent cell health per well relative to the negative control wells and the $EC_{50}$ of each compound is calculated using ExcelFit software and 4-parameter logistical curve fitting analysis. $EC_{50}$ ranges are reported as follows: A<0.1 µM; B 0.1-1 µM; C>1 µM.

TABLE 1

Summary of Activities

| Example # | Vero 76 $EC_{50}$ | Vero 76 $CC_{50}$ | $EC_{50}$ (229E) | FRET $IC_{50}$ |
|---|---|---|---|---|
| 1 | — | — | B | A |
| 2 | — | — | B | A |
| 3 | — | — | B | A |
| 4 | A | B | A | A |
| 5 | A | B | A | A |
| 6 | — | — | A | B |
| 7 | A | B | A | A |
| 8 | — | — | B | B |
| 9 | — | — | A | A |
| 10 | — | — | — | A |
| 11 | | | A | A |
| 12 | | | A | A |
| 13 | | | | A |
| 14 | | | A | A |
| 15 | | | | A |

While this invention has been particularly shown and described with references to preferred embodiments thereof, it will be understood by those skilled in the art that various changes in form and details may be made therein without departing from the scope of the invention encompassed by the appended claims.

What is claimed:
1. A compound represented by Formula (XIII-6A),

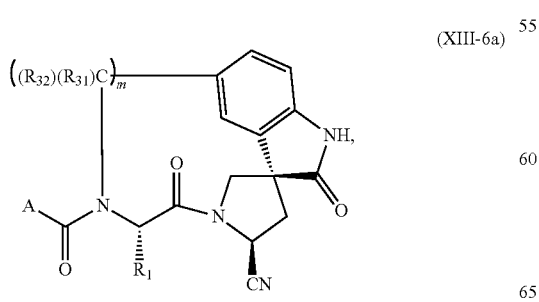

wherein m is 4;

L is —$CH_2$— or —O—;

each $R_{31}$ and $R_{32}$ is hydrogen;

$R_1$ is $C_1$-$C_8$-alkyl, arylalkyl or $C_3$-$C_6$-cycloalkyl-$C_1$-$C_4$-alkyl; and A is substituted or unsubstituted aryl, substituted or unsubstituted heteroaryl, or —(CO)—$NHR_2$, wherein $R_2$ is substituted or unsubstituted aryl, substituted or unsubstituted heteroaryl, substituted or unsubstituted alkyl, or substituted or unsubstituted cycloalkyl.

2. The compound of claim 1, wherein the compound is

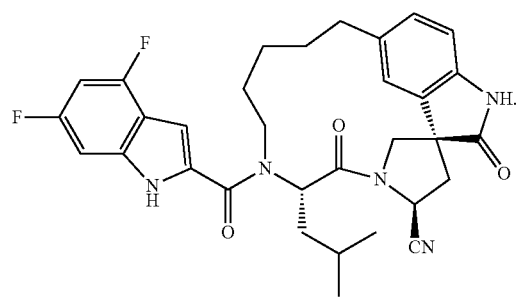 [SMILES: CC(C)C[C@H]1C(=O)N2C[C@]3(C[C@H]2C#N)C(=O)Nc2ccc(cc23)CCCCCN1C(=O)c1cc2c(F)cc(F)cc2[nH]1]

3. The compound of claim 1, wherein the compound is

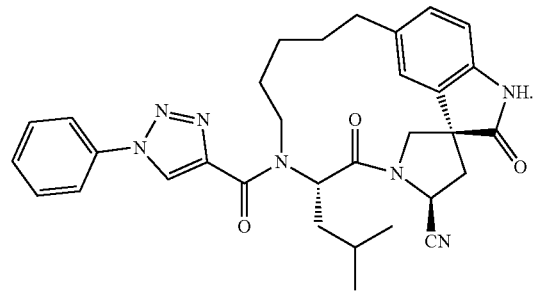 [SMILES: CC(C)C[C@H]1C(=O)N2C[C@]3(C[C@H]2C#N)C(=O)Nc2ccc(cc23)CCCCCN1C(=O)c1cn(-c2ccccc2)nn1]

4. The compound of claim 1, wherein the compound is

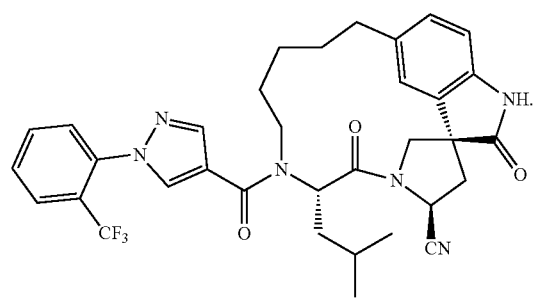 [SMILES: CC(C)C[C@H]1C(=O)N2C[C@]3(C[C@H]2C#N)C(=O)Nc2ccc(cc23)CCCCCN1C(=O)c1cnn(-c2ccccc2C(F)(F)F)c1]

5. The compound of claim 1, wherein the compound is

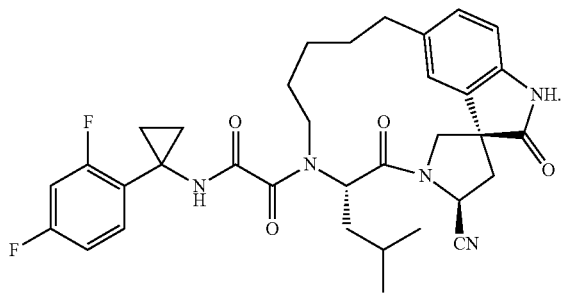 [SMILES: CC(C)C[C@H]1C(=O)N2C[C@]3(C[C@H]2C#N)C(=O)Nc2ccc(cc23)CCCCCN1C(=O)C(=O)NC1(c2ccc(F)cc2F)CC1]

6. The compound of claim 1, wherein the compound is

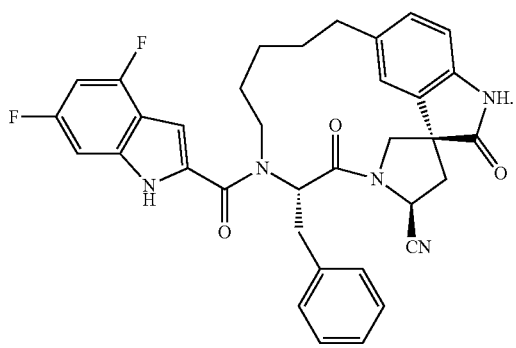 [SMILES: N#C[C@@H]1C[C@]23CN1C(=O)[C@H](Cc1ccccc1)N(C(=O)c1cc4c(F)cc(F)cc4[nH]1)CCCCCc1ccc(c2c1)NC3=O]

7. The compound of claim 1, wherein the compound is

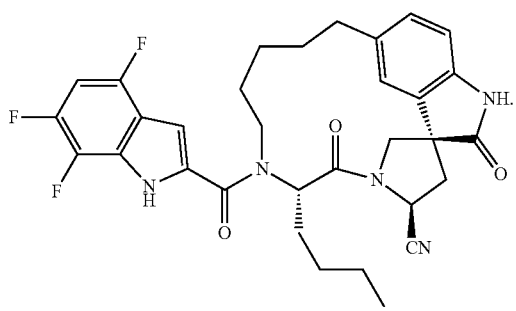 [SMILES: CCCC[C@H]1C(=O)N2C[C@]3(C[C@H]2C#N)C(=O)Nc2ccc(cc23)CCCCCN1C(=O)c1cc2c(F)cc(F)c(F)c2[nH]1]

8. The compound of claim 1, wherein the compound is

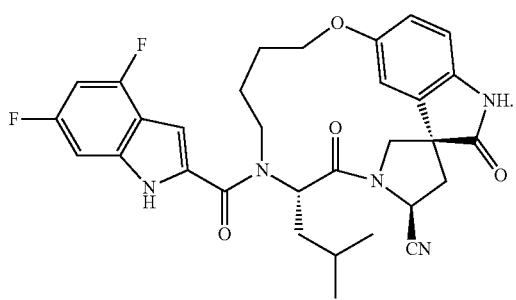 [SMILES: CC(C)C[C@H]1C(=O)N2C[C@]3(C[C@H]2C#N)C(=O)Nc2ccc(cc23)OCCCCN1C(=O)c1cc2c(F)cc(F)cc2[nH]1]

9. A pharmaceutical composition comprising the compound of claim 1 and a pharmaceutically acceptable carrier or excipient.

10. A pharmaceutical composition comprising the compound of claim 2 and a pharmaceutically acceptable carrier or excipient.

11. A pharmaceutical composition comprising the compound of claim 3 and a pharmaceutically acceptable carrier or excipient.

12. A pharmaceutical composition comprising the compound of claim 4 and a pharmaceutically acceptable carrier or excipient.

13. A pharmaceutical composition comprising the compound of claim 5 and a pharmaceutically acceptable carrier or excipient.

14. A pharmaceutical composition comprising the compound of claim 6 and a pharmaceutically acceptable carrier or excipient.

15. A pharmaceutical composition comprising the compound of claim 7 and a pharmaceutically acceptable carrier or excipient.

16. A pharmaceutical composition comprising the compound of claim 8 and a pharmaceutically acceptable carrier or excipient.

17. A method of treating a coronavirus infection in a subject in need thereof, comprising administering to the subject a therapeutically effective amount of the compound of claim 1.

18. A method of treating a coronavirus infection in a subject in need thereof, comprising administering to the subject a therapeutically effective amount of the compound of claim 2.

19. A method of treating a coronavirus infection in a subject in need thereof, comprising administering to the subject a therapeutically effective amount of the compound of claim 3.

20. A method of treating a coronavirus infection in a subject in need thereof, comprising administering to the subject a therapeutically effective amount of the compound of claim 4.

21. A method of treating a coronavirus infection in a subject in need thereof, comprising administering to the subject a therapeutically effective amount of the compound of claim 5.

22. A method of treating a coronavirus infection in a subject in need thereof, comprising administering to the subject a therapeutically effective amount of the compound of claim 6.

23. A method of treating a coronavirus infection in a subject in need thereof, comprising administering to the subject a therapeutically effective amount of the compound of claim 7.

24. A method of treating a coronavirus infection in a subject in need thereof, comprising administering to the subject a therapeutically effective amount of the compound claim 8.

* * * * *

UNITED STATES PATENT AND TRADEMARK OFFICE
CERTIFICATE OF CORRECTION

PATENT NO. : 11,319,325 B1
APPLICATION NO. : 17/479669
DATED : May 3, 2022
INVENTOR(S) : Jiajun Zhang et al.

Page 1 of 1

It is certified that error appears in the above-identified patent and that said Letters Patent is hereby corrected as shown below:

In the Claims

At Column 111

In Claim 1, Line 55 delete " 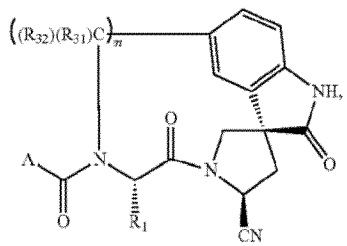 " and insert

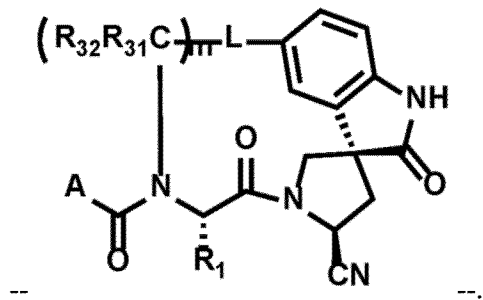

--.

Signed and Sealed this
Twenty-second Day of November, 2022

Katherine Kelly Vidal
*Director of the United States Patent and Trademark Office*